United States Patent [19]
Yang et al.

[11] Patent Number: 6,063,796
[45] Date of Patent: May 16, 2000

[54] SOMATOSTATIN AGONISTS

[75] Inventors: Lihu Yang, Edison; Arthur A. Patchett, Westfield; Alexander Pasternak, Princeton; Scott Berk, Maplewood; Meng Hsin Chen, Westfield; David Johnston, Warren; Kevin Chapman, Scotch Plains; Ravi Nargund, East Brunswick; James R. Tata, Westfield; Liangqin Guo, Edison, all of N.J.

[73] Assignee: Merck & Co., Inc., Rahway, N.J.

[21] Appl. No.: 09/053,299

[22] Filed: Apr. 1, 1998

Related U.S. Application Data

[60] Provisional application No. 60/042,637, Apr. 4, 1997, and provisional application No. 60/064,378, Nov. 6, 1997.

[51] Int. Cl.$^7$ ............... A61K 31/445; C07D 211/14; C07D 211/40
[52] U.S. Cl. ............................. 514/322; 546/199
[58] Field of Search ................ 514/322; 546/199

[56] References Cited

U.S. PATENT DOCUMENTS

| | | | |
|---|---|---|---|
| 4,225,472 | 9/1980 | Sarantakis | 514/11 |
| 4,242,347 | 12/1980 | Huebner | 546/210 |
| 4,310,518 | 1/1982 | Freidinger et al. | 514/11 |
| 5,360,807 | 11/1994 | Janssens et al. | 514/318 |
| 5,767,118 | 6/1998 | Nargund et al. | 514/226.4 |

FOREIGN PATENT DOCUMENTS

| | | |
|---|---|---|
| 2 311 523 | 1/1997 | Germany . |
| 196 36 623 | 3/1998 | Germany . |

OTHER PUBLICATIONS

Spatola et al. "Amide bond surrogates: psudopeptides and macrocycles" Tetrhedron, v.44(3), p821–833, 1988.

Hansen et al. "Polypepties. VIII. synthesisof L–and D–2, 6–diamino–4–hexynoic acid" CA 73::120889, 1970.

Hunter et al. "Identification and biosynthesis of N1, N9–bis(glutathionyl)aminopropylcadaverine in trypanosoma crizi" CA 121:296860, 1994.

Cavanak, T., et al., Chem. Abs., vol. 119, No. 23, Abs. No. 241372d, P. 69, 1993.

Maccoss, M., et al., Chem. Abs., vol. 128, No. 2, p. 386, Col. 1, Abs. No. 13436h, 1998.

Rudolf, K., et al., Chem. Abs., vol. 128, No. 19, p. 604, Abs. No. 230701v, 1998.

*Primary Examiner*—Ceila Chang
*Attorney, Agent, or Firm*—James L. McGinnis; David L. Rose

[57] ABSTRACT

This invention relates to somatostatin agonist compounds which are potent with high selectivity toward the receptor subtype 2. Compounds of the formula:

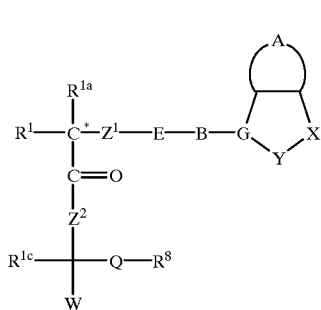

including pharmaceutically acceptable salts and hydrates thereof are disclosed. These compounds are useful in the treatment of diabetes, cancer, acromegaly, restenosis, depression, irritable bowel syndrome, pain and diabetic retinopathy. Many of the compounds are also orally active.

13 Claims, No Drawings

SOMATOSTATIN AGONISTS

This application is based on provisional application Nos. 60/042,637 filed Apr. 4, 1997 and 60/064,378 filed Nov. 6, 1997.

BACKGROUND OF THE INVENTION

Somatostatin (SST) is a widely distributed peptide occurring in two forms SST-14 (with 14 amino acids) and SST-28 (with 28 amino acids). SST has multiple functions including modulation of secretion of growth hormone, insulin, glucagon, pancreatic enzymes and gastric acid, in addition to having potent anti-proliferative effects.

The mechanism of action of somatostatin is mediated via high affinity membrane associated receptors. Five somatostatin receptors (SSTR1–5) are known (Reisine, T.; Bell, G. I. *Endocrine Reviews* 1995, 16, 427–442). All five receptors are heterogeneously distributed and pharmacologically distinct. Structure-function studies with a large number of peptidal analogs have shown that the Trp-Lys dipeptide of somatostatin is important for high-affinity binding. The availability of these receptors now makes it possible to design selectively active ligands for the sub-types to determine their physiological functions and to guide potential clinical applications. For example, studies utilizing subtype selective peptides have provided evidence that somatostatin subtype 2 receptors (SSTR2) mediates the inhibition of growth hormone release from the anterior pituitary and glucagon release from the pancreas, whereas SSTR5 selective agonists inhibit insulin release. These results imply the usefulness of SSTR2 selective analogs in the treatment of diabetes and many of the compounds of this invention have that selectivity.

In addition, the novel compounds described herein are useful in the therapy of a variety of conditions which include acromegaly, retinal neovascularization, neuropathic and visceral pain, irritable bowel syndrome, chronic atrophic gastritis, Crohn's disease, rheumatoid arthritis and sarcoidosis. The instant compounds inhibit cell proliferation and cause the regression of certain tumors including breast cancer. They are useful in preventing restenosis after angioplasty, they prevent non-steroid antiinflammatory drug (NSAID) induced ulcers, they are useful in treating colitis and to inhibit cystoid macular edema. Their central activities include promotion of REM sleep and an increase in cognitive function. They also have analgesic activities and can be used, for example, to treat cancer pain, cluster headache and post operative pain and they are useful in the prevention and treatment of migraine attacks and depression. The compounds described herein may be used in combination with other therapies, for example, with rapamycin to treat cancers, restenosis and atherosclerosis and with angiotensin converting enzyme inhibitors and insulin in the treatment of diabetes. The compounds of this invention are also remarkably reduced in size in comparison with the natural hormone and its peptide analogs such as octreotide and seglitide, which allows ease of formulation. Many of the instant compounds show activity following oral administration.

SUMMARY OF THE INVENTION

This invention relates to compounds represented by formula I:

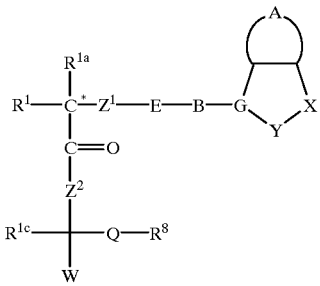

as well as pharmaceutically acceptable salts and hydrates thereof, wherein:

$R^1$ is selected from the group consisting of: -$C_{1-10}$-alkyl, -aryl, aryl($C_{1-6}$alkyl)-, ($C_{3-7}$cycloalkyl)($C_{1-6}$alkyl)-, ($C_{1-5}$alkyl)-K-($C_{1-5}$alkyl)-, aryl($C_0$-$C_5$alkyl)-K-($C_1$-$C_5$alkyl)-, and ($C_{3-7}$cycloalkyl)($C_{0-5}$alkyl)-K-($C_{1-5}$alkyl)-, the alkyl portions of which being optionally substituted with by 1 to 5 halogen groups, $S(O)_mR^2a$, 1 to 3 of $OR^{2a}$ groups or $C(O)OR^{2a}$, aryl is selected from the group consisting of: phenyl, naphthyl, biphenyl, quinolinyl, isoquinolinyl, indolyl, azaindole, pyridyl, benzothienyl, benzofuranyl, thiazolyl and benzimidazolyl, unsubstituted or substituted with: 1 to 3 $C_{1-6}$alkyl groups, 1 to 3 halo groups, 1 to 2 —$OR^2$ groups, methylenedioxy, —$S(O)_mR^2$, 1 to 2 —$CF_3$, —$OCF_3$ or $NO_2$ groups, —$N(R^2)C(O)(R^2)$, —$C(O)OR^2$, —$C(O)N(R^2)_2$, 1H-tetrazol-5-yl, —$SO_2N(R^2)_2$, —$N(R^2)SO_2$ phenyl, or —$N(R^2)SO_2R^2$;

K is selected from the group consisting of: —O—, —$S(O)_m$—, —$N(R^2)C(O)$—, —$C(O)N(R^2)$—, —$CR^2$=$CR^2$— and —C≡C—;

$R^{1a}$ is selected from the group consisting of: H and $C_{1-3}$ alkyl;

$R^{1c}$ is selected from the group consisting of: H, —$(CH_2)_q$ $SR^2$, —$(CH_2)_qOR^2$ and $C_{1-8}$alkyl;

$R^2$ is selected from the group consisting of: H, $C_{1-8}$alkyl, $(CH_2)_t$-aryl, and $C_{3-7}$cycloalkyl, and when two $R^2$ groups are present they may be taken together with the atom to which they are attached and with any intervening atoms to represent a $C_{3-8}$ ring, said ring optionally including O, S or $NR^{3a}$, where $R^{3a}$ is hydrogen, or $C_{1-6}$alkyl, said $C_{1-6}$ alkyl being optionally substituted by OH;

and when $R^2$ represents $C_{1-8}$alkyl, it may be substituted by 1 to 5 halo groups, $S(O)_mR^{2a}$, 1 to 3 $OR^{2a}$ groups or $C(O)OR^{2a}$;

$R^{2a}$ is selected from the group consisting of: H and $C_1$–$C_8$alkyl, optionally substituted with OH;

$Z^1$ is selected from the group consisting of: —O—, —$CH^2$— and —$NR^{2a}$;

$Z^2$ is selected from the group consisting of: —O—, —$CH_2$—, —$CHR^{2b}$— and —$NR^{2b}$, and when $Z^2$ represents $NR^{2b}$, it can be optionally linked to $R^{1c}$, Q or W to form a $C_{5-8}$ cyclic ring, which can optionally be interrupted by O, $S(O)_m$ or $NR^{2a}$;

$R^{2b}$ is selected from the group consisting of: H, $C_{1-8}$alkyl, —$(CH_2)_t$-aryl, —$(CH_2)_nCO_2R^2$, —$(CH_2)_nCON(R^2)_2$, —$(CH_2)_nOH$ and —$(CH_2)_nOR^2$;

W is selected from the group consisting of: H, $C_{1-8}$alkyl, —$(CH_2)_t$-aryl, wherein aryl is selected from phenyl, biphenyl and naphthyl, —$(CH_2)_t$-heteroaryl wherein heteroaryl is selected from tetrazolyl, oxadiazolyl, thiadiazolyl, triazolyl and pyrazinyl, —$(CH_2)_qC(O)OR^2$, —$(CH_2)_qOR^2$, —$(CH_2)_q$ $OC(O)R^2$, —$(CH_2)_qC(O)R^2$, —$(CH_2)_qC(O)(CH_2)_t$aryl, —(CH$_2$)$_q$N(R$^2$)C(O)R$^2$, —(CH$_2$)$_q$C(O)N(R$^2$)$_2$, —(CH$_2$)$_q$N(R$^2$)SO$_2$R$^2$, —(CH$_2$)$_q$N(R$^2$)C(O)N(R$^2$)$_2$, —(CH$_2$)$_q$OC(O)N(R$^2$)$_2$, —(CH$_2$)$_q$N(R$^2$)C(O)OR$^2$, —(CH$_2$)$_q$N(R$^2$)SO$_2$N(R$^2$)$_2$, and —(CH$_2$)$_q$S(O)$_m$R$^2$, wherein the heteroaryl portions thereof are optionally substituted with halo, R$^2$, N(R$^2$)$_2$ or OR$^2$, and R$^2$, (CH$_2$)$_q$ and (CH$_2$)$_t$ are optionally substituted with 1 to 2 of C$_{1-4}$alkyl, OH, OC$_{1-8}$ alkyl, O(CH$_2$)$_t$-aryl, OC$_{3-7}$ cycloalkyl, CO$_2$H, CO$_2$C$_{1-8}$ alkyl, CO$_2$(CH$_2$)$_t$-aryl, CO$_2$C$_{3-7}$ cycloalkyl or 1–3 halo groups, and said aryl portion is further optionally substituted with 1 to 3 of halogen, —OR$^2$, —CON(R$^2$)$_2$, —C(O)OR$^2$, C$_{1-4}$alkyl, —S(O)$_m$R$^2$, —N(R$^2$)$_2$, —CF$_3$ or 1H-tetrazol-5-yl;

Q represents a member selected from the group consisting of:

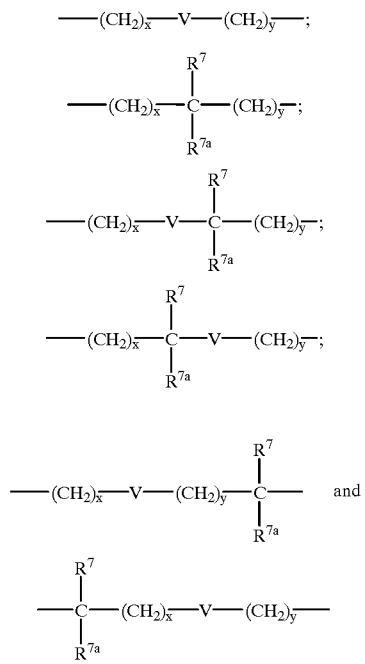

wherein x and y are independently 0, 1, 2, 3, 4, 5 or 6;

V is selected from the group consisting of —N(R$^{6a}$)—, —S(O)$_m$—, —O—, —CONR$^2$— and —NR$^2$CO—;

R$^{6a}$ is selected from the group consisting of hydrogen, C$_{1-8}$alkyl, R$^2$C(O)— and R$^2$SO$_2$—;

R$^7$ and R$^{7a}$ are independently selected from the group consisting of hydrogen, C$_{1-6}$alkyl, CF$_3$ and aryl;

R$^8$ is selected from the group consisting of —NR$^4$R$^5$, —N(=NR$^9$)NR$^{10}$ and —N$^+$(R$^4$)$_3$, wherein R$^4$ and R$^5$ are independently selected from the group consisting of: —R$^2$, —C(=NR$^2$)N(R$^2$)$_2$, —C(=NCN)N(R$^2$)$_2$, —C(=NC(O)R$^2$)N(R$^2$)$_2$, —C(=NSO$_2$R$^2$)N(R$^2$)$_2$, —C(=NNO$_2$)NR$^2$, heteroaryl, —C(=O)N(R$^2$)$_2$, —C(=O)R$^2$, 2,2,2-trifluoroethyl, 3,3,3-trifluoropropyl and (CH$_2$)$_t$-cyclopropyl, or R$^4$ and R$^5$ taken together represent —(CH$_2$)$_d$—L$_a$(CH$_2$)$_e$— where L$_a$ is —C(R$^2$)$_2$—, —O—, —S(O)$_m$— or —N(R$^2$)—, and d and e are independently 1 to 3, said heteroaryl and R$^2$ optionally substituted with 1–3 C$_{1-6}$alkyl groups, 1–7 halo groups, N(R$^2$)$_2$, OR$^2$, N(R$^2$)C(O)R$^2$, C(O)N(R$^2$), OC(O)R$^2$, S(O)$_m$R$^2$, CF$_3$, OCF$_3$, NO$_2$, N(R$^2$)C(O)(R$^2$), N(R$^2$)C(O)N(R$^2$)$_2$, C(O)OR$^2$, C(O)N(R$^2$)$_2$, SO$_2$N(R$^2$)$_2$, N(R$^2$)SO$_2$R$^2$, or methylenedioxy;

E is selected from the group consisting of: —SO$_2$—, —CO(C(R$^2$)$_2$)$_n$—, —C(=N—CN)—, —C(=N—NO$_2$)— and —C(=N—SO$_2$N(R$^2$)$_2$—;

R$^9$ and R$^{10}$ are independently H or C$_{1-8}$alkyl, or are optionally taken together and represent a C$_{3-8}$ cyclic ring, which is optionally interrupted by O, S(O)$_m$ or NR$^{2a}$;

B is selected from the group consisting of:

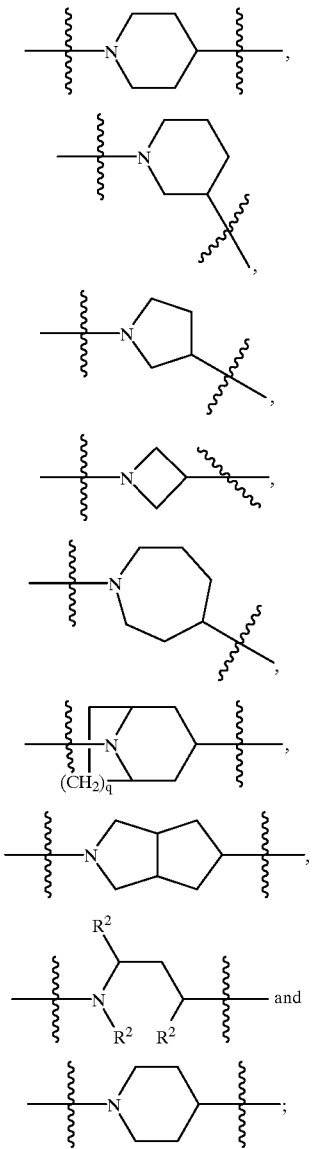

where attachment points are indicated by lines ($) external to the rings and to the open ring which are optionally substituted by C$_{1-6}$alkyl and where R$^2$ and (CH$_2$)$_q$ are described above;

represents an aromatic or non-aromatic 5–6 membered ring structure wherein:

G is N, CH or C;

Y is —C(O)—, —SO$_2$—, —C(OR$^{11}$)=, —C(SR$^{11}$)=, —C(NR$^{11}$)=, —C(R$^{11}$)$_{1-2}$=, =N—, NR$^{11}$, =NC(O)—, —N(R$^{11}$)C(R$^{11}$)$_2$— or —C(R$^{11}$)$_2$—; and X is —N(R$^{11}$)—, =N—, =N—C(R$^{11}$)$_2$—, —O—, —O—C(R$^{11}$)$_2$—, —S—, —S—C(R$^{11}$)$_2$— or C(R$^{11}$)$_2$;

$R^{11}$ is H, $C_1$–$C_8$ alkyl, —$(CH_2)_pOR^2$, —$(CH_2)_pN(R^2)_2$, $(CH2)_pN(R^2)C(O)N(R^2)_2$, —$(CH_2)_pN(R^2)C(O)R^2$, $(CH_2)_2$ heteroaryl, $(CH_2)_pN(R^2)SO_2C_1$–$C_4$ alkyl, —$(CH_2)_pC(O)N(R^2)_2$, or —$(CH_2)_pC(O)OR^2$ where heteroaryl is tetrazole, oxadiazole, imidazole or triazole which is optionally substituted with $R^2$, $OR^2$ or $N(R^2)_2$ and where p is 0–3;

A is a fused aromatic or non-aromatic ring, having 5–12 atoms, and containing 0–4 heteroatoms selected from O, S and N, optionally substituted with 1–3 groups selected from: $C_{1-6}$ alkyl, halo, —$OR^2$, $N(R^2)_2$, methylenedioxy, —$S(O)_mR^2$, —$CF_3$, —$OCF_3$, —$NO_2$, —$N(R^2)C(O)(R^2)$, —$C(O)OR^2$, —$C(O)N(R^2)_2$, -1H-tetrazol-5-yl, —$SO_2N(R^2)_2$, —$N(R^2)SO_2$ phenyl, $N(R^2)C(O)N(R^2)$ and —$N(R^2)SO_2R^2$;

m is an integer from 0 to 2;
n is an integer from 0 to 3;
q is an integer from 0 to 3; and
t is an integer from 0 to 3.

Pharmaceutical compositions and methods of treatment are also included.

DETAIL DESCRIPTION OF THE INVENTION

The compounds of the present invention are agonists of somatostatin and selective toward somatostatin receptor subtype SSTR2. The compounds have a number of clinical uses including in the treatment and prevention of diabetes, cancer, acromegaly, depression, chronic atrophic gastritis, Crohn's disease, ulcerative colitis, retinopathy, arthritis, pain both viseral and neuropathic and to prevent restenosis. Many of the compounds are orally active.

One object of this invention is to describe such compounds.

Another object is to describe preferred stereoisomers of the somatostatin agonists.

Another object is to describe processes for the preparation of such compounds.

Another object is to describe methods of use and compositions which contain the compounds as the active ingredient thereof. Further objects will become apparent from reading the following description.

In one aspect of the invention, the compounds and their pharmaceutically acceptable salts and hydrates of the present invention are those of structural formula I':

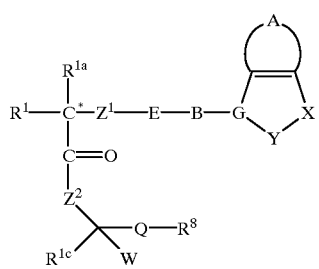

I' wherein
$R^1$ is selected from the group consisting of: $C_1$–$C_{10}$ alkyl, aryl, aryl ($C_1$–$C_6$ alkyl), ($C_3$–$C_7$ cycloalkyl)($C_1$–$C_6$ alkyl)—, ($C_1$–$C_5$ alkyl)-K-($C_1$–$C_5$ alkyl)—, aryl($C_0$–$C_5$ alkyl)-K-($C_1$–$C_5$ alkyl)—, and ($C_3$–$C_7$ cycloalkyl)($C_0$–$C_5$ alkyl)-K-($C_1$–$C_5$ alkyl)—, where K is —O—, —$S(O)_m$—, —$N(R^2)C(O)$—, —$C(O)N(R^2)$—, —$CR^2$=$CR^2$—, or —C∫C—, where $R^2$ and alkyl may be further substituted by 1 to 5 halogen, $S(O)_mR^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, -1H-tetrazol-5-yl, —$SO_2N(R^2)(R^2)$, —$N(R^2)SO_2$ phenyl, or —$N(R^2)SO_2R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl; Aryl is defined in the body of the case.

$R^{1a}$ is selected from the group consisting of hydrogen, and $C_1$–$C_3$ alkyl;

$R^{2a}$ is selected from the group consisting of hydrogen and $C_1$–$C_3$ alkyl, said alkyl optionally substituted by hydroxyl;

$R^{2b}$ is selected from hydrogen, $C_1$–$C_8$ alkyl, $(CH_2)_t$ aryl, —$(CH_2)_nCO_2R^2$, —$(CH_2)_nCON(R^2)_2$, —$(CH_2)_nOH$ or —$(CH_2)_nOR^2$;

$R^{1c}$ is selected from the group consisting of hydrogen, —$(CH_2)_qSR^2$, —$(CH_2)_qOR^2$ and $C_1$–$C_8$ alkyl;

$Z^1$ is selected from the group consisting of —O—, —$CH^2$— and —$NR^{2a}$;

$Z^2$ is selected from the group consisting of —O—, —$CH_2$—, —$CHR^{2b}$— and —$NR^{2b}$, when $Z^2$ is $NR^{2b}$ it can optionally be linked to $R^{1c}$, Q and/or W to form a $C_{5-8}$ cyclic ring, which can optionally be interrupted by oxygen, $S(O)_m$ or $NR^{2a}$;

W is selected from the group consisting of: hydrogen, $C_1$–$C_8$ alkyl, $(CH2)_t$ aryl, —$(CH_2)_qC(O)OR^2$, —$(CH_2)_qOR^2$, —$(CH_2)_qOC(O)R^2$, —$(CH_2)_qC(O)R^2$, —$(CH_2)_qC(O)(CH_2)_t$aryl, —$(CH_2)_qC(O)N(R^2)_2$, —$(CH_2)_qN(R^2)C(O)R^2$, —$(CH_2)_qN(R^2)SO_2R^2$, —$(CH_2)_qN(R^2)C(O)N(R^2)_2$, —$(CH_2)_qOC(O)N(R^2)_2$, —$(CH_2)_qN(R^2)C(O)OR^2$, —$(CH_2)_qN(R^2)SO_2N(R^2)_2$, —$(CH_2)_qS(O)_mR^2$, and $(CH_2)_t$ heteroaryl where the heteroaryl is tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ are optionally substituted with 1 to 2 $C_1$–$C_4$ alkyl, $OR^2$, $C(O)OR^2$, 1–3 halo and said aryl is optionally substituted with 1 to 3 halogen, —$OR^2$, —$CON(R^2)_2$, —$C(O)OR^2$, $C_1$–$C_4$ alkyl, —$S(O)_mR^2$, $N(R^2)_2$, $CF_3$ or 1H-tetrazol-5-yl;

Q is selected from the group consisting of:

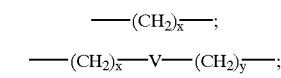

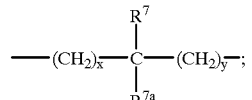

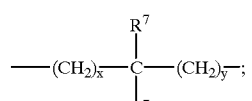

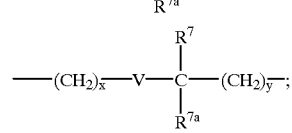

-continued

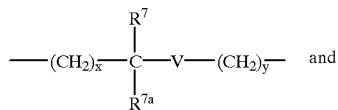 and

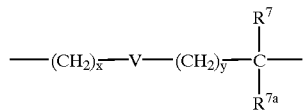

where x and y are independently 0, 1, 2, 3, 4, 5, 6;

V is selected from the group consisting of —N($R^{6a}$)—, —S(O)$_m$—, —O—, —CONR$^2$— and —NR$^2$CO—;

$R^{6a}$ is selected from the group consisting of hydrogen or $C_1$–$C_8$ alkyl, $R^2$CO— and $R^2SO_2$—;

$R^7$ and $R^{7a}$ are independently selected from the group consisting of hydrogen, $C_1$–$C_6$ alkyl, trifluoromethyl and aryl;

R8 is selected from the group consisting of

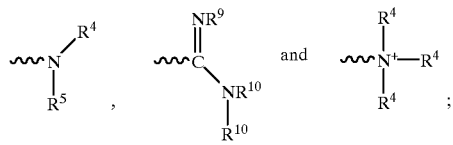

$R^4$ and $R^5$ are independently selected from the group consisting of $R^2$, —C(=NR$^2$)N(R$^2$)$_2$, —C(=NCN)N(R$^2$)$_2$, —C(=NC(O)R$^2$)N(R$^2$)$_2$, C(=NSO$_2$R$^2$)N(R$^2$)$_2$, —C(=NNO$_2$)NR$^2$, heteroaryl, —C(=O)N(R$^2$)$_2$, —C(=S)N(R$^2$)$_2$, —C(=O)R$^2$, 2,2,2-trifluoroethyl, 3,3,3-trifluoropropyl, (CH$_2$)$_t$ cyclopropyl, or $R^4$ and $R^5$ may be taken together to form —(CH$_2$)$_d$—L$_a$(CH$_2$)$_e$— where L$_a$ is —C(R$^2$)$_2$—, —O—, —S(O)$_m$— or —N(R$^2$)—, d and e are independently 1 to 3, said heteroaryl and R$^2$ optionally substituted with 1–3 groups of $C_{1-6}$ alkyl, 1–7 halo, N(R$^2$)$_2$, OR$^2$, N(R$^2$)C(O)R$^2$, C(O)N(R$^2$), OC(O)R$^2$, S(O)$_m$R$^2$, CF$_3$, OCF$_3$, NO$_2$, N(R$^2$)C(O)(R$^2$), N(R$^2$)C(O)N(R$^2$)$_2$, C(O)OR$^2$, C(O)N(R$^2$)$_2$, SO$_2$N(R$^2$)$_2$, N(R$^2$)SO$_2$R$^2$, or methylenedioxy; and the heteroaryl is pyridyl, imidazolyl, pyrimidinyl, thiazolyl or pyrazinyl;

E is selected from the group consisting of —SO$_2$—, —CO(C(R$^2$)$_2$)$_n$—, —C(=N—CN)—, —C(=N—NO$_2$)— and —C(=N—SO$_2$N(R$^2$)$_2$)—;

$R^9$ & $R^{10}$ are independently H, $C_{1-8}$ alkyl or may be taken together to form a $C_{3-8}$ cyclic ring, which can optionally be substituted by 1–5 halogen, OR$^2$ or S(O)$_m$R$^2$;

B is selected from the group consisting of a noncyclic, heterocyclic or heterobicyclic ring selected from the group consisting of

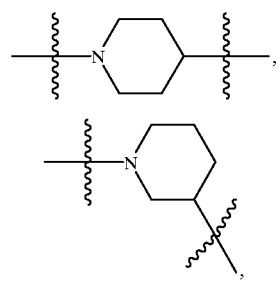

-continued

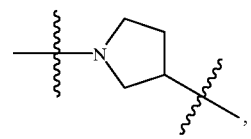

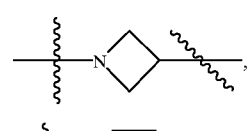

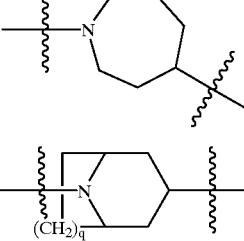

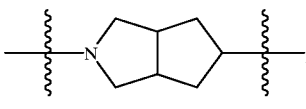

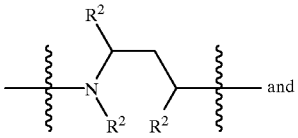 and

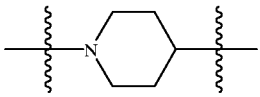

where attachment points are indicated by lines (§) external to the rings and to the open ring which are optionally substituted by $C_1$–$C_6$ alkyl and where R$^2$ and (CH$_2$)$_q$ are described above;

G is N, CH or C=;

Y is —C(O)—, —SO$_2$—, —C(OR$^{11}$)=, —C(SR$^{11}$)=, —C(NR$^{11}$)=, =N—, —N(R$^{11}$)—, =NC(O)—, or —C(R$^{11}$)$_2$—;

X is —N(R$^{11}$)—, =N—, =N—C(R$^{11}$)$_2$—, —N(R$^{11}$)C(R$^{11}$)$_2$—, —O—, —O—C(R$^{11}$)$_2$—, —S—, —S—C(R$^{11}$)$_2$— or C(R$^{11}$)$_2$;

$R^{11}$ is H, $C_1$–$C_8$ alkyl, CF$_3$, CH$_2$CF$_3$, —(CH$_2$)$_p$OR$^2$, —(CH$_2$)$_p$N(R$^2$)$_2$, (CH2)$_p$N(R$^2$)C(O)N(R$^2$)$_2$, —(CH$_2$)$_p$N(R$^2$)C(O)R$^2$, (CH$_2$)$_2$ heteroaryl, (CH$_2$)$_p$N(R$^2$)SO$_2$C$_1$–C$_4$ alkyl, —(CH$_2$)$_p$C(O)N(R$^2$)$_2$, or —(CH$_2$)$_p$C(O)OR$^2$ where heteroaryl is tetrazole, oxadiazole, imidazole or triazole which is optionally substituted with R$^2$, OR$^2$ or N(R$^2$)$_2$ and where p is 0–3;

A is a fused aryl or heteroaryl group 1–4 atoms of which are heteroatoms of N, O and/or S; cycloalkyl; or heterocycloalkyl group, 1–3 atoms of which are heteroatoms N, O and/or S, said aryl, heteroaryl, cycloalkyl or heterocycloalkyl group containing from 5 to 10 atoms and being optionally substituted with 1–3 groups of $C_1$–$C_6$ alkyl, halogen, —OR$^2$, N(R$^2$)$_2$, methylenedioxy, —S(O)$_m$R$^2$, —CF$_3$, —OCF$_3$, nitro, —N(R$^2$)C(O)(R$^2$), —C(O)OR$^2$, —C(O)N(R$^2$)$_2$, -1H-tetrazol-5-yl, —SO$_2$N(R$^2$)$_2$, —N(R$^2$)SO$_2$ phenyl, N(R$^2$)C(O)N(R$^2$) or —N(R$^2$)SO$_2$R$^2$, and in the case where regioisomers are present, all are included;

m is an integer from 0 to 2;

n is an integer from 0 to 3;

q is an integer from 0 to 3; and t is an integer from 0 to 3.

Another group of compounds that is of particular interest relates to compounds of formula Ib:

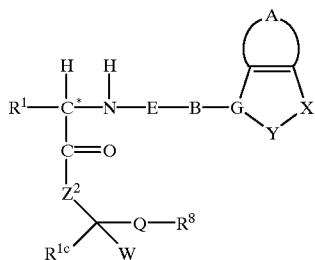

Ib as well as the pharmaceutically acceptable salts thereof, wherein:

$R^1$ is selected from the group consisting of: $C_1$–$C_{10}$ alkyl, aryl, aryl ($C_1$–$C_6$ alkyl), ($C_3$–$C_7$ cycloalkyl)($C_1$–$C_6$ alkyl)—, ($C_1$–$C_5$ alkyl)-K-($C_1$–$C_5$ alkyl)—, aryl($C_0$–$C_5$ alkyl)-K-($C_1$–$C_5$ alkyl)—, and ($C_3$–$C_7$ cycloalkyl)($C_0$–$C_5$ alkyl)-K-($C_1$–$C_5$ alkyl)—, where K is —O—, —S(O)$_m$—, —N($R^2$)C(O)—, —C(O)N($R^2$)—, —$CR^2$=$CR^2$—, or —C∫C—, where $R^2$ and alkyl may be further substituted by 1 to 5 halogen, S(O)$_m R^{2a}$, 1 to 3 of $OR^{2a}$ or C(O)$OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substituent selected from: 1 to 3 of $C_1$–$C_6$ alkyl, 1 to 3 of halogen, 1 to 2 of —$OR^2$, methylenedioxy, —S(O)$_m R^2$, 1 to 2 of —$CF_3$, —$OCF_3$, nitro, —N($R^2$)C(O)($R^2$), —C(O)$OR^2$, —C(O)N($R^2$)($R^2$), -1H-tetrazol-5-yl, —$SO_2$N($R^2$)($R^2$), —N($R^2$)$SO_2$ phenyl, or —N($R^2$)$SO_2R^2$;

$R^2$ is selected from: hydrogen, $C_1$–$C_8$ alkyl, (CH$_2$)$_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^{2a}$ is selected from the group consisting of hydrogen and $C_1$–$C_3$ alkyl, said alkyl optionally substituted by hydroxyl;

$Z^2$ is selected from the group consisting of —O—, —CH$_2$—, —$CHR^{2b}$— and —$NR^{2b}$, when $Z^2$ is $NR^{2b}$ it can optionally be linked to $R^{1c}$, Q and/or W to form a $C_{5-8}$ cyclic ring, which can optionally be interrupted by oxygen, S(O)$_m$ or $NR^{2a}$;

$R^{2b}$ is selected from hydrogen, $C_1$–$C_8$ alkyl, (CH$_2$)$_t$ aryl, —(CH$_2$)$_n CO_2R^2$, —(CH$_2$)$_n$CON($R^2$)$_2$, —(CH$_2$)$_n$OH or —(CH$_2$)$_n OR^2$;

$R^{1c}$ is selected from the group consisting of hydrogen, and $C_1$–$C_8$ alkyl;

W is selected from the group consisting of: hydrogen, $C_1$–$C_8$ alkyl, (CH2)$_t$ aryl, —(CH$_2$)$_q$C(O)$OR^2$, —(CH$_2$)$_q OR^2$, —(CH$_2$)$_q$OC(O)$R^2$, —(CH$_2$)$_q$C(O)$R^2$, —(CH$_2$)$_q$C(O)(CH$_2$)$_t$aryl, —(CH$_2$)$_q$C(O)N($R^2$)$_2$, —(CH$_2$)$_q$N($R^2$)C(O)$R^2$, —(CH$_2$)$_q$N($R^2$)$SO_2R^2$, —(CH$_2$)$_q$N($R^2$)C(O)N($R^2$)$_2$, —(CH$_2$)$_q$OC(O)N($R^2$)$_2$, —(CH$_2$)$_q$N($R^2$)C(O)$OR^2$, —(CH$_2$)$_q$N($R^2$)$SO_2$N($R^2$)$_2$, —(CH$_2$)$_q$S(O)$_m R^2$, and (CH$_2$)$_t$ heteroaryl where the heteroaryl is preferably tetrazole, oxadiazole, thiadiazole, triazole or pyrazine, which is optionally substituted with $R^2$, N($R^2$)$_2$ and $OR^2$, where $R^2$, (CH$_2$)$_q$ and (CH$_2$)$_t$ are optionally substituted with 1 to 2 $C_1$–$C_4$ alkyl, $OR^2$, C(O)$OR^2$, 1–3 halo and said aryl is optionally substituted with 1 to 3 halogen, —$OR^2$, —CON($R^2$)$_2$, —C(O)$OR^2$, $C_1$–$C_4$ alkyl, —S(O)$_m R^2$, N($R^2$)$_2$, $CF_3$ or 1H-tetrazol-5-yl;

Q is selected from the group consisting of:

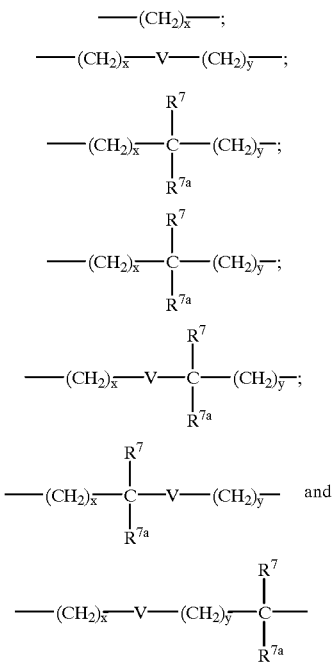

where x and y are independently 0, 1, 2, 3, 4, 5, 6;

V is selected from the group consisting of—N($R^{6a}$)—, —S(O)$_m$—, —O—, —CONR$^2$— and —NR$^2$CO—;

$R^{6a}$ is selected from the group consisting of hydrogen or $C_1$–$C_8$ alkyl, $R^2$CO— and $R^2SO_2$—;

$R^7$ and $R^{7a}$ are independently selected from the group consisting of hydrogen, $C_1$–$C_6$ alkyl, trifluoromethyl and aryl;

R8 is selected from the group consisting of

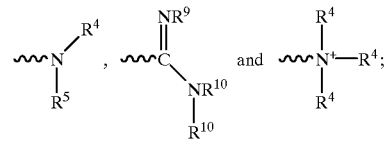

$R^4$ and $R^5$ are independently selected from the group consisting of $R^2$, —C(=N$R^2$)N($R^2$)$_2$, —C(=NCN)N($R^2$)$_2$, —C(=NC(O)$R^2$)N($R^2$)$_2$, C(=N$SO_2R^2$)N($R^2$)$_2$, —C(=S)N($R^2$)$_2$, —C(=NNO$_2$)N$R^2$, heteroaryl, —C(=O)N($R^2$)$_2$, —C(=O)$R^2$, 2,2,2-trifluoroethyl, 3,3,3-trifluoropropyl, (CH$_2$)$_t$ cyclopropyl, or $R^4$ and $R^5$ may be taken together to form —(CH$_2$)$_d$—L$_a$(CH$_2$)$_e$— where L$_a$ is —C($R^2$)$_2$—, —O—, —S(O)$_m$— or —N($R^2$)—, d and e are independently 1 to 3, said heteroaryl and $R^2$ optionally substituted with 1–3 groups of $C_{1-6}$ alkyl, 1–7 halo, N($R^2$)$_2$, $OR^2$, N($R^2$)C(O)$R^2$, C(O)N($R^2$), OC(O)$R^2$, S(O)$_m R^2$, $CF_3$, $OCF_3$, $NO_2$, N($R^2$)C(O)($R^2$), N($R^2$)C(O)N($R^2$)$_2$, C(O)$OR^2$, C(O)N($R^2$)$_2$, $SO_2$N($R^2$)$_2$, N($R^2$)$SO_2R^2$, or methylenedioxy; and the heteroaryl is pyridyl, imidazolyl, pyrimidinyl, thiazolyl or pyrazinyl;

E is selected from the group consisting of —$SO_2$—, —CO(C($R^2$)$_2$)$_n$—, —C(=N—CN)—, —C(=N—NO$_2$)— and —C(=N—$SO_2$N($R^2$)$_2$)—;

$R^9$ and $R^{10}$ are independently H, $C_{1-8}$ alkyl or may be taken together to form a C3–8 cyclic ring, which can optionally be substituted by 1–5 halogen, $OR^2$ or S(O)$_m R^2$;

B is selected from the group consisting of a noncyclic or heterocyclic selected from the group consisting of

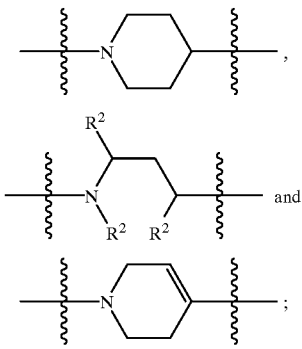

where attachment points are indicated by lines

external to the rings and to the open ring which are optionally substituted by $C_1-C_6$ alkyl and where $R^2$ and $(CH_2)_q$ are described above;

G is N, CH or C=;

Y is —C(O)—, —SO$_2$—, —C(OR$^{11}$)=, —C(SR$^{11}$)=, —C(NR$^{11}$)=, =N—, —N(R$^{11}$)—, =NC(O)—, or —C(R$^{11}$)$_2$—;

X is —N(R$^{11}$)—, =N—, =N—C(R$^{11}$)$_2$—, —N(R$^{11}$)C(R$^{11}$)$_2$—, —O—, —O—C(R$^{11}$)$_2$—, —S—, —S—C(R$^{11}$)$_2$— or C(R$^{11}$)$_2$;

$R^{11}$ is H, $C_1-C_8$ alkyl, $CF_3$, $CH_2CF_3$, —(CH$_2$)$_p$OR$^2$, —(CH$_2$)$_p$N(R$^2$)$_2$, (CH2)$_p$N(R$^2$)C(O)N(R$^2$)$_2$, —(CH$_2$)$_p$N (R$^2$)C(O)R$^2$, (CH$_2$)$_2$ heteroaryl, (CH$_2$)$_p$N(R$^2$)SO$_2$C$_1$-C$_4$ alkyl, —(CH$_2$)$_p$C(O)N(R$^2$)$_2$, or —(CH$_2$)$_p$C(O)OR$^2$ where heteroaryl is tetrazole, oxadiazole, imidazole or triazole which is optionally substituted with $R^2$, $OR^2$ or $N(R^2)_2$ and where p is 0–3;

A is a fused aryl or heteroaryl group 1–4 atoms of which are heteroatoms of N, O and/or S; cycloalkyil; or heterocycloalkyl group, 1–3 atoms of which are heteroatoms N, O and/or S, said aryl, heteroaryl, cycloalkyl or heterocycloalkyl group containing from 5 to 10 atoms and being optionally substituted with 1–3 groups of $C_1-C_6$ alkyl, halogen, —OR$^2$, N(R$^2$)$_2$, methylenedioxy, —S(O)$_m$R$^2$, —CF$_3$, —OCF$_3$, nitro, —N(R$^2$)C(O)(R$^2$), —C(O)OR$^2$, —C(O)N(R$^2$)$_2$, -1H-tetrazol-5-yl, —SO$_2$N(R$^2$)$_2$, —N(R$^2$)SO$_2$ phenyl, N(R$^2$)C(O)N(R$^2$) or —N(R$^2$)SO$_2$R$^2$, and in the case where regioisomers are present, all are included;

m is an integer from 0 to 2;

n is an integer from 0 to 3;

q is an integer from 0 to 3; and t is an integer from 0 to 3.

Another subset of compounds that is of particular interest relates to compounds of formula Ic:

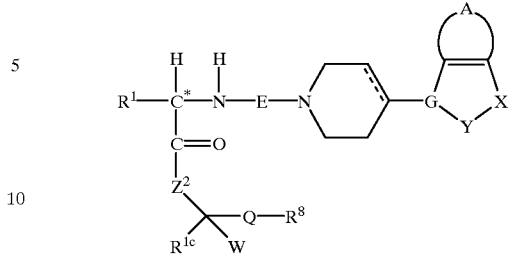

as well as pharmaceutically acceptable salts thereof, wherein:

$R^1$ is selected from the group consisting of: $C_1-C_{10}$ alkyl, aryl, aryl ($C_1-C_6$ alkyl), ($C_3-C_7$ cycloalkyl)($C_1-C_6$ alkyl)—, ($C_1-C_5$ alkyl)—O—($C_1-C_5$ alkyl)—, and aryl ($C_0-C_5$ alkyl)—O—($C_1-C_5$ alkyl)—, where $R^2$ and alkyl may be further substituted by 1 to 5 halogen, $S(O)_mR^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1-C_6$ alkyl, 1 to 3 of halogen, 1 to 2 of —OR$^2$, methylenedioxy, —SO)$_m$R$^2$, 1 to 2 of —CF$_3$, —OCF$_3$, nitro, —N(R$^2$)C(O) (R$^2$), —C(O)OR$^2$, —C(O)N(R$^2$)(R$^2$), -1H-tetrazol-5-yl, —SO$_2$N(R$^2$)(R$^2$), —N(R$^2$)SO$_2$ phenyl, or —N(R$^2$)SO$_2$R$^2$;

$R^2$ is selected from: hydrogen, $C_1-C_8$ alkyl, (CH$_2$)$_t$ aryl, and $C_3-C_7$ cycloalkyl, and where two $C_1-C_6$ alkyl groups are present on one atom, they optionally are joined to form a $C_3-C_8$ cyclic ring, optionally including oxygen, sulfur or NR$^{3a}$, where $R^{3a}$ is hydrogen, or $C_1-C_6$ alkyl, optionally substituted by hydroxyl;

$R^{2a}$ is selected from the group consisting of hydrogen and $C_1-C_3$ alkyl, said alkyl optionally substituted by hydroxyl;

$Z^2$ is selected from the group consisting of —O—, —CH2—, —CHR$^{2b}$— and —NR$^{2b}$, when $Z^2$ is NR$^{2b}$ it can optionally be linked to $R^{1c}$, Q and/or W to form a $C_{5-8}$ cyclic ring;

$R^{2b}$ is selected from hydrogen, $C_1-C_8$ alkyl, (CH$_2$)$_t$ aryl, —(CH$_2$)$_n$CO$_2$R$^2$, —(CH$_2$)$_n$CON(R$^2$)$_2$, —(CH$_2$)$_n$OH or —(CH$_2$)$_n$OR$^2$;

$R^{1c}$ is selected from the group consisting of hydrogen and $C_1-C_8$ alkyl;

W is selected from the group consisting of: hydrogen, $C_1-C_8$ alkyl, (CH2)$_t$ aryl, —(CH$_2$)$_q$C(O)OR$^2$, —(CH$_2$)$_q$ OR$^2$, —(CH$_2$)$_q$OC(O)R$^2$, —(CH$_2$)$_q$C(O)R$^2$, —(CH$_2$)$_q$C(O) (CH$_2$)$_t$aryl, —(CH$_2$)$_q$C(O)N(R$^2$)$_2$, —(CH$_2$)$_q$N(R$^2$)C(O)R$^2$, —(CH$_2$)$_q$N(R$^2$)SO$_2$R$^2$, —(CH$_2$)$_q$N(R$^2$)C(O)N(R$^2$)$_2$, —(CH$_2$)$_q$OC(O)N(R$^2$)$_2$, —(CH$_2$)$_q$N(R$^2$)C(O)OR$^2$, —(CH$_2$)$_q$ N(R$^2$)SO$_2$N(R$^2$)$_2$, —(CH$_2$)$_q$S(O)$_m$R$^2$, and (CH$_2$)$_t$ heteroaryl where the heteroaryl is preferably tetrazole, oxadiazole, thiadiazole, triazole or pyrazine, which is optionally substituted with $R^2$, $N(R^2)_2$ and $OR^2$, where $R^2$, (CH$_2$)$_q$ and (CH$_2$)$_t$ are optionally substituted with 1 to 2 $C_1-C_4$ alkyl, OR$^2$, C(O)OR$^2$, 1–3 halo and said aryl is optionally substituted with 1 to 3 halogen, —OR$^2$, —CON (R$^2$)$_2$, —C(O)OR$^2$, $C_1-C_4$ alkyl, —S(O)$_m$R$^2$, N(R$^2$)$_2$, CF$_3$ or 1H-tetrazol-5-yl;

Q is selected from the group consisting of:

—(CH$_2$)$_{\overline{x}}$— ; —(CH$_2$)$_{\overline{x}}$—V—(CH$_2$)$_{\overline{y}}$— ;

-continued

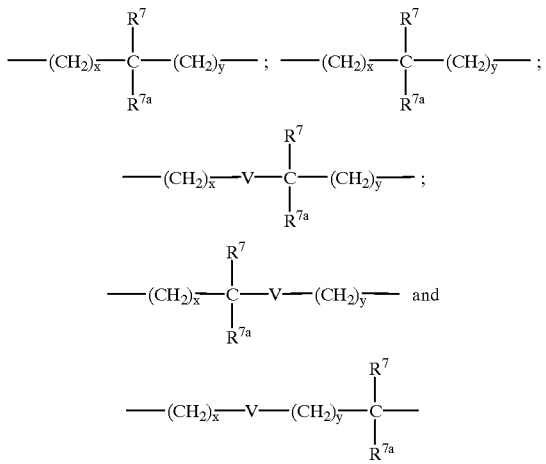

where x and y are independently 0, 1, 2, 3, 4, 5, 6;

V is selected from the group consisting of —N(R$^{6a}$)—, —S(O)$_m$—, —O—, —CONR$^2$— and —NR$^2$CO—;

R$^{6a}$ is selected from the group consisting of hydrogen or C$_1$–C$_8$ alkyl, R$^2$CO— and R$^2$SO$_2$—;

R$^7$ and R$^{7a}$ are independently selected from the group consisting of hydrogen, C$_1$–C$_6$ alkyl, trifluoromethyl and aryl;

R8 is selected from the group consisting of

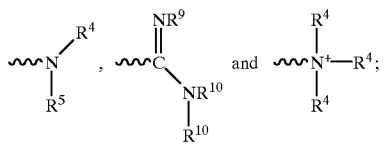

R$^4$ and R$^5$ are independently selected from the group consisting of R$^2$, —C(=NR$^2$)N(R$^2$)$_2$, —C(=NCN)N(R$^2$)$_2$, —C(=S)N(R$^2$)$_2$, —C(=NC(O)R$^2$)N(R$^2$)$_2$, C(=NSO$_2$R$^2$) N(R$^2$)$_2$, —C(=NNO$_2$)NR$^2$, heteroaryl, —C(=O)N(R$^2$)$_2$, —C(=O)R$^2$, 2,2,2-trifluoroethyl, 3,3,3-trifluoropropyl, (CH$_2$)$_t$ cyclopropyl, or R$^4$ and R$^5$ may be taken together to form —(CH$_2$)$_d$—L$_a$(CH$_2$)$_e$— where L$_a$ is —C(R$^2$)$_2$—, —O—, —S(O)$_m$— or —N(R$^2$)—, d and e are independently 1 to 3, said heteroaryl and R$^2$ optionally substituted with 1–3 groups of C$_{1-6}$ alkyl, 1–7 halo, N(R$^2$)$_2$, OR$^2$, N(R$^2$)C(O)R$^2$, C(O)N(R$^2$), OC(O)R$^2$, S(O)$_m$R$^2$, CF$_3$, OCF$_3$, NO$_2$, N(R$^2$)C (O)(R$^2$), N(R$^2$)C(O)N(R$^2$)$_2$, C(O)OR$^2$, C(O)N(R$^2$)$_2$, SO$_2$N (R$^2$)$_2$, N(R$^2$)SO$_2$R$^2$, or methylenedioxy; and the heteroaryl is pyridyl, imidazolyl;

E is selected from the group consisting of —SO$_2$—, —CO—, —C(=N—CN)—, —C(=N—NO$_2$)— and —C(=N—SO$_2$NH$_2$)—;

R$^9$ and R$^{10}$ are independently H or C$_{1-8}$ alkyl;

G is N, CH or C=;

Y is —C(O)—, —SO$_2$—, —C(OR$^{11}$)=, —C(SR$^{11}$)=, —C(NR$^{11}$)=, =N—, —N(R$^{11}$)—, =NC(O)—, or —C(R$^{11}$)$_2$—;

X is —N(R$^{11}$)—, =N—, =N—C(R$^{11}$)$_2$—, —N(R$^{11}$)C (R$^{11}$)$_2$—, —O—, —O—C(R$^{11}$)$_2$—, —S—, —S—C(R$^{11}$)$_2$— or C(R$^{11}$)$_2$;

R$^{11}$ is H, C$_1$–C$_8$ alkyl, CF$_3$, CH$_2$CF$_3$, —(CH$_2$)$_p$OR$^2$, —(CH$_2$)$_p$N(R$^2$)$_2$, (CH2)$_p$N(R$^2$)C(O)N(R$^2$)$_2$, —(CH$_2$)$_p$N (R$^2$)C(O)R$^2$, (CH$_2$)$_2$-heteroaryl, (CH$_2$)$_p$N(R$^2$)SO$_2$C$_1$–C$_4$ alkyl, —(CH$_2$)$_p$C(O)N(R$^2$)$_2$ or —(CH$_2$)$_p$C(O)OR$^2$ where heteroaryl is tetrazole, oxadiazole, imidazole or triazole which is optionally substituted with R$^2$, OR$^2$ or N(R$^2$)$_2$ and where p is 0–3;

A is a fused aryl or heteroaryl group 1–4 atoms of which are heteroatoms of N, O and/or S; cycloalkyl; or heterocycloalkyl group, 1–3 atoms of which are heteroatomseteroatoms N, O and/or S, said aryl, heteroaryl, cycloalkyl or heterocycloalkyl group containing from 5 to 10 atoms and being optionally substituted with 1–3 groups of C$_1$–C$_6$ alkyl, halogen, —OR$^2$, N(R$^2$)$_2$, methylenedioxy, —S(O)$_m$R$^2$, —CF$_3$, —OCF$_3$, nitro, —N(R$^2$)C(O)(R$^2$), —C(O)OR$^2$, —C(O)N(R$^2$)$_2$, -1H-tetrazol-5-yl, —SO$_2$N(R$^2$)$_2$, —N(R$^2$) SO$_2$ phenyl, N(R$^2$)C(O)N(R$^2$) or —N(R$^2$)SO$_2$R$^2$, and in the case where regioisomers are present, all are included;

m is an integer from 0 to 2;
n is an integer from 0 to 3;
q is an integer from 0 to 3; and
t is an integer from 0 to 3.

Yet another subset of compounds that is of particular interest relates to compounds of formula Id:

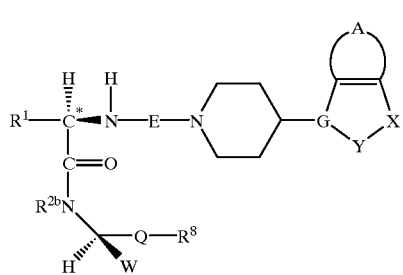

as well as pharmaceutically acceptable salts thereof, wherein R$^1$ is selected from the group consisting of:

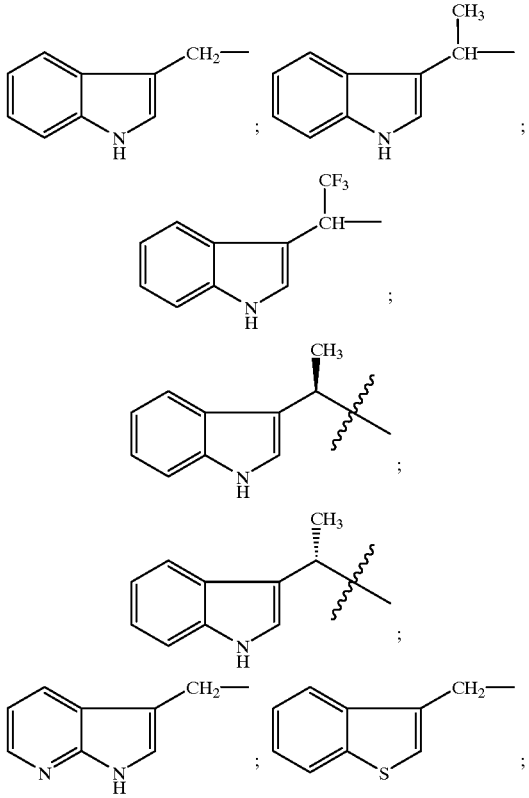

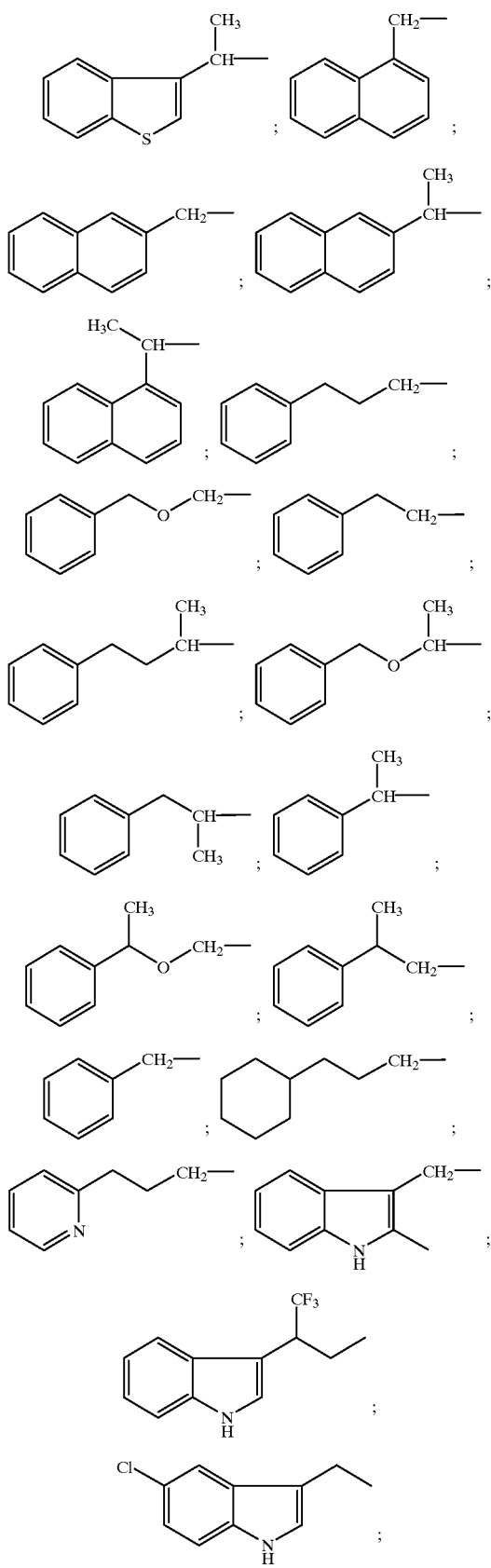
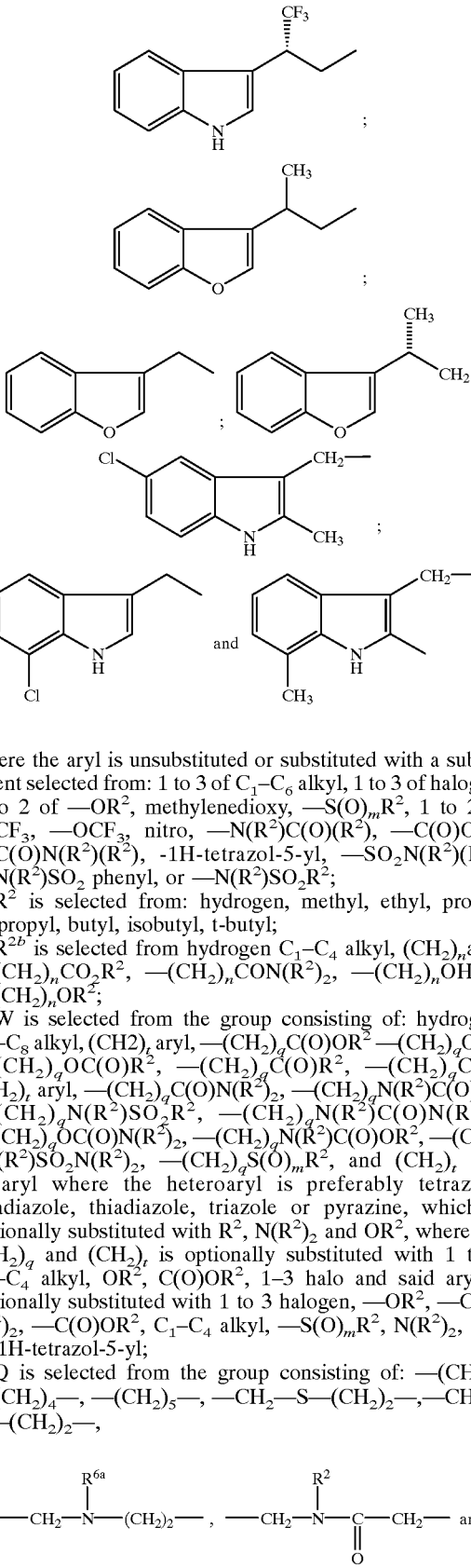

where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_m R^2$, 1 to 2 of —$CF_3$, —$OCF_3$, nitro, —$N(R^2)C(O)(R^2)$, —$C(O)OR^2$, —$C(O)N(R^2)(R^2)$, -1H-tetrazol-5-yl, —$SO_2N(R^2)(R^2)$, —$N(R^2)SO_2$ phenyl, or —$N(R^2)SO_2R^2$;

$R^2$ is selected from: hydrogen, methyl, ethyl, propyl, isopropyl, butyl, isobutyl, t-butyl;

$R^{2b}$ is selected from hydrogen $C_1$–$C_4$ alkyl, $(CH_2)_n$ aryl, —$(CH_2)_n CO_2 R^2$, —$(CH_2)_n CON(R^2)_2$, —$(CH_2)_n OH$ or —$(CH_2)_n OR^2$;

W is selected from the group consisting of: hydrogen, $C_1$–$C_8$ alkyl, $(CH2)_t$ aryl, —$(CH_2)_q C(O)OR^2$ —$(CH_2)_q OR^2$, —$(CH_2)_q OC(O)R^2$, —$(CH_2)_q C(O)R^2$, —$(CH_2)_q C(O)(CH_2)_t$ aryl, —$(CH_2)_q C(O)N(R^2)_2$, —$(CH_2)_q N(R^2)C(O)R^2$, —$(CH_2)_q N(R^2)SO_2 R^2$, —$(CH_2)_q N(R^2)C(O)N(R^2)_2$, —$(CH_2)_q OC(O)N(R^2)_2$, —$(CH_2)_q N(R^2)C(O)OR^2$, —$(CH_2)_q N(R^2)SO_2 N(R^2)_2$, —$(CH_2)_q S(O)_m R^2$, and $(CH_2)_t$ heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ is optionally substituted with 1 to 2 $C_1$–$C_4$ alkyl, $OR^2$, $C(O)OR^2$, 1–3 halo and said aryl is optionally substituted with 1 to 3 halogen, —$OR^2$, —$CON(R^2)_2$, —$C(O)OR^2$, $C_1$–$C_4$ alkyl, —$S(O)_m R^2$, $N(R^2)_2$, $CF_3$ or 1H-tetrazol-5-yl;

Q is selected from the group consisting of: —$(CH_2)_3$, —$(CH_2)_4$—, —$(CH_2)_5$—, —$CH_2$—S—$(CH_2)_2$—,—$CH_2$—O—$(CH_2)_2$—,

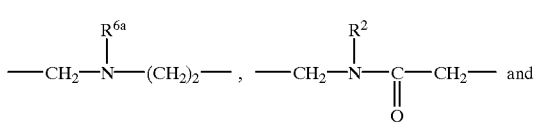

-continued

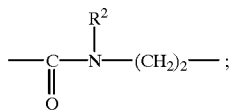

$R^{6a}$ is selected from the group consisting of hydrogen or $C_1-C_8$ alkyl, $R^2CO—$ and $R^2SO_2—$;

R8 is

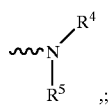

$R^4$ and $R^5$ are independently selected from the group consisting of $R^2$, —C(=NR$^2$)N(R$^2$)$_2$, heteroaryl,—C(=S)N(R$^2$)$_2$, —C(=O)N(R$^2$)$_2$, —C(=O)R$^2$, 2,2,2-trifluoroethyl, 3,3,3-trifluoropropyl, (CH$_2$)$_t$ cyclopropyl, and the heteroaryl is pyridyl or imidazolyl;

E is selected from the group consisting of —CO—, —C(=N—CN)—, and —SO$_2$—;

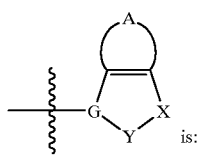
is:

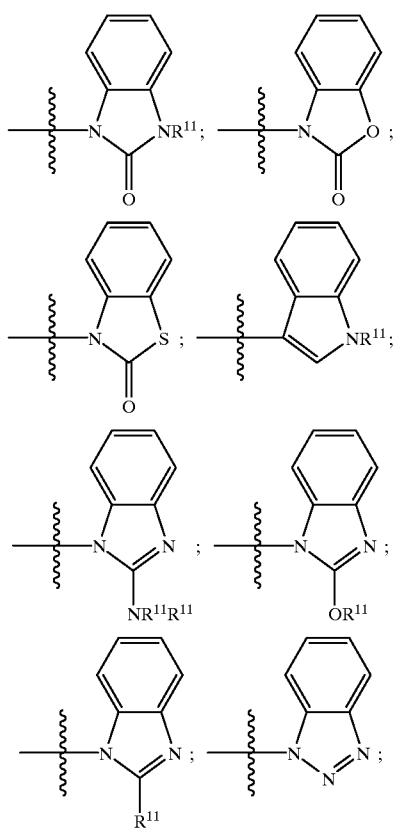

-continued

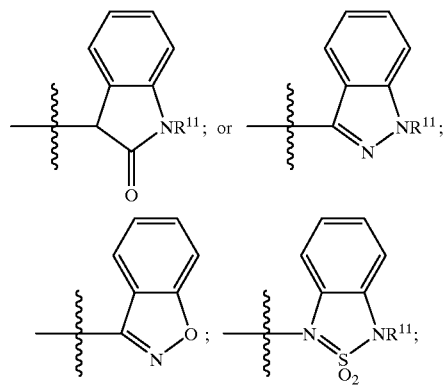

where the aromatic can be optionally substituted with 1–3 groups of $C-C_6$ alkyl, halogen, —OR$^2$, N(R$^2$)$_2$, methylenedioxy, —S(O)$_m$R$^2$, —CF$_3$, —OCF$_3$, nitro, —N(R$^2$)C(O)(R$^2$), —C(O)OR$^2$, —C(O)N(R$^2$)$_2$, -1H-tetrazol-5-yl, —SO$_2$N(R$^2$)$_2$, —N(R$^2$)SO$_2$ phenyl, N(R$^2$)C(O)N(R$^2$) or —N(R$^2$)SO$_2$R$^2$;

$R^{11}$ is H, $C_1-C_8$ alkyl, CF$_3$, CH$_2$CF$_3$, —(CH$_2$)$_p$OR$^2$, —(CH$_2$)$_p$N(R$^2$)$_2$, (CH2)$_p$N(R$^2$)C(O)N(R$^2$)$_2$, —(CH$_2$)$_p$N(R$^2$)C(O)R$^2$, (CH$_2$)$_p$ heteroaryl, (CH$_2$)$_p$N(R$^2$)SO$_2$C$_1$-C$_4$ alkyl, —(CH$_2$)$_p$C(O)N(R$^2$)$_2$, or —(CH$_2$)$_p$C(O)OR$^2$ where heteroaryl is tetrazole, oxadiazole, imidazole or triazole which is optionally substituted with R$^2$, OR$^2$ or N(R$^2$)$_2$ and where p is 0–3;

m is an integer from 0 to 2;

n is an integer from 0 to 3;

q is an integer from 0 to 3 and t is an integer from 0 to 3.

Another subset of compounds that is of particular interest is defined in accordance with formula Ie:

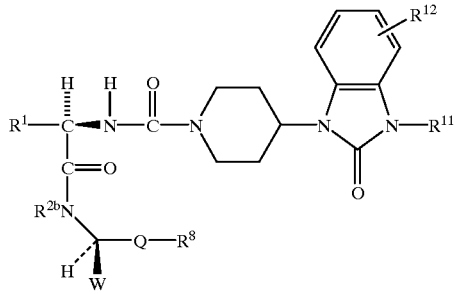

as well as pharmaceutically acceptable salts thereof, wherein:

$R^1$ is selected from the group consisting of:

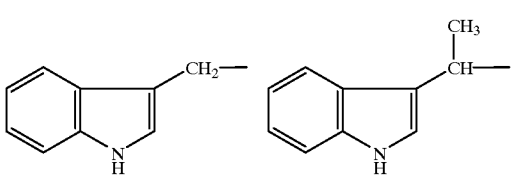

-continued

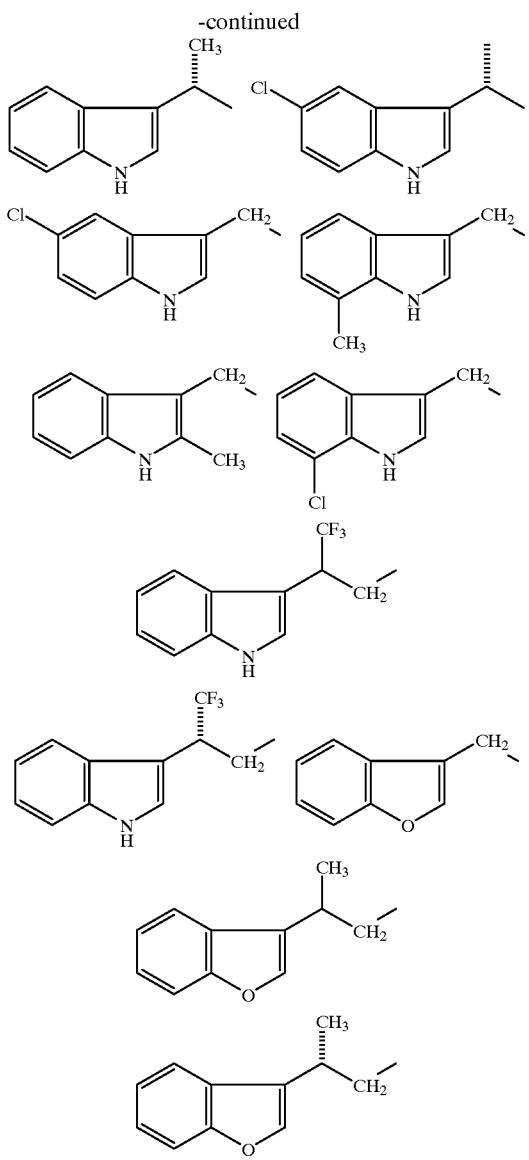

wherein the aryl groups shown above may be further substituted by 1 to 3 of $C_1$–$C_6$ alkyl, 1 to 3 of halogen, 1 to 2 of $OR^2$, $S(O)_mR^2$, or 1 to 2 of $CF_3$;

$R^2$ is selected from hydrogen or $C_1$–$C_6$ alkyl;

$R^{2b}$ is selected from hydrogen, $C_1$–$C_4$ alkyl, $(CH_2)_n$ phenyl or $(CH_2)_n$—$OR^2$;

W is selected from the group consisting of hydrogen, $C_1$–$C_4$ alkyl, $(CH_2)_2OR^2$, $(CH_2)_qC(O)N(R^2)_2$, $(CH_2)_qC(O)OR_2$ or oxadiazole optionally substituted by $R^2$, $N(R^2)_2$ or $OR^2$;

Q is selected from the group consisting of —$(CH_2)_3$—, —$(CH_2)_4$—, —$(CH_2)_5$—, —$CH_2S$—$(CH_2)_2$— or —$CH_2O$—$(CH_2)_2$—

$R^8$ is

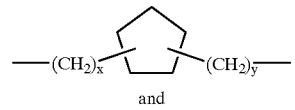 and 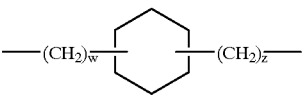

wherein $R^4$ and $R^5$ are independently selected from the group consisting of $R^2$, —$C(=NR^2)N(R^2)_2$, 2,2,2-trifluoroethyl or —$CH_2CH_2$—$OR^2$; and $R^{1a}$ is H or $C_{1-3}$ alkyl;

$R^{11}$ is hydrogen, $R^2$, $CF_3$, $CH_2CF_3$ or $CH_2CH_2OR_2$;

$R^{12}$ is hydrogen, 1–2 $R^2$, 1–2 halogen, 1–2 $OR^2$ or 1–2 $CF_3$;

n is 0, 1 or 2 and q is 0 or 1.

Also included in the invention is a pharmaceutical composition which is comprised of a compound of formula I in combination with a pharmaceutically acceptable carrier.

The invention also includes a method of treating diabetes, cancer, acromegaly chronic atrophic gastritis, Crohn's disease, ulcerative colitis, retinopathy, arthritis, viseral and neuropathic pain and to prevent restenosis, which comprises administering to a person or animal a compound of formula I in an amount which is effective for treating said disease or condition.

The invention is described herein in detail using the terms defined below unless otherwise specified.

The term "alkyl" refers to a monovalent alkane (hydrocarbon) derived radical containing from 1 to 15 carbon atoms unless otherwise defined and if two carbon atoms or more they may include a double or a triple bond. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

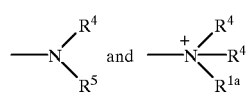

and

—$(CH_2)_w$— ⬡ —$(CH_2)_z$— wherein: x plus y=from 0–10 and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

Aryl refers to aromatic rings e.g., phenyl, substituted phenyl and like groups as well as rings which are fused, e.g., naphthyl, indaryl, biphenyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with from 1 to 3 groups of $C_1$–$C_{15}$ alkyl, halogen, —$OR^2$, methylenedioxy, —$S(O)_m R^2$, —$CF_3$, —$OCF_3$, nitro, —$N(R^2)C(O)(R^2)$, —$C(O)OR^2$, —$C(O)N(R^2)_2$, -1H-tetrazol-5-yl, —$SO_2N(R^2)_2$, —$N(R^2)SO_2$ phenyl or —$N(R^2)SO_2R^2$. Preferred substituted aryls include phenyl and naphthyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups selected from 1 to 3 of $C_1$–$C_8$ alkyl, halogen, —$OR^2$, methylenedioxy, —$S(O)_m R^2$, —$CF_3$, —$OCF_3$, $N(R^2)_2$, nitro, —$N(R^2)C(O)(R^2)$, —$C(O)OR^2$, —$C(O)N(R^2)_2$, -1H-tetrazol-5-yl, —$SO_2N(R^2)_2$, —$N(R^2)SO_2$ phenyl or —$N(R^2)SO_2R^2$.

Heteroaryl thus includes aromatic and partially aromatic groups which contain one or more heteroatoms. Examples of this type are thiophene, oxadiazole, imidazopyridine, pyridine, oxazole, thiazole, pyrazole, tetrazole, imidazole, pyrimidine, pyrazine, benzothienyl, benzofuranyl, indolyl, azaindole, benzimidazolyl, quinolinyl, isoquinolinyl and triazine.

The terms "heterocycloalkyl" and "heterocyclyl" refer to a cycloalkyl group (nonaromatic) in which one of the carbon atoms in the ring is replaced by a heteroatom selected from O, S, SO, $SO_2$ or N, and in which up to three additional carbon atoms may be optionally replaced by heteroatoms.

Heterocyclyl is carbon or nitrogen linked; if carbon linked and contains a nitrogen, then the nitrogen may be substituted by $R^2$. Examples of heterocyclyls are piperidinyl, morpholinyl, pyrrolidinyl, tetrahydrofuranyl, tetrahydroimidazo[4,5-c]pyridinyl, imidazolinyl, piperazinyl, pyrolidin-2-onyl, piperidin-2-onyl and the like.

Certain of the above defined terms may occur more than once in the above formula and upon such occurrence each term shall be defined independently of the other.

Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Camsylate, Carbonate, Citrate, Dihydrochloride, Edetate, Edisylate, Estolate, Esylate, Fumarate, Gluconate, Glutamate, Hydrobromide, Hydrochloride, Hydroxynaphthoate, Lactate, Lactobionate, Laurate, Malate, Maleate, Mandelate, Mesylate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Tosylate, and Valerate.

The compounds of the present invention may contain one or more asymmetric carbon atoms and may exist in racemic and optically active forms. All of these compounds are contemplated to be within the scope of the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric carbon atom represented by an asterisk in Formula I, it has been found that compounds are more active as somatostatin agonists and, therefore preferred, in which the nitrogen substituent is above and the $R^{1a}$ is below the plane of the structure as represented. An equivalent representation places $R^1$ and the N-substitutent in the plane of the structure with the C=O group above. This configuration corresponds to that present in a D-amino acid. In most cases, this is also designated an R-configuration, although this will vary according to the value of $R^1$ used in making R- or S- stereochemical assignments. In addition, configurations of some of the most preferred compounds of this invention are indicated. When the carbon atom in Formula I bearing an asterisk is of a defined and usually a D-configuration, up to two times more diastereomers result with each additional stereo centers are present. These diastereomers are arbitrarily referred to as diastereomer 1 ($d_1$) and diastereomer 2 ($d_2$) and so on as so forth in this invention and, if desired, their independent syntheses or chromatographic separations may be achieved as described herein. Their absolute stereochemistry may be determined by the x-ray crystallography of crystalline products or crystalline intermediates which are derivatized, if necessary, with a reagent containing an asymmetric center of known absolute configuration.

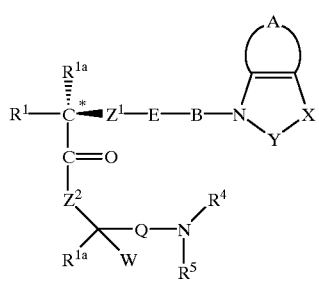

II

The term "pharmacologically effective amount" shall mean that amount of the drug or pharmaceutical agent that elicits the biological or medical response of a tissue, system, animal or human that is being sought by a researcher or clinician.

The term "substituted" shall be deemed to include multiple degrees of substitution by a named substituent.

Where multiple substituent moieties are disclosed or claimed, the substituted compound can be independently substituted by one or more of the disclosed or claimed substituent moieties, singly or plurally.

The ability of the compounds of the present invention to act as somatostatin agonists makes them useful as pharmacologic agents for mammals, especially for humans, for the treatment and prevention of disorders wherein somatostatin itself or the hormones it regulates may be involved. Examples of such disorders have been noted earlier and include diabetes, acromegaly, neuropathic pain, restenosis, arthritis and cancer. The instant compounds can also be used in combination with other therapeutic agents. For example, for diabetes treatment these agents include metformin or other biguanides, acarbose, sulfonylureas, thiazolidinediones or other insulin sensitizers including, but not limited to, compounds which function as agonists on peroxisome proliferator-activated receptor gamma (PPAR-gamma), insulin, insulin-like-growth factor I, glucagon-like peptide I (glp-I) and satiety-promoting agents such as dexfenfluramine.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Intravenous dosages or oral dosages of the compounds of the present invention, when used for the indicated effects, will range between about 0.001 to 5 mg/kg and 0.1 to 50 mg/kg, respectively. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris/dimethylamino)-phosphonium hexafluorophosphate |
| calc. | calculated |
| CBZ, Cbz | Benzyloxycarbonyl |
| CDI | N,N'-carbonyl diimidazole |
| DCC | Dicyclohexylcarbodiimide |
| DCM | dichloromethane |
| DIEA | diisopropylethylamine |
| DMF | N,N-dimethylformamide |
| DMAP | 4-Dimethylaminopyridine |
| DSC | N,N'-disuccinimidyl carbonate |
| EDC | 1-(3-dimethylaminopropyl)-3-ethylcarbodi-imide hydrochloride |
| EI-MS | Electron ion-mass spectroscopy |
| Et | ethyl |
| EtOAc | ethyl acetate |
| EtOH | ethanol |
| eq. | equivalent(s) |
| FAB-MS | Fast atom bombardment-mass spectroscopy |
| HOAc | acetic acid |
| HOBT, HOBt | Hydroxybenztriazole |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |
| Me | methyl |
| MeOH | methanol |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Trimethylsilane |

The instant compounds can be effective to inhibit the secretion of various hormones and trophic factors in mammals. They may be used to suppress certain endocrine secretions, such as GH, insulin, glucagon and prolactin, in the treatment of disorders such as acromegaly; endocrine tumors such as carcinoids, vipomas, insulinomas and glucagonomas; or diabetes and diabetes-related pathologies, including retinopathy, neuropathy and nephropathy. The compounds may also be used to suppress exocrine secretions in the pancreas, stomach and intestines, for treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the instant compounds include cancers of the breast, prostate, and lung (both small cell and non-small cell epidermoids), as well as hepatomas, neuroblastomas, colon and pancreatic adenocarcinomas (ductal type), chondrosarcomas, and melanomas, and also atherosclerosis associated with vascular grafts and restenosis following angioplasty. Somastostatin in the brain inhibits the neuronal release of substance P(NK-1) and NK-1 antagonists have been shown to have a marked use as an antidepressant agent. Accordingly, the instant compounds are also useful in treating depression.

The compounds of the instant invention are further useful to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; and allergies, including asthma. The compounds can also function as neuromodulators in the central nervous system, with useful applications in the treatment of Alzheimer's disease and other forms of dementia, pain (including neuropathic and visceral pain) and headaches. Furthermore, in disorders involving the splanchnic blood flow, including cirrhosis and oesophagal varices, the compounds of the invention can provide cytoprotection.

The preparation of compounds of Formula I of the present invention may be carried out in sequential or convergent synthetic routes. In the interest of clarity, the special case of Formula I, where B is 4-piperidinyl and A is a fused benzo ring as being unsubstituted (formula IIA), is depicted. Compounds fused with different aromatic or non aromatic rings and/or bearing additional substituents on these rings are readily prepared by minor modification of the methods herein with procedures known in the art. Syntheses detailing the preparation of the compounds of Formula I are presented in the following reaction schemes.

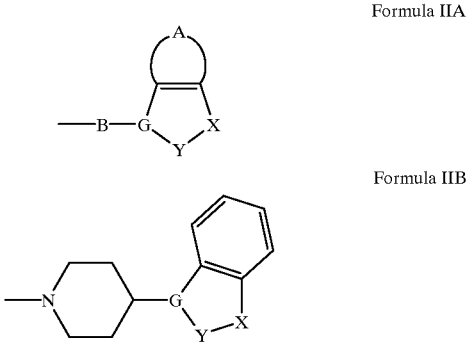

Formula IIA

Formula IIB

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The phrase "mixed urea formation" refers to conversion of two different amines to form their mixed urea by using phosgene or equivalents such as CDI, DSC, or p-nitrophenyl chloroformate. The reaction involves reacting one amine first with the phosgene or equivalents in the presence of a base such as NMM, TEA or DIEA in a inert solvent such as dichloromethane, THF and DMF or mixtures thereof, followed by addition of the second amine and a base such as NMM, TEA or DIEA. The uses of protective groups for amines and carboxylic acids to facilitate the desired reaction and minimize undesired reactions are well documented. Conditions required to remove protecting groups which may be present can be found in Greene, T, and Wuts, P. G. M., *Protective Groups in Organic Synthesis,* John Wiley & Sons, Inc., New York, N.Y. 1991. CBZ and BOC were used extensively and their removal conditions are known to those skilled in the art. For example, removal of CBZ groups can be achieved by a number of methods such as catalytic hydrogenation in the presence of a noble metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethyl sulfide. Removal of BOC protecting groups is carried out in a solvent such as methylene chloride, methanol or ethyl acetate, with a strong acid, such as trifluoroacetic acid, hydrochloric acid or hydrogen chloride gas.

The protected amino acid derivatives required in the synthesis of compounds of Formula 1 are, in many cases, commercially available, where the protecting group ($P^1$) is, for example, methyl, allyl or benzyl groups. Other protected amino acid can be prepared by literature methods (Williams, R. M. *Synthesis of Optically Active α-Amino Acids,* Pergamon Press: Oxford, 1989). Many of the piperidines of Formula 2 are either commercially available or known in the literature and others can be prepared following literature methods described for analogous compounds. Some of these methods are illustrated in the subsequent schemes. Purification procedures include crystallization, normal phase or reverse phase chromatography.

The compounds of the present invention can be prepared readily according to the following Schemes or modifications thereof using readily available starting materials, reagents and conventional synthesis procedures. In these reactions, it is also possible to make use of variants which are themselves known to those of ordinary skill in this art, but are not mentioned in greater detail. The definition for $R^1$, $R^{1a}$, $R^2$, $R^4$, $R^5$, G, Y, X, $Z^1$, $Z^2$, W, Q, E, B, etc., is described above unless otherwise stated.

SCHEME 1

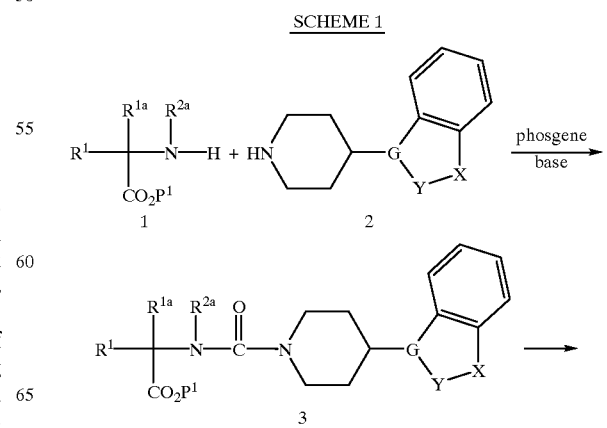

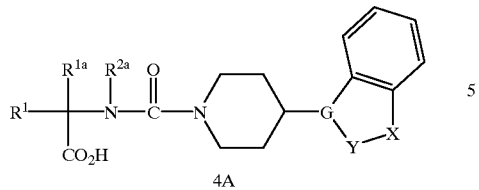

Intermediates of Formula 4A can be synthesized as described in Scheme 1. Mixed urea formation between the protected amino acid 1 and the piperidine of Formula 2, is conveniently carried out under usual urea formation reactions use phosgene or equivalents such as CDI, DSC, or p-nitrophenyl chloroformate. Removal of the $P^1$ protecting group can be achieved by saponification for most esters, or by catalytic hydrogenolysis when $P^1$ is benzyl, or by palladium (0) based homogeneous catalysis when $P^1$ is allyl. Intermediate 4A can be used as a common intermediate for the synthesis of somatostatin agonists with variation of the rest of the molecule of Formula I as shown in Scheme 2.

SCHEME 1A

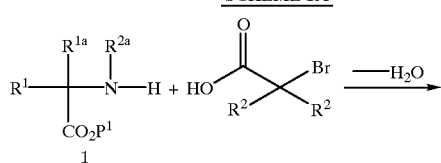

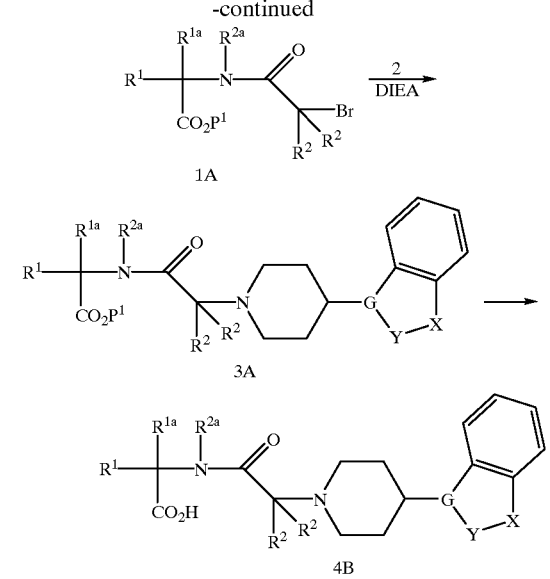

The preparation of amide intermediates of formula 4B can be achieved as shown in Scheme 1A. Standard peptide coupling reactions of protected amino acid 1 with 2-halo acids such as 2-bromoacetic acid gives intermediate 1A, which when reacted with amine of formula 2 gives the compound as 3A in the presence of a non-nucleophilic base such as DIEA. The P1 protecting group can be removed as described above.

SCHEME 2

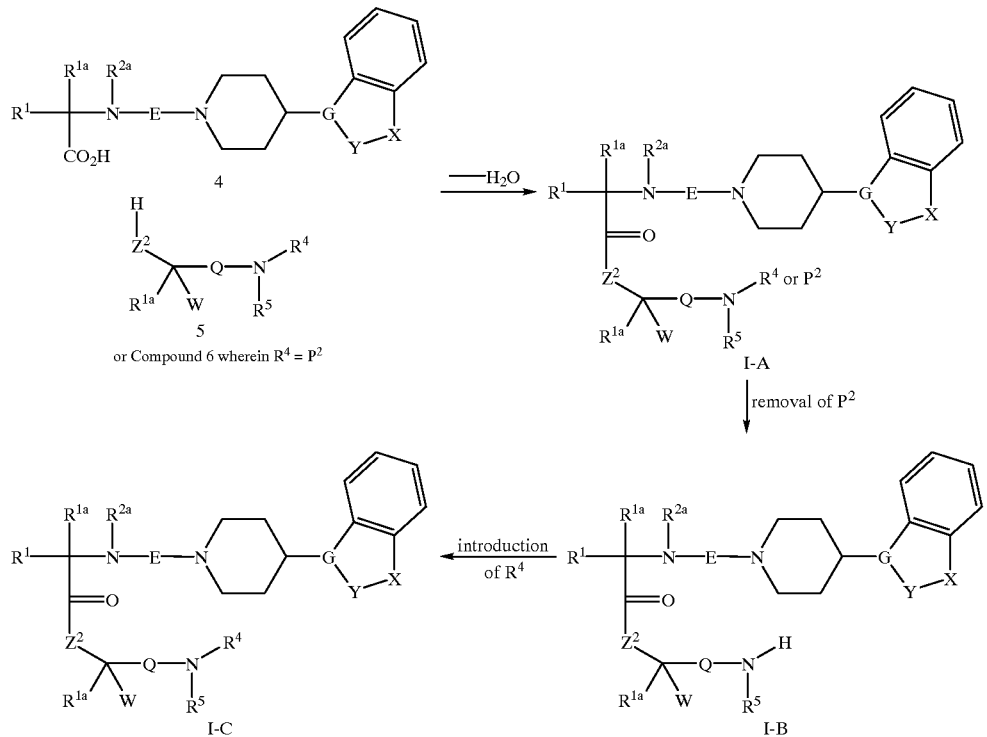

Intermediates of Formula 4 can be coupled to intermediates of formula 5 (or formula 6 wherein $R^4$ is $P^2$) wherein $Z^2$ is oxygen or substituted nitrogen to afford compounds of Formula I-A under standard ester or peptide coupling reaction conditions. $P^2$ is an amine protecting group such as BOC, Cbz, etc. Many of the selectively protected diamines or amino alcohol's of Formula 5 are either commercially available or known in the literature and others can be prepared following literature methods described for analogous compounds. Some of these methods are illustrated in subsequent schemes. Also if $R^4$ or $R^5$ is a hydrogen then the protected amino acids 6 are employed in the coupling reaction, wherein $P^2$ is a protecting group as defined above. The removal of $P^2$ in I-A to afford I-B, can be carried out as noted above. $R^4$ as defined above can then be optionally introduced to yield compound of general formula I-C according to procedures known in the art. For example, if $R^4$ is a substituted alkyl group, it can be introduced by reductive amination or opening of epoxide, or by alkylation by an alkyl halide; if $R^4$ is an amidino group, it can be introduced by the reagents such as 1-amidino-3,5-dimethylpyrazole nitrate (Methods Enzymol., 25b, 558, 1972).

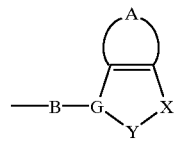

Formula II

The preparation of compounds of formula II within the scope of this invention may be achieved by methods known in the art. Such methods are illustrated in the following schemes for piperidines with A shown as an unsubstituted fused benzo ring. Analogous methods may be used for the preparation of the other ring compounds or with different substitutions on the ring or both as defined herein. In the interest of clarity, the benzo rings in the following schemes are depicted as being unsubstituted. Compounds bearing additional substituents on the benzo rings are readily prepared by minor modification of the methods herein with procedures known in the art.

SCHEME 3

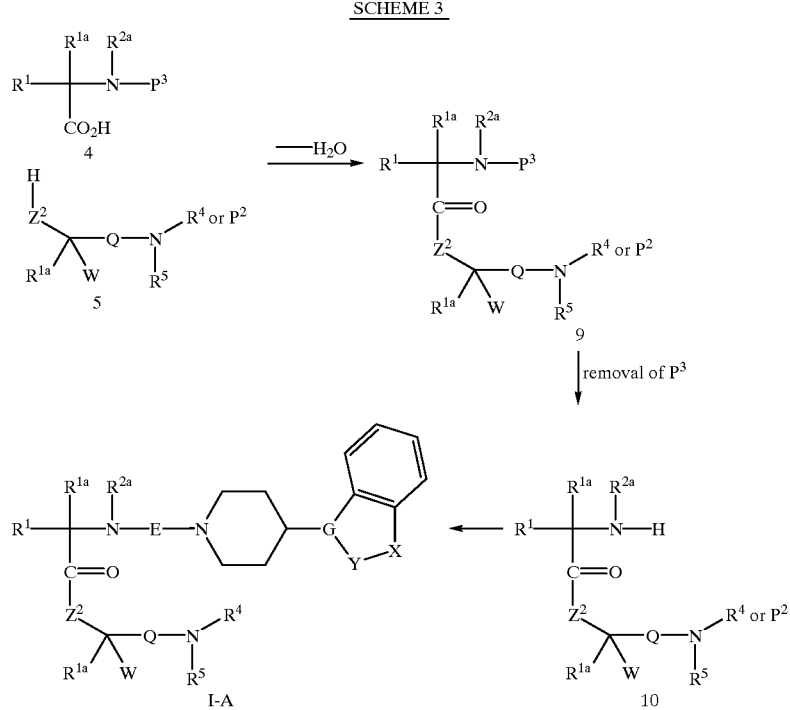

Alternatively, compounds of Formula I can be prepared starting from compound 5. The protected amino acid derivatives 8 are in many cases commercially available, where P3 is, for example, BOC, Cbz, Fmoc, and the like. N-Protected amino acid 8 can be coupled to intermediates of formula 5, wherein $Z^2$ is oxygen or substituted nitrogen to afford compounds of Formula 9 under standard ester or peptide coupling reaction conditions. The protecting group in compound 8 is selected with the criteria that its removal can be achieved without removing $P^2$. When the P2 protecting group is removed to afford compound 10, this compound can be further converted to compounds of formula I-A according to the procedures described in Scheme 1 and Scheme 1A. Further elaboration of compound I-A to I-B and I-C are illustrated in Scheme 2.

SCHEME 4

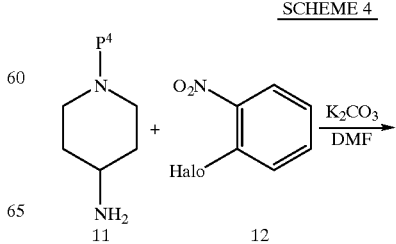

-continued

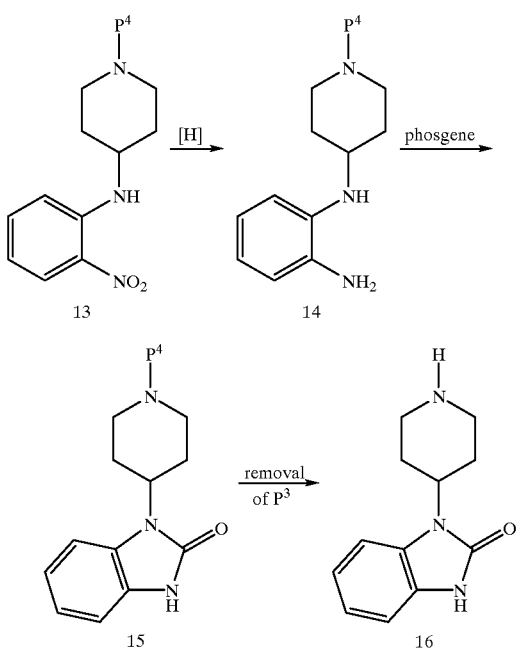

The piperidinylbenzimidazolinone 16 without substitution is commercially available; derivatives with substituents on the benzene ring are prepared by the methods shown in Scheme 4 as described in *J. Med. Chem.*, 30, 814–819 (1987) and U.S. Pat. No. 3,910,930, hereby incorporated by reference. $P^4$ is a protecting group such as benzyl, methyl, BOC, Cbz, ethyloxycarbonyl and the like. Thus, condensation of the commercially available 4-aminopiperidine 11, where $P^4$ is C(O)OEt, with a substituted o-halo nitrobenzene 12 gives the nitro compound 13. Reduction of the nitro group to an amine can be accomplished by catalytic hydrogenation with a catalyst such as Raney Ni, palladium on carbon or platinum on carbon in a protic solvent such as ethanol. Ring closure can be effected by phosgene or its equivalent such as DSC, CDI in the presence of a base. The protecting group $P^4$ can be removed by alkaline hydrolysis in the case of C(O)OEt or can be removed by the standard deprotection conditions as described in Greene, T, and Wuts, P. G. M., *Protective Groups in Organic Synthesis*, John Wiley & Sons, Inc., New York, N.Y. 1991.

SCHEME 5

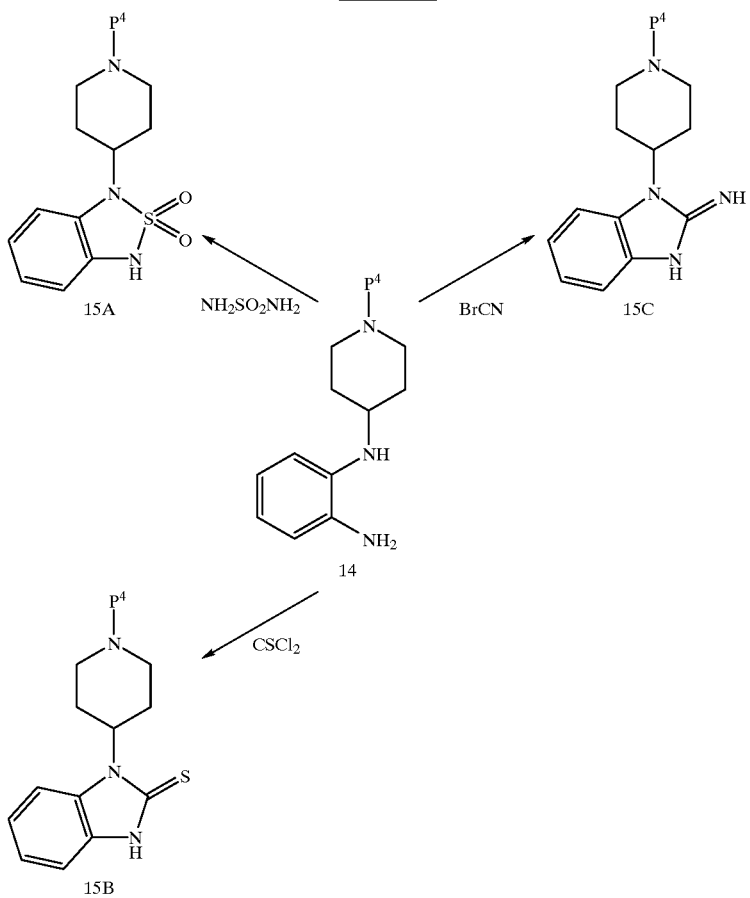

Similarly, other groups as defined by Y in compounds of Formula I can be prepared according to the reactions shown in Scheme 5. Thus, cyclic sulfamide 15 A can be prepared by reacting the diamine 14 and sulfamide; reaction of diamine 14 with thiophosgene or equivalents in the presence of a base gives the thiourea 15B; and reaction with cyanogen bromide yields compound 15C. The protecting group $P^4$ can be removed as described above.

In cases where $R^{11}$ is attached directly to the ring, such compounds can be prepared according to Scheme 7. Coupling compound 14 with a carboxylic acid or equivalents followed by ring closure under dehydration conditions gives compound 17. Removal of the $P^4$ protecting group yields the compound 18.

SCHEME 6

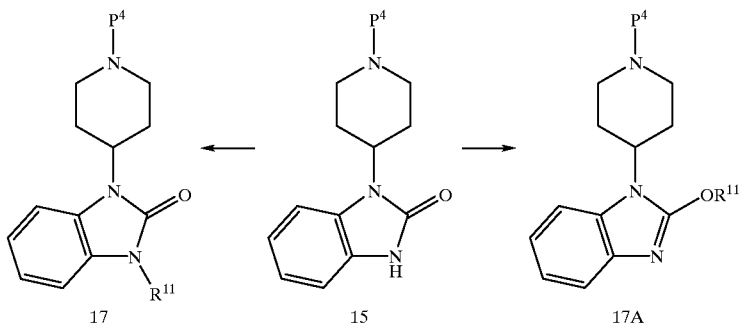

Benzimidazolones can be modified to introduce substituent $R^{11}$ through alkylation, acylation etc. with appropriate protecting group $P^4$ on the piperidine nitrogen. Similarly, compounds 15 A–C and 14D can be modified as defined by X and Y in formula I. The protecting group $P^4$ is selected in a way that its removal will not cause removal or alteration of $R^{11}$.

SCHEME 7

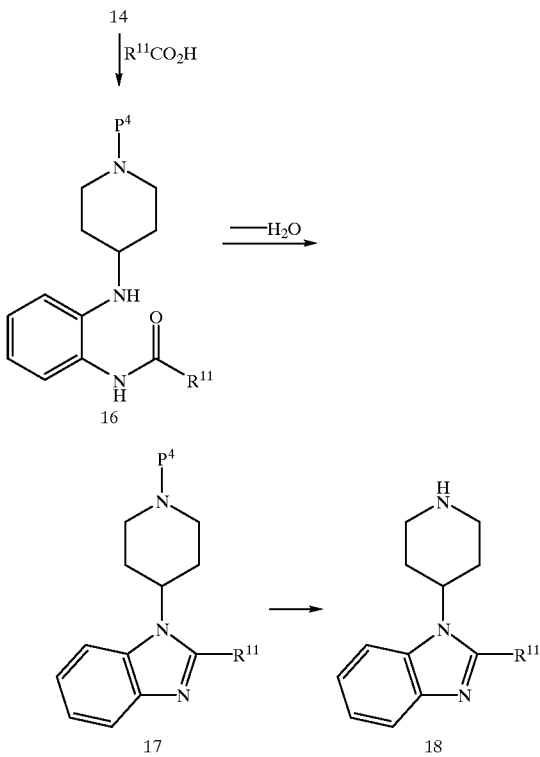

SCHEME 8

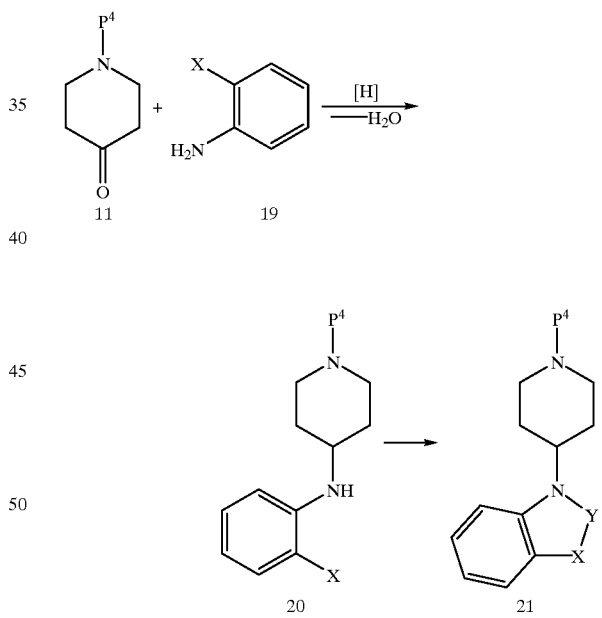

Alternatively, the ortho substituted aniline compound 19, where X is —OH, —NH2, —$NR^{11}$H, —SH, —$CH_2$OH, —$CH_2NH_2$, —$CH_2NR^{11}$H, —$CH_2$SH etc. can be reductively aminated with a protected 4-piperidinone 11 to afford compound 20. Ring closure can be effected through the chemistry discussed above.

SCHEME 9

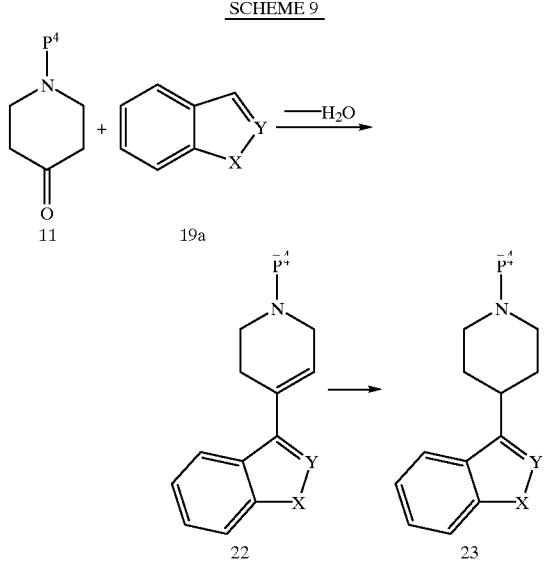

An alternative preparation involves an acid catalyzed coupling reaction of a protected 4-piperidinone 11 with an electron rich aromatic compound such as 19a, where X is O, S, NH or N-alkyl, and Y is CH, COH, $COR^{11}$, CH or N. The resulting 4-substituted tetrahydropyridines 22 obtained by this method can be elaborated to the instant compounds by utilizing chemistry detailed in Schemes 1–8. The 4-substituted tetrahydropyridines 22 can be hydrogenated by use of platinum or palladium catalysts in a protic solvent like methanol to give piperidines of formula 23 which can also be elaborated to the instant compounds of Formula I.

SCHEME 10

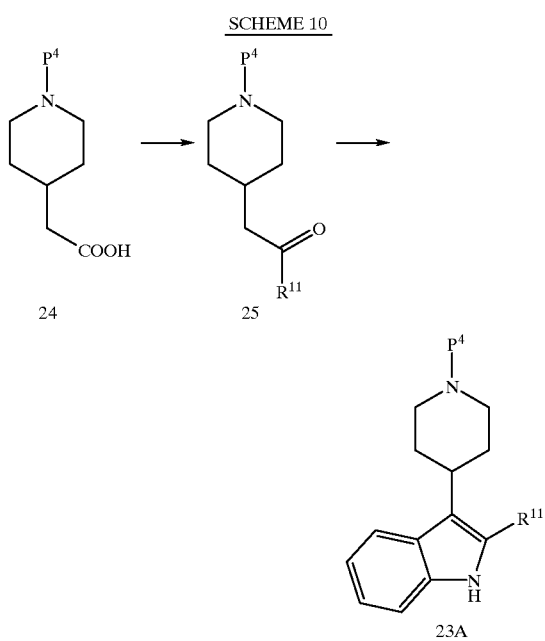

A specific indole embodiment of compound 23, where X=NH and Y=$CR^{11}$ and $R^{11}$ is H or alkyl, can be prepared using a Fisher indole synthesis protocol (see J. Chem. Soc. Chem. Commun., 563 (1981); J. Chem. Soc., 3175 (1957)) starting from a ketone or aldehyde and an aromatic hydrazine. Specifically, piperidines of formula 23A may be prepared from the protected piperidine acetic acid compound 24 as shown in Scheme 10. Conversion of the known carboxylic acid 24 to the corresponding aldehyde or ketones can be effected by a variety of conditions known in the art. For example, treatment of 24 with either oxalyl chloride or thionyl chloride in an inert solvent like benzene or carbon tetrachloride gives the corresponding acid chloride that is converted to the aldehyde 25 ($R^{11}$=H) by a Rosemund reduction. The conversion can also be effected by the Weinreb protocol in which an N,O-dimethyl hydroxylamine amide is reacted with a Grignard reagent to give the ketone or is reacted with LAH to give the aldehyde. Most hydrazines are commercially available or known in the literature and can be prepared accordingly. The condensation of the ketone 25 and hydrazine under the Fisher indole synthesis conditions yields the indole compound 23A. The protecting group $P^4$ can be removed by standard protocols and elaborated to the instant compounds by using chemistry presented in Schemes 1–8.

SCHEME 11

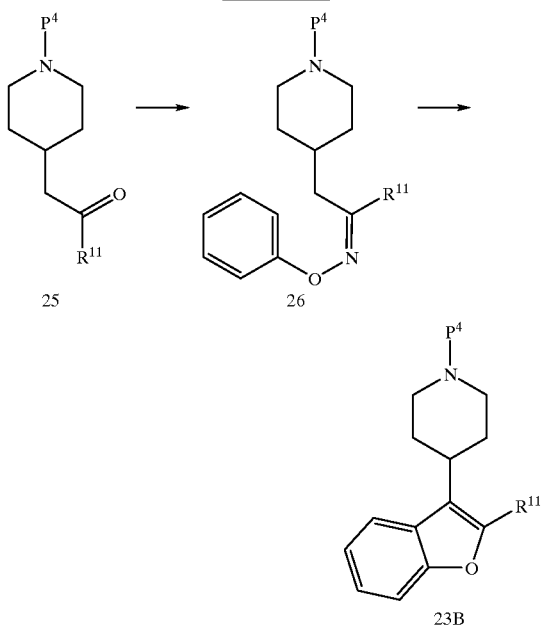

An analogous synthesis of benzofurans of formula 23B from o-aryloximes is exemplified by the transformation of 25 to 26 (see Tetrahedron Lett., 2867 (1967)) as depicted in Scheme 12.

Formula III

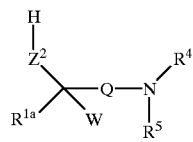

In many cases, compounds of Formula III or its mono protected form within the scopes of this invention are either commercially available or known in the art. In the simplest case where $Z^2$ is NH or O, $R^{1a}$, W, $R^4$ and $R^5$ are H's, Q is $(CH_2)x$, where x is 1–7, the formula represents diamines or amino alcohols, all of which are commercially available. Mono Boc protected diamine can be prepared by reacting excess diamine with $Boc_2O$ in methanol, where Boc pro tected amino alcohols can be preprared by reacting the amino alcohol with Boc₂O.

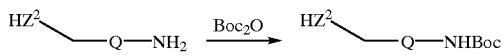

The above procedure is also applicable to compounds of formula III where R¹ᵃ and W are groups as define defined before.

Formula IV

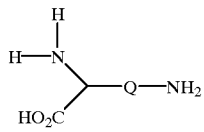

Compounds of Formula IV represent amino acids, which in many cases are commercially available. For example, when Q is (CH₂)₄ the structure represent lysine, when Q is (CH₂)₃ the structure represent ornithine. Many of these amino acids are available in a variety of protected form. They can be modified to give compounds as defined by the scope of the instant application. For example, with the two amino groups properly protected, the carboxylic acid can be converted into its next higher homologue, or to a derivative of the homologous acid, such as amide or ester by an Arndt-Eistert reaction. The acid can also be converted amides with a variety of amines as defined. The acid can be reduced to alhohol, which can be converted to ether by alkylation or reduced with methods know to those skilled in the art.

The preferred compounds of the invention are any or all of those specifically set forth in the Examples below. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

INTERMEDIATE 1

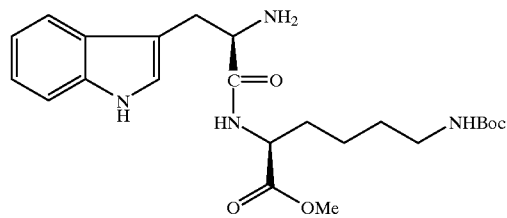

Step A:

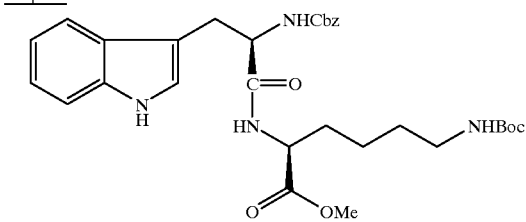

To a solution of commercially available N-Cbz-D-tryptophan (10.4 g, 30.6 mmol), N-e-t-BOC-L-Lysine methyl ester hydrochloride (9.55 g, 32.2 mmol), HOBt (6.21 g, 46.0 mmol) and DIEA (5.61 mL, 32.2 mmol) in dichloromethane (100 mL) at 0° C. was added EDC (8.81 g, 46.0 mmol) in several portions over a 10 min period. The reaction mixture was allowed to warm to room temperature and stirred for 16 hrs. The reaction mixture was then poured into a saturated solution of NaHCO₃ (100 mL), and the layers were separated. The organic layer was then sequentially washed with 100 mL portions of 1N HCl, water and brine, dried over anhydrous MgSO₄, filtered and concentrated to give 17.8 g (100% crude yield) a yellow/white solid.

Step B:

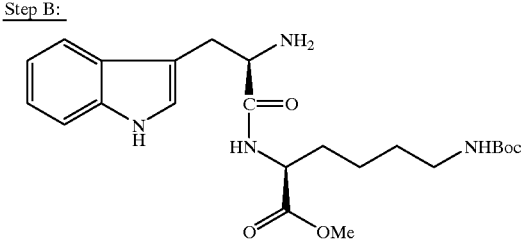

A mixture of the above product (17.8 g, 30.6 mmol) and Pearlman's catalyst [moist 20% Pd(OH)₂ on carbon, 1.8 g) in methanol (300 mL) was evacuated and purged with H₂ gas 3 times, then stirred at atmospheric pressure using a H₂ balloon for two hours. The reaction mixture was filtered through celite, TFA (3.5 g, 30.6 mmol) was added and the resulting solution was concentrated to give a white solid (16.3 g, 95% crude yield).

INTERMEDIATE 2

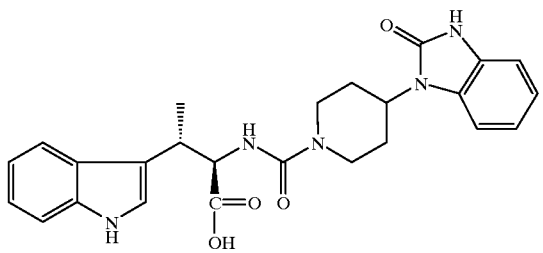

Step A:

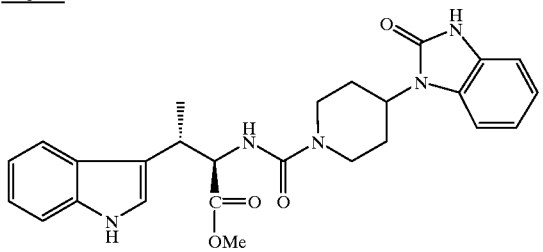

b-Methyl-D-Tryptophan methyl ester (6.00 g, 25.9 mmol) was combined with disuccinimidyl carbonate (6.95 g, 27.1 mmol) and DIEA (11.3 mL, 64.6 mmol) in dichloromethane. After stirring the reaction mixture for 0.5 h, 4-(2-keto-1-benzimidazolinyl)-piperidine (5.90 g, 27.1 mmol) was added and the mixture was permitted to stir over night. The reaction mixture was diluted with dichloromethane, and washed in succession with 1N HCl (100 mL), saturated NaHCO₃ solution (100 mL) and brine (100 mL), dried over MgSO₄, filtered and concentrated. The resulting crude prod uct was purified by MPLC (silica, 5% methanol/ethyl acetate) to give 7.55 g of a white solid.

Step B:

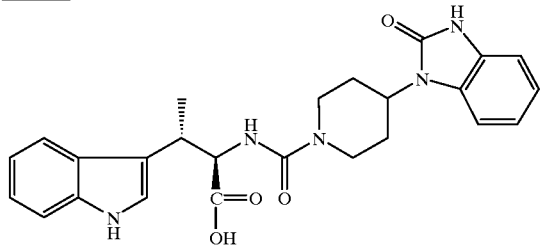

The coupled product from the previous step (7.55 g, 15.9 mmol) was dissolved in THF (30 mL), treated with LiOH (2.67 g, 63.6 mmol) in 1:1 EtOH/water (60 mL) and stirred for 4 h at room temperature. The pH was adjusted to ~2–3 by addition of 3N HCl and the resulting solution was extracted with ethyl acetate 3 times. The combined organic layers were washed with brine, dried over $MgSO_4$, filtered and concentrated to give 6.50 g of a white solid.

INTERMEDIATE 3

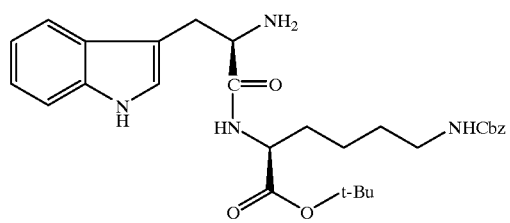

Step A:

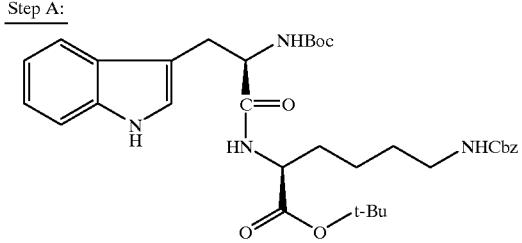

To a solution of commercially available N-BOC-D-Tryptophan (15.2 g, 50.0 mmol), N-e-Cbz-L-Lysine t-butyl ester hydrochloride (18.7 g, 50.0 mmol), HOBt (6.76 g, 50 mmol) and DIEA (8.71 mL, 50.0 mmol) in dichloromethane (350 mL) at 0° C. was added EDC (12.5 g, 65.0 mmol) in portions over a 10 min period. After 30 min at 0° C. the reaction mixture was permitted to warm to room temperature and was stirred for an additional 4 h. The reaction mixture was then poured into water (300 mL), the phases were separated, and the organic layer was washed in turn with saturated $NaHCO_3$ (250 mL) and brine (250 mL), dried over anhydrous $MgSO_4$, filtered and concentrated. The crude product was purified by flash chromatography (silica, 50% ethyl acetate/hexane), furnishing 27.5 g (88% yield) of product as a white solid.

$^1$H NMR ($CDCl_3$, 400 MHz) d 9.12 (br s, 1H), 7.70 (d, J=6.8 Hz, 1H), 7.31–7.38 (m, 6H), 7.08–7.17 (m, 2 H), 6.97 (d, J=1.6 Hz, 1H), 5.96 (br s, 1H), 5.28 (br s, 1H), 5.13 (s, 2H), 4.94 (br s, 1H), 4.49 (br s, 1H), 4.31 (app br d, J=5.2 Hz, 1H), 3.22–3.30 (m, 1H), 3.03–3.13 (m, 2H), 2.93–3.02 (m, 1H), 1.70 (br s, 2H), 1.43 (br s, 9H), 1.35 (s, 9H), 0.64–0.85 (m, 2H).

ESI-MS calc. for $C_{34}H_{46}N_4O_7$: 622; Found 623 (M+H).

Step B:

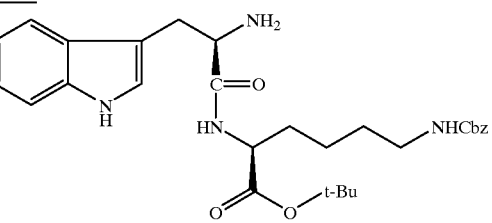

HCl gas was bubbled through a solution of the above product (10.0 g, 16.1 mmol) in ethyl acetate (75 mL) at 0° C. for two min. The reaction mixture was stirred for an additional 10 min., then concentrated to give 8.64 g of a mixture (3:2) of desired product to a side product in which the t-butyl ester of the product had been hydrolyzed to the corresponding acid.

ESI-MS calc. for $C_{29}H_{38}N_4O_5$: 522; Found 523 (M+H).

INTERMEDIATE 4

Step A:

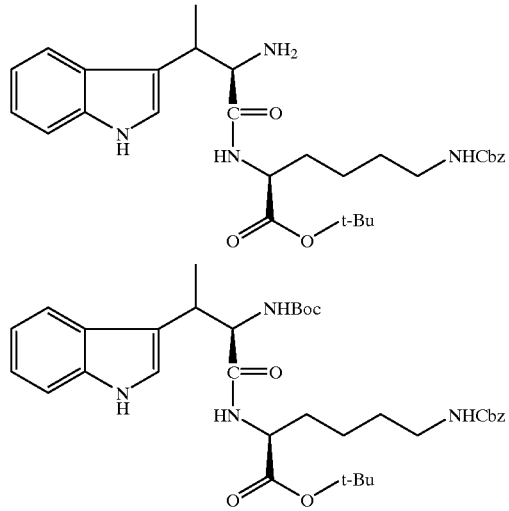

To a solution of N-BOC-b-methyl tryptophan (7.79 g, 24.5 mmol), N-e-Cbz-L-lysine t-butyl ester hydrochloride (10.04 g, 26.9 mmol), HOBt (4.96 g, 36.7 mmol) and DIEA (4.69 mL, 26.9 mmol) in dichloromethane (150 mL) at 0° C. was added EDC (7.04 g, 36.7 mmol) in portions over a period of 10 min. The reaction mixture was allowed to warm to room temperature, stirred for 3.75 h, and poured into a saturated solution of $NaHCO_3$ (100 mL). The organic layer was separated and washed sequentially with 1N HCl (100 mL), water (100 mL), and brine (100 mL), then dried over anhydrous $MgSO_4$, filtered and concentrated to give 14.5 g (93% crude yield) of a white/yellow solid.

Step B:

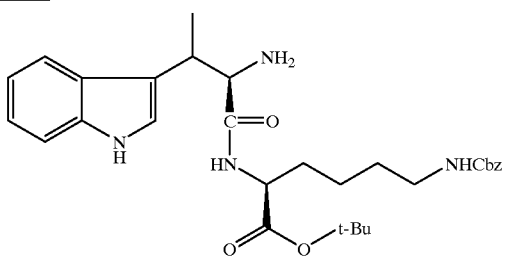

To a solution of the above BOC-b-methyl Trp-Lys(Cbz) O-t-butyl adduct (554 mg, 0.870 mmol) in methanol (8 mL) was added methane sulfonic acid (251 mg, 2.61 mmol) and the resulting mixture was stirred at room temperature for 70 hrs. The reaction mixture was concentrated to remove the methanol, dissolved in dichloromethane (50 mL) and washed three times with 2N NaOH solution (40 mL), once with brine (40 mL) and dried over anhydrous $MgSO_4$, filtered and concentrated to give 280.1 mg (60% yield) of a white solid. HPLC analysis indicated 93% purity of the desired amine.

INTERMEDIATE 5

Step A:

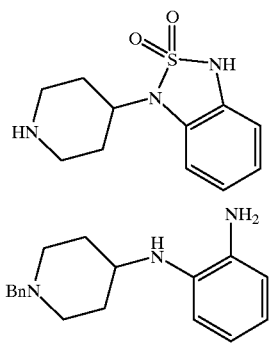

Commercially available 1-benzyl-4-(2-nitroaniline) piperidine (5.00 g, 16.1 mmol) was combined with $Pd(OH)_2/C$ (20%, 750 mg), methanol (50 mL) and concentrated HCl (13.3 mL, 161 mmol). The mixture was agitated under $H_2$ (g) (45 psi) for 24 h, filtered through celite, and concentrated. The resulting salt was partitioned between dichloromethane and 2N NaOH solution, the organic layer was washed with brine, dried over $MgSO_4$, filtered and concentrated to give 4.31 g of product as a red solid.

ESI-MS calc. for $C_{18}H_{23}N_3$: 281; Found 282 (M+H).

Step B:

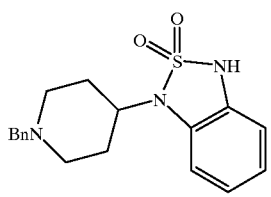

The product from step A above (4.31 g, 15.3 mmol) was combined with sulfamide (1.70 g, 17.6 mmol) in diglyme (60 mL) and the mixture was brought to reflux. After 3.5 h the solvent was removed under reduced pressure. Purification by flash chromatography (silica, 2.5% $NH_3OH$, 22.5% methanol/dichloromethane) afforded 1.61 g of pure product.

ESI-MS calc for $C_{18}H_{21}N_3O_2S$: 343; Found: 344 (M+H).

Step C:

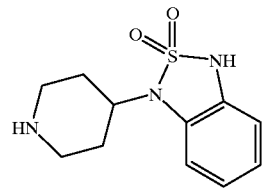

The product from the previous reaction (558 mg, 1.62 mmol) was combined with $Pd(OH)_2/C$ (20%, 100 mg), methanol (10 mL) and concentrated HCl solution (0.30 mL, 3.3 mmol) and agitated under $H_2$ (g) (50 psi) for 24 h. The reaction was filtered through celite, the filter cake washed with methanol and the reaction was repeated using fresh catalyst (100 mg). After an additional 24 h, more catalyst was added (280 mg) and the reaction was continued under $H_2$ (g) for 72 h, at which point TLC indicated that all of the starting material had been consumed. The reaction mixture was filtered through celite, the filter cake washed with more methanol and the filtrate concentrated to give the desired product.

ESI-MS calc for $C_{11}H_{15}N_3O_2S$: 253; Found: 254 (M+H).

INTERMEDIATE 6

Step A:

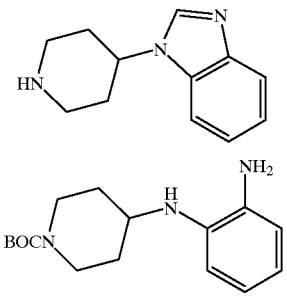

Step B:

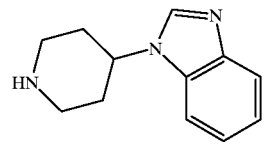

Formic acid (568 mg, 12.3 mmol) was added to $Ac_2O$ (1.05 g, 10.3 mmol) at 0° C. and the resulting mixture was warmed to 60° C., stirred for 2.75 h and cooled to room temperature. THF (5 mL) was then added, the solution was cooled to −15° C., and the product from the previous step (2.00 g, 6.86 mmol) was added in THF (5 mL). After 0.5 h the reaction mixture was concentrated (with warming at 40° C.) and the resulting crude product was purified by MPLC (silica, 90% ethyl acetate/hexane, then 100% ethyl acetate, then 4% methanol/ethyl acetate) to give 1.25 g of the benzimidazole. The BOC group was removed by dissolving the intermediate (1.21 g, 4.00 mmol) in ethyl acetate and bubbling HCl (g) through this solution for 10 min. The solvent was removed to afford Intermediate X.

BOC intermediate: ESI-MS calculated for $C_{17}H_{23}N_3O_2$: 301; Found: 302 (M+H).

INTERMEDIATE 7

Step A:

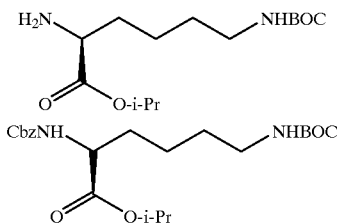

To a solution of N-a-Cbz-N-e-BOC-Lysine (15.0 g, 39.4 mmol), isopropanol (2.89 g, 47.3 mmol) and EDC (9.07 g, 47.3 mmol) in dichloromethane (300 mL) at 0° C. was added DMAP (5.06 g, 41.4 mmol). The reaction mixture was allowed to warm to room temperature, stirred for 24 h, diluted with dichloromethane (200 mL), washed twice with 1N HCl (250 mL), once with brine (250 mL), dried over $MgSO_4$, filtered and concentrated. The crude product was purified by flash chromatography (silica, 50% ethyl acetate/hexane), affording 16.0 g of the pure product (96% yield).

A mixture of the intermediate prepared in the previous step (16.0 g, 37.8 mmol) and 10% $Pd(OH)_2$/carbon (1.6 g) in methanol (150 mL) was treated with $H_2$ (g) via a balloon with magnetic stirring for 16 h. The reaction mixture was filtered through celite and concentrated to give the desired product (10.8 g, 99%).

INTERMEDIATE 8

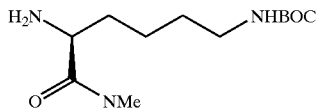

To a solution of commercially available N-a-Cbz-N-e-BOC-Lysine (10.0 g, 26.3 mmol), aqueous dimethylamine (2M solution, 15.8 mL, 31.5 mmol) and HOBt (3.73 g, 27.6 mmol) in dichloromethane (200 mL) at 0° C. was added EDC (6.05 g, 31.5 mmol) in portions over 5 min. The solution was permitted to warm to room temperature and stirred overnight. The reaction mixture was then diluted with 200 mL dichloromethane, washed in succession with 1 N HCl (200 mL), saturated $NaHCO_3$ (200 mL), and brine (200 mL), dried over $MgSO_4$, filtered and concentrated to afford a white solid. Removal of the Cbz protecting group was accomplished using the same protocol described earlier for the preparation of Preparative Example 6 (step B).

INTERMEDIATE 9

Step A:

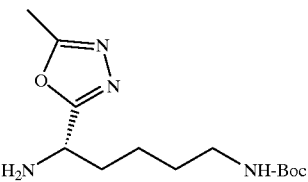

To a solution of hydrazine (4 ml) in 40 ml of methanol was added Z-Lys(Boc)-OSn(4.77 g) at room temperature. After stirring 1 hour, the mixture was concentrated to dry. The residue was added triethyl orthoacetate (15 ml) and heated at 140° C. for 60 hours. The resulting mixture was cooled to room temperature and poured into 1 N HCl(aq.). The mixture was extracted with methylene chloride, brine, dried over sodium sulfate and concentrated. The residue was purified by chromatatron (hexanes/ethyl acetate=1/1) to give the desired product which was dissolved in 30 ml of methanol, hydrogenated over $Pd(OH)_2$ at 1 atmosphere for 1 hour. The mixture was filtered through Celite to remove Pd catalyst. The filtrate was concentrated under vacuum to give the title compound (370 mg).

INTERMEDIATE 10

Step A:

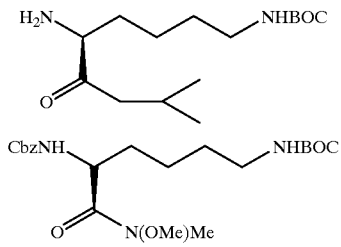

To a solution of N-a-Cbz-N-e-BOC-Lysine (10.0 g, 26.3 mmol), N,O-dimethylhydroxylamine hydrochloride (2.82 g, 26.3 mmol), HOBt (3.52 g, 26.3 mmol), and DIEA (5.50 mL, 31.6 mmol) in dichloromethane (300 mL) at 0° C. was added EDC (7.56 g, 39.5 mmol) in portions over 10 min. After stirring over night the reaction mixture was diluted with dichloromethane (200 mL) and washed once with water (250 mL), once with saturated $NaHCO_3$ solution (250 mL) and once with brine (250 mL), dried over $MgSO_4$, filtered and concentrated. The crude product was purified by flash chromatography (silica, 60% ethyl acetate/hexane) to provide 11.05 g (99%) of product.

$^1$H NMR (CDCl$_3$, 300 MHz) d 7.34 (m, 5H), 5.52 (d, J=8.1 Hz, 1H), 5.09 (app d, J=3.3 Hz, 2H), 4.72 (m, 1H), 4.60 (m, 1H), 3.77 (s, 3H), 3.20 (s, 3H), 3.06–3.12 (m, 2H), 1.34–1.77 (m, 6H), 1.42 (s, 9H).

ESI-MS calculated for $C_{21}H_{33}N_3O_6$: 423; Found: 424 (M+H).

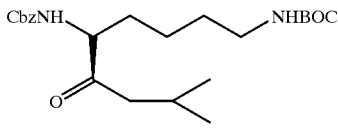

To a cooled solution (0° C.) of the amide prepared in the previous step (1.69 g, 4.00 mmol) in THF (20 mL) under an N$_2$ atmosphere was added dropwise by syringe isobutyl magnesium bromide (2M in diethyl ether, 6.0 mL, 12 mmol). After the addition the reaction mixture was allowed to warm to room temperature and stir for 4 h. The reaction was quenched by addition of water (~1 mL), diluted with ethyl acetate (100 mL) and washed with 1N HCl (25 mL) then brine (25 mL), dried over MgSO$_4$, filtered and concentrated. Purification by MPLC (silica, 40% ethyl acetate/hexane) afforded 427 mg of the desired product.

ESI-MS calculated for $C_{23}H_{36}N_2O_5$: 420; Found: 421 (M+H).

Step C:

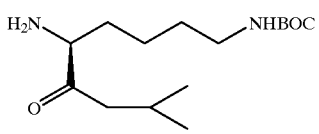

The product of the previous reaction (400 mg, 0.95 mmol) was combined with Pd/C (5%, 60 mg) in methanol and stirred under H$_2$ (g) for 2 h. The reaction mixture was filtered through celite, the filter cake was washed with additional methanol and the filtrate was concentrated to give 270 mg of the desired product.

INTERMEDIATE 11

Step A:

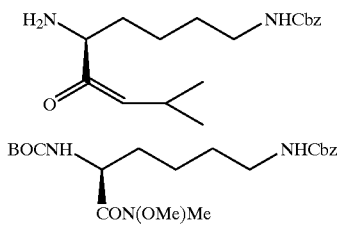

The Wienreb amide was prepared in the same fashion as described in Step A for the synthesis of Intermediate 10.

Step B:

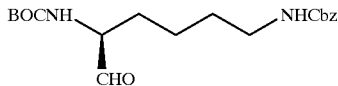

The product from the previous step (3.39 g, 8.00 mmol) was dissolved in ether (40 mL), purged with N$_2$, cooled to 0° C., and treated dropwise with a 1M solution of LAH in THF (10 mL, 10 mmol). After 1 h at 0° C. the reaction was quenched by dropwise addition of water, then diluted with 1 N HCl and washed twice with ethyl acetate. The combined organic layers were washed with brine, dried over MgSO$_4$, filtered and concentrated to give the desired product.

Step C:

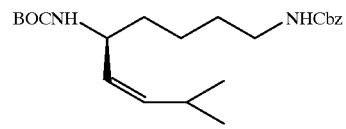

To a stirred mixture of dry isobutyltriphenylphosphonium bromide (1.68 g, 4.20 mmol) in THF (20 mL) at 0° C. under N$_2$ was added a 0.5M solution of KHMDS in toluene (8.4 mL, 4.2 mmol) dropwise over 10 min., and the resulting bright orange solution was stirred for 1 h. A solution of the product from the previous step (1.02 g, 2.80 mmol) in THF (10 mL) was then added dropwise at 0° C., warmed to room temperature and stirred for 18 h. The reaction was quenched with brine and extracted twice with ethyl acetate. The combined organic layers were washed once with brine, dried over Na$_2$SO$_4$, filtered and concentrated. Flash chromatographic purification (silica, 30% ethyl acetate/hexane) afforded 580 mg pure product.

$^1$H NMR (CDCl$_3$, 300 MHz) key peaks d 5.23 (t, J=10 Hz, 1H, —C$\underline{H}$=CH—), 5.00 (t, J=10 Hz, 1H, —CH=C$\underline{H}$—), 0.94 (d, J=6.6 Hz, 3H, —CHC$\underline{H}_3$), 0.91 (d, J=6.6 Hz, 3H, —CHC$\underline{H}_3$).

ESI-MS calculated for $C_{23}H_{36}N_2O_4$: 404; Found: 405 (M+H).

Step D:

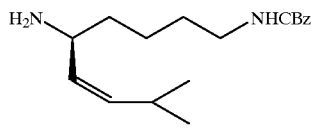

The product from the previous step (400 mg, 0.99 mmol) was dissolved in ethyl acetate, cooled to 0° C. and treated with gaseous HCl for ~2 min. then stirred for an additional 20 min. The solvent was removed to provide 333 mg of product.

ESI-MS calculated for $C_{18}H_{28}N_2O_2$: 304; Found: 305 (M+H).

INTERMEDIATE 12

Step A:

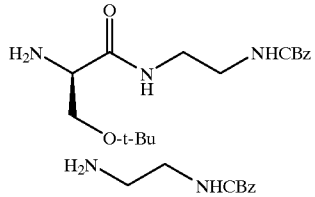

Commercially available 1-N-BOC-1,2-diaminoethane (5.00 g, 31.2 mmol) was combined with N-methyl morpholine (6.86 mL, 62.4 mmol) and DMAP (381 mg, 3.12 mmol) in dichloromethane (80 mL) and treated dropwise with benzyl chloroformate (4.76 mL, 32.8 mmol). After stirring at room temperature for an additional 4 h the reaction mixture was diluted with DCM (200 mL) and washed with 1N HCl (2×150 mL), saturated NaHCO$_3$ solution (150 mL) and brine (2×150 mL). The organic layer was dried over Na$_2$SO$_4$, filtered and concentrated to afford 9.20 g of a white solid.

¹H NMR (CDCl₃, 300 MHz) d 7.26–7.39 (m, 5H), 5.19 (br s, 1H), 5.09 (s, 2H), 4.83 (br s, 1H), 3.15–3.31 (m, 4H), 1.43 (s, 9H).

ESI-MS calculated for $C_{15}H_{22}N_2O_4$: 294; Found: 295 (M+H).

This crude product was dissolved in ethyl acetate, cooled to 0° C., and treated with gaseous HCl for 5 min. The solvent was then removed to provide 7.2 g of the desired product.

¹H NMR (CD₃OD, 300 MHz) d 7.28–7.41 (m, 5H), 5.10 (s, 2H), 3.40 (t, J=5.7 Hz, 2H), 3.05 (t, J=5.7 Hz, 2H).

ESI-MS calculated for $C_{10}H_{14}N_2O_2$:194; Found 195 (M+H).

Step B:

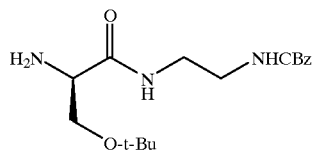

To a solution of the product from the previous step (1.26 g, 5.46 mmol), N-a-FMOC-D-serine-O-t-butyl ether (2.0 g, 5.2 mmol), HOBt (703 mg, 5.20 mmol) and DIEA (0.91 mL, 5.2 mmol) in DCM (50 mL) at 0° C. was added EDC (1.49 g, 7.8 mmol) slowly over 5 min. The reaction mixture was permitted to warm to rt. After stirring overnight, the reaction mixture was diluted with DCM and washed in turn with water, saturated NaHCO₃ solution and brine. The organic layer was dried over MgSO₄, filtered and concentrated to afford the crude product.

The resulting crude product was dissolved in a 20% solution of morpholine in DCM (50 mL) and stirred overnight. The reaction mixture was diluted with DCM and washed with water 4 times and brine once. The organic phase was dried over MgSO₄, filtered, concentrated and purified by flash chromatography (silica, 1:9:90 NH₃OH/MeOH/DCM) to give the desired product.

ESI-MS calculated for $C_{17}H_{27}N_3O_4$: 337; Found: 338 (M+H).

INTERMEDIATE 13

Step A:

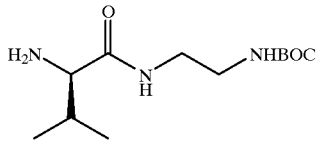

-continued

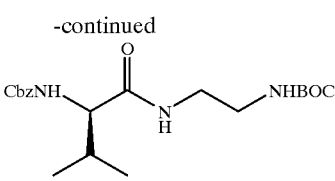

To a solution of Z-valine (2.00 g, 7.96 mmol), 1-N-BOC-1,2-diaminoethane (1.40 g, 8.76 mmol), and HOBt (1.08 g, 7.96 mmol) in DCM (50 mL) at 0° C. was added EDC (2.28 g, 11.9 mmol) over ~5 min. The reaction mixture was then allowed to warm to rt and stir for 2 h. Dilution with DCM was followed by washing with water, saturated NaHCO₃ solution and brine. The organic layer was dried over MgSO₄, filtered and concentrated to give 3.01 g of desired product.

Step B:

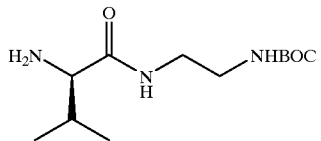

A mixture of the product from the previous reaction (3.00 g, 7.63 mmol) and Pd(OH)₂/C (20%, 300 mg) was dissolved in MeOH (50 mL) and stirred under H₂ for 2 h. The reaction mixture was filtered through celite and the filtercake washed with MeOH. The filtrate was concentrated to give 1.96 g of the desired product.

INTERMEDIATE 14

Some of the instant compounds can be prepared employing solid phase methodology, the general procedure for which is described below:

Preparation of resin-bound diamine or amino-alcohol:

Transfer 1.8 g of Rapp Tentagel HMPB resin (0.20 mmol/g, see FIG. 1) to a fritted tube and washed with 30 mL of 1:1 THF/CH₂Cl₂. Add 9 mL of a 0.75M solution of DIEA in THF/CH₂Cl₂. Add 9 mL of a 0.75M solution of p-nitrophenylchloroformate in THF/CH₂Cl₂. Agitate for 6 hours. Draine the tube and wash the resin with 2×30 mL of THF/CH₂Cl₂. Add 18 mL of a 0.25M DMF solution of a 1:1 mixture of diamine or amino-alcohol (see Table 1) and DIEA and agitated for 16 hours. Drain the tube and washed the resin with 4×20 mL of DMF.

FIG. 1. Rapp Tentagel HMPB Resin

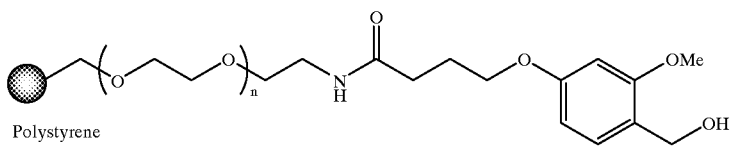

Transferr 25 mg of diamine or amino-alcohol loaded resin (see FIG. 2 and Table 1) into a fritted tube. Wash the resin with 2×1.5 mL of DMF. Add 250 µL of a 0.52M solution of Fmoc-(RS,SR)-b-methyltryptophan in DMF. Add 250 µL of a 0.52M solution of DIC/3% DMAP in DMF. Agitate the reaction vessel for 3 hours. Drain the tube and wash the resin with 2×1.5 mL of DMF and repeat the acylation. Drain the tube and washed the resin with 3×1.5 mL of DMF. Add 500 µL of 20% piperidine in DMF and agitate for 30 minutes. Drain and wash the resin with 2×1.5 mL each of DMF and 1:1 THF/CH$_2$Cl$_2$. Add 250 µL of a 0.5M solution of DIEA in THF/CH$_2$Cl$_2$. Add 250 µL of a 0.5M solution of p-nitrophenylchloroformate in THF/CH$_2$Cl$_2$. Agitat for 30 minutes. Drain the tube and wash the resin with 2×1.5 mL of THF/CH$_2$Cl$_2$. Add 500 µL of a 0.25M solution of 1:1 4-(2-keto-1-benzimidiazolinyl)piperidine/DIEA in DMF and agitate for 20 minutes. Drain the tube, and wash the resin with 3×1.5 mL each of DMF, THF/CH$_2$Cl$_2$, THF, CH$_2$Cl$_2$, isopropanol, CH$_2$Cl$_2$, and glacial acetic acid. Add 1 mL of glacial acetic acid under nitrogen, and heat to 40° C. for 21.5 hours to release the compound from the resin. Drain the tube, collecting the solution. Lyophilize this solution to afford the product. Mass Spectroscopy confirms the presence of the desired product (See Table 2).

FIG. 2.

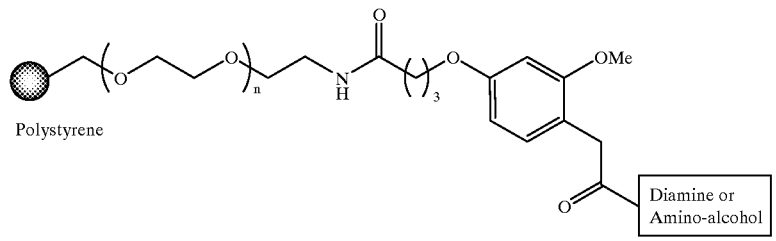

INTERMEDIATE 15

N-acetyl-Threo-(2R,3S)-b-methyltryptophan R-(+)-a-methylbenzylamine salt

Racemic b-methyltryptophan was prepared by the method of Snyder and Matteson (J. Am. Chem. Soc. 1957, 79, 2217.) Isomer A (100 g) was suspended in 1.25 L of 90/10 acetone water at 20° C. and 50 mL of R-(+)-a-methylbenzylamine was added in one portion. The suspension cleared briefly before a thick white suspension formed which quickly turned to a solid mass. After aging overnight, an additional 500 mL of acetone was added to facilitate agitation and filtration. The suspension was filtered and the cake washed with 500 mL of acetone and sucked to a damp cake. The solid was suspended in 2.5 L of 90/10 acetone /water and heated to boiling on a steam bath. The white slurry was allowed to cool to 20° C. overnight. The product was collected by filtration, washed with acetone and dried yielding 39.1 g of the title compound. a=+9.1° (c=1, MeOH) Stereochemical assignments were made by comparison to published compounds: J. Org. Chem. 1994, 59, 4239 and J. Org. Chem. 1995, 60, 4978.

INTERMEDIATE 16

N-acetyl-Threo-(2S,3R)-b-methyltryptophan S-(−)-a-methylbenzyl amine salt

The mother liquors from the intermediate 15 were combined and concentrated to ca. 1 L and 400 mL of 1 N HCl was added. The resulting suspension was stirred for 1 hr initially at 20° C. then at 0° C. The product was filtered and washed with water until the filtrate was neutral. The product was sucked to a damp cake weighing 79 g. The solid was suspended in 1 L of 95% acetone/water and 40 mL of S-(−)-a-methylbenzylamine was added followed by 1 L of 90% acetone/water. After a few minutes a solid mass formed. An additional 500 mL of acetone was added and the mixture heated on a steam bath for ca. 0.5 hr. This was then allowed to stand at 20° C. overnight. The product was collected by filtration, washed with 500 mL of acetone, and sucked to a damp cake. The product was suspended in 2 L of 95% acetone/water and heated on a steam bath to boiling. The white suspension was allowed to cool to 20° C. overnight. The product was collected by filtration, washed with 500 mL of acetone and dried yielding 54 g. a=−9.0° (c=1, MeOH).

INTERMEDIATE 17

N-acetyl-Erythro(2R,3R)-b-methyltryptophan R-(+)-a-methylbenzyl amine salt 170 g of Isomer B (see ref. in intermediate 15) which was a brittle foam containing ethyl acetate was dissolved in 2.5 L of ethyl acetate containing 100 mL of ethanol. To this was added 60 mL of R-(+)-a-methylbenzylamine. After 10 min, an additional 2 L of ethyl acetate was added and the resulting thick suspension was aged at 20° C. for 3 days. The product was collected by filtration, washed with ethyl acetate and and sucked to a damp cake. The salt was reslurried four times with hot ethyl acetate containing 2% water (1×2.5 L, 2×6 L, and 1×8 L). The yield of dried product was 43.2 g of salt. a=−19.6° (c=1, MeOH).

INTERMEDIATE 18

N-acetyl-Erythro (2S,3S)-b-methyltryptophan S-(−)-a-methylbenzyl amine salt

The mother liquors from the intermediate 18 were combined and concentrated to ca. 2 L and washed twice with 500 mL 1 N HCl. The washes were back extracted once with ethyl acatate, and the combined ethyl acetate extracts washed twice with brine. The solution was diluted to 6 L with ethyl acatate and 60 mL of S-(−)-a-methylbenzylamine was added. After 10 min the resulting suspension was heated to boiling. The suspension was allowed to cool to ambient temperature with stirring overnight. The product was collected by filtration washed with ethyl acetate and and sucked to a damp cake. The salt was suspended in 6 L of ethyl acetate and suspension was heated to boiling. The suspension was allowed to cool to ambient temperature with stirring overnight. The product was collected by filtration washed with ethyl acetate and dried. The yield of dried product was 65.8 g of salt. a=+19.7° (c=1, MeOH).

INTERMEDIATE 19

N-acetyl-threo-(2S,3R)-b-methyltryptophan

The salt from intermediate 16 (53 g) was stirred with 400 mL 1 N HCl at 20° C. for 20 min. The suspension was filtered and the cake washed with water until the filtrate was neutral. The wet cake was used directly for the next reaction. A sample was dried affording the title compound. a=−26.4° (c=1,MeOH).

INTERMEDIATE 20 threo-(2S,3R)-b-methyltryptophan

The wet cake from intermediate 19 was suspended in with 400 mL of 1 N HCl and refluxed for 12 hours. The solution was cooled to 20° C., and half of the solution was used for example 7. The title compound isolated by adjusting the pH to 7.0 with sodium hydroxide, cooling the resulting suspension to 0° C., filtering, washing the cake with water and drying. a=−29.3° (c=0.9, $H_2O$).

INTERMEDIATE 21

N-t-BOC-threo-(2S,3R)-b-methyltryptophan

The pH of the aqueous solution from intermediate 20 was adjusted to 7 with sodium hydroxide and cooled to 0° C. 20 g of potassium carbonate, 19 g of di-t-butyldicarbonate, and 150 mL of THF were added. The mixture was allowed to warm slowly to ambient temperature overnight. The reaction was extracted twice with ether, the aqueous acidified with 2 N HCl and extracted twice with ethyl acetate. The combined ethyl acetate extracts were washed with brine, dried with $MgSO_4$, filtered and concentrated affording 21.2 g of the title compound.

INTERMEDIATE 22

N-acetyl-threo-(2R,3S)-b-methyltryptophan Was prepared following the proceedure of intermediate 19. a=+26.6° (c=1,MeOH).

INTERMEDIATE 23 threo-(2R,3S)-b-methyltryptophan

Was prepared following the proceedure of intermediate 20. a=+30.60 (c=0.9, $H_2O$).

INTERMEDIATE 24

N-t-BOC-threo-(2R,3R)-b-methyltryptophan

Was prepared following the proceedure of intermediate 21.

INTERMEDIATE 25

N-acetyl-Erythro (2S,3S)-b-methyltryptophan

The salt from intermediate 18 (65 g) was stirred with 250 mL 1 N HCl and 1.5 L of ethyl acetate at ambient temperature for 5 min. The layers were partitioned and the ethyl acetate layer was washed with 1N HCl, $H_2O$ and brine, dried with $MgSO_4$, filtered and concentrated to afford the title compound as a brittle foam.

INTERMEDIATE 26

Erythro (2S,3S)-b-methyltryptophan

The product from intermediate 25 was suspended in with 500 mL of 2 N HCl and refluxed for 4 hours. The solution was cooled to 20° C., and half of the solution was used for intermediate 27. The title compound isolated as a foam by concentrating the solution in vacuo.

INTERMEDIATE 27

N-t-BOC-Erythro (2S,3S)-b-methyltryptophan

The pH of the aqueous solution from intermediate 20 was adjusted to 7 with sodium hydroxide and cooled to 0° C. 24 g of potassium carbonate, 22 g of di-t-butyldicarbonate, and 150 mL of THF were added. The mixture was allowed to warm slowly to ambient temperature overnight. The reaction was extracted twice with ether The aqueous acidified with 2 N HCl.and extracted twice with ethyl acetate. The combined ethyl acetate extracts were washed with brine, dried with $MgSO_4$ filtered and concentrated. The solid was redissolved in ether, and the ether removed in vacuo while flushing with hexanes. The resulting slurry was filtered and dried affording 20.1 g of the title compound.

INTERMEDIATE 28

N-acetyl-threo-(2R,3R)-b-methyltryptophan

Was prepared following the proceedure of intermediate 25. a=° (c=1,MeOH).

INTERMEDIATE 29 threo-(2R,3R)-b-methyltryptophan

Was prepared following the proceedure of intermediate 26. a=° (c=0.9, $H_2O$).

INTERMEDIATE 30

N-t-BOC-threo-(2R,3R)-b-methyltryptophan

Was prepared following the proceedure of intermediate 27.

EXAMPLE 1

Step: A

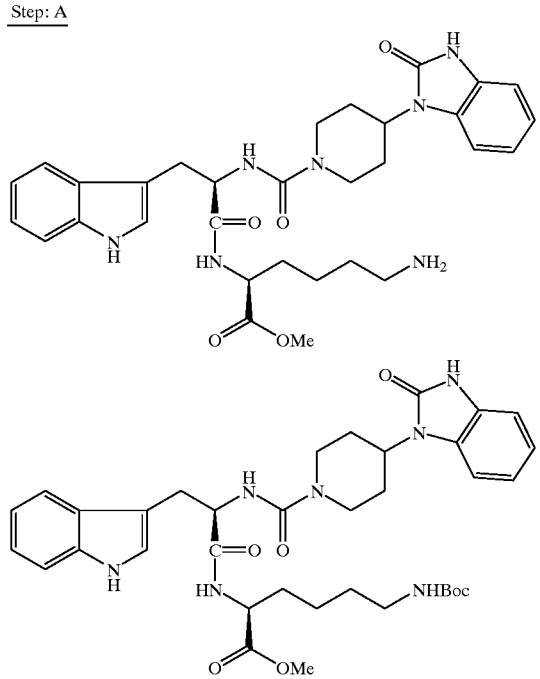

D-Trp-N-e-BOC-Lys-OMe.HCl (300 mg, 0.535 mmol), prepared as indicated above, was combined with disuccinimidyl carbonate (137 mg, 0.535 mmol) and DIEA (0.373 mL, 2.14 mmol) in THF (10 mL) and stirred at room temperature for 0.5 h. To the resulting clear solution was added 4-(2-keto-1benzimidazolinyl)-piperidine (116 mg, 0.535 mmol) and stirring was continued for an additional 16 h. The reaction mixture was concentrated, redissolved in dichloromethane (40 mL), washed successively with 1N HCl (30 mL), saturated NaHCO₃ (30 mL) and brine (30 mL), dried over anhydrous MgSO₄, filtered and concentrated. The crude product was purified by MPLC (silica, 5%MeOH/EtOAc) to give a white solid.

MS-CI (NH₃) calc. for $C_{36}H_{47}N_7O_7$: 689; Found 590 (M+H-100 [BOC]).

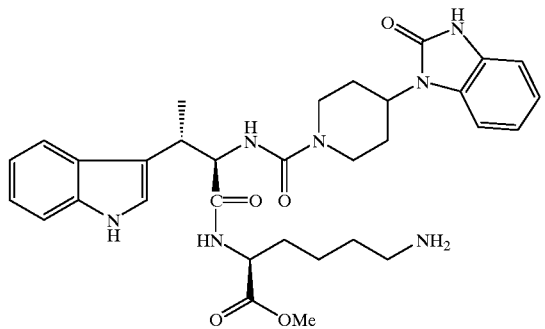

The BOC precursor, prepared as described above, was dissolved in ethyl acetate (5 mL), cooled to 0° C., and through this solution was bubbled HCl (g) for 2 min. After stirring for an additional 15 min., the solvent was removed under reduced pressure to give a white solid.

¹H NMR (CD₃OD, 400 MHz) d 7.63 (d, J=8 Hz, 1H), 7.32 (d, J=8 Hz, 1H), 7.17 (s, 1H), 7.01–7.10 (m, 7H), 4.57 (app t, J=8 Hz, 1H), 4.38–4.42 (m, 2H), 4.06–4.17 (m, 2H), 3.70 (s, 3H), 3.29–3.35 (m, 1H), 3.17 (dd, J=14.4, 8.4 Hz, 1H), 2.79–2.97 (m, 4H), 2.28–2.32 (m, 1H), 2.11–2.16 (m, 1H), 2.00 (m, 1H), 1.63–1.81 (m, 3H), 1.50–1.63 (m, 2H), 1.13–1.25 (m, 2H).

ESI-MS calc. for $C_{31}H_{39}N_7O_5$: 589; Found 590 (M+H).

EXAMPLE 2

Step: A

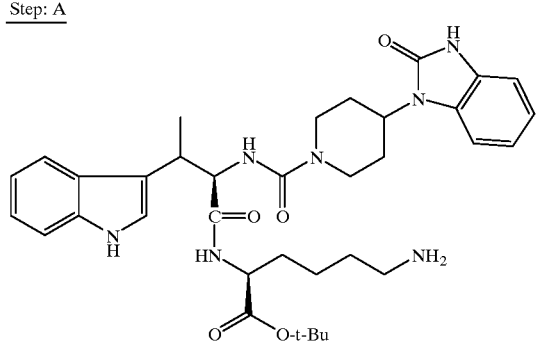

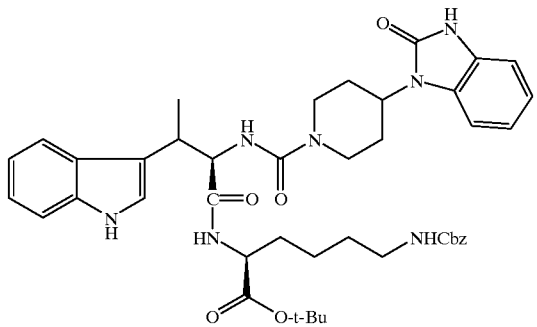

Intermediate 5 (TFA salt, 3.80 g, 5.84 mmol) was combined with disuccinimidyl carbonate (1.50 g, 5.84 mmol) and DIEA (3.05 mL, 31.8 mmol) in dichloromethane (50 mL), stirred at room temperature for 0.5 h, and treated with 4-(2-keto-1-benzimidazolinyl)-piperidine (1.27 g, 5.84 mmol). The resulting mixture was stirred for an additional 2 h, diluted with dichloromethane, washed in turn with saturated NaHCO₃, 1N HCl and brine, dried over MgSO₄, filtered and concentrated. MPLC purification (silica, 3% methanol/ethyl acetate) furnished 3.20 g of the desired product.

ESI-MS calc. for $C_{43}H_{53}N_7O_7$: 779; Found 780 (M+H).

Step B:

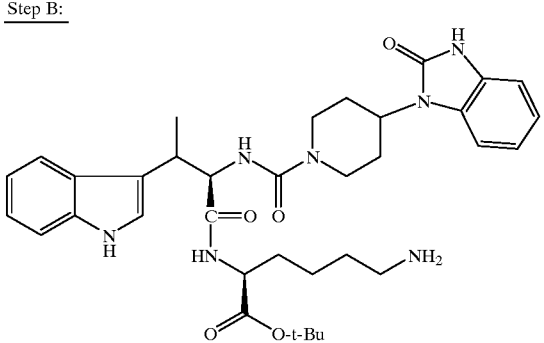

The adduct prepared as described in Step A above (3.10 g, 3.97 mmol) and Pd/C (10%, 310 mg) were combined in methanol (~50 mL) and stirred under H₂ (g) (administered via balloon) for 2 h. The reaction mixture was filtered through celite, treated with 1 eq of concentrated HCl, and concentrated to give the desired product as a white solid.

ESI-MS calc. for $C_{35}H_{47}N_7O_5$: 645; Found 646 (M+H).

EXAMPLE 3

Step A:

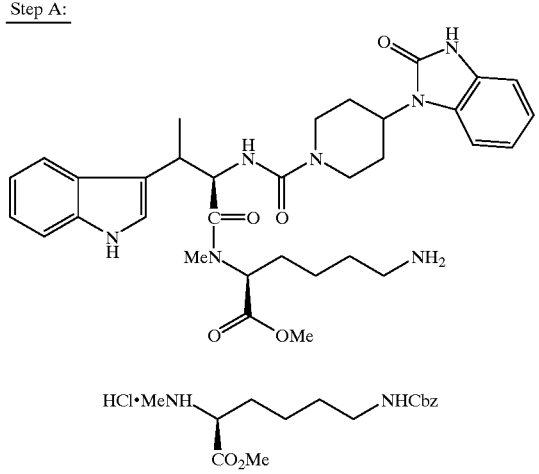

Thionyl chloride (0.74 mL, 10 mmol) was added dropwise to precooled methanol (10 mL, 0° C.). To the resulting solution was added commercially available N-a-BOC-N-a-methyl-N-e-Cbz-Lysine dicyclohexylamine salt and the reaction was brought to reflux. After 2 h the reaction mixture was cooled and the solvent and by-products removed in vacuo. The crude product was used "as is".

Step B:

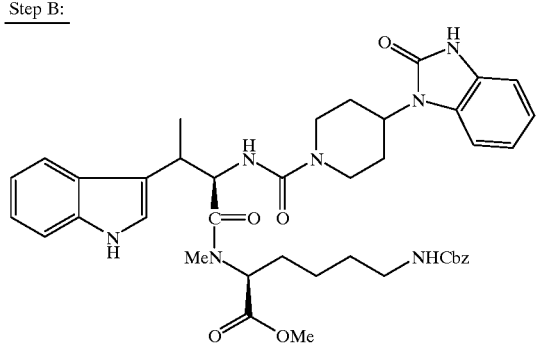

To a solution of the crude product from the previous step (395 mg), Intermediate 3 (277 mg, 0.601 mmol), prepared as described above, HOBt (94.6 mg, 0.601 mmol) and DIEA (125 mL, 0.601 mmol) in dichloromethane was added at 0° C. EDC (173 mg, 0.901 mmol). The reaction mixture was stirred at room temperature for 18 h, diluted with dichloromethane and washed in succession with water, saturated NaHCO$_3$ solution, and brine, dried over MgSO$_4$, filtered and concentrated. MPLC purification (silica, 3% methanol/ethyl acetate) afforded 92 mg of pure product.

ESI-MS calc. for $C_{41}H_{49}N_7O_7$: 751; Found 752 (M+H).

Step C:

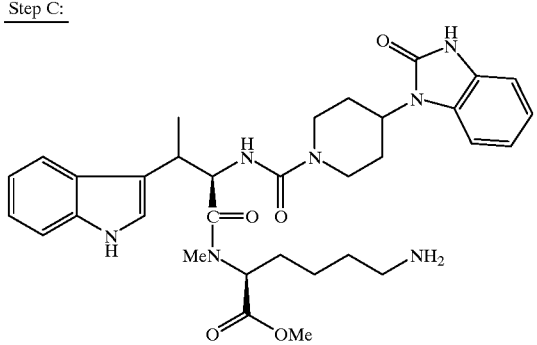

The product from step B above (92.0 mg, 0.123 mmol) was combined with Pd/C (10%, 20 mg) in methanol (3 mL) and stirred under H$_2$ (g) for 1 h. The reaction mixture was filtered through celite, treated with one equivalent of concentrated HCl solution and concentrated to give the desired product as its hydrochloride salt.

ESI-MS calc. for $C_{33}H_{43}N_7O_5$: 617; Found 618 (M+H).

The following compounds shown in Table I, containing representative modifications to the benzimidazolidinyl piperidine structure, were prepared from Intermediates 4–7 according to the above established procedures as exemplified in Example 1, steps A and B and Example 2, steps A and B.

TABLE 1

| example | $R^{1a}$ | $R^2$ | G—Y—X | MF ESI-MS (M + H) |
|---|---|---|---|---|
| 4 | H | H | N—CO—NH | $C_{34}H_{45}N_7O_5$-632 |
| 5 | CH$_3$ | H | N—CO—NH | $C_{35}H_{47}N_7O_5$-646 |
| 6 | CH$_3$ | 5-F | N—CO—NH | $C_{35}H_{46}FN_7O_5$-664 |
| 7 | CH$_3$ | 5-F | N—CO—NCH$_2$CF$_3$ | $C_{37}H_{47}F_4N_7O_5$-746 |
| 8 | CH$_3$ | H | N—SO$_2$—NH | $C_{34}H_{47}N_7O_6$S-682 |
| 9 | CH$_3$ | H | N—CO—NCH$_3$ | $C_{36}H_{49}N_7O_5$-660 |
| 10 | CH$_3$ | H | N—CO—NCH$_2$CH$_3$ | $C_{37}H_{51}N_7O_5$-674 |
| 11 | CH$_3$ | H | N—CO—NCH$_2$CO$_2$H | $C_{37}H_{49}N_7O_7$-704 |
| 12 | CH$_3$ | H | N—C=N | $C_{35}H_{47}N_7O_4$-630 |
| 13 | CH$_3$ | H | N—CO—O | $C_{35}H_{46}N_6O_6$-647 |
| 14 | CH$_3$ | 7-CO$_2$Me | N—CO—O | $C_{37}H_{48}N_6O_8$-705 |
| 15 | CH$_3$ | 6-F | N—CO—O | $C_{35}H_{45}FN_6O_6$-665 |
| 16 | CH$_3$ | 6-CO$_2$Me | N—CO—O | $C_{37}H_{48}N_6O_8$-705 |
| 17 | CH$_3$ | 5-CO$_2$Me | N—CO—O | $C_{37}H_{48}N_6O_8$-705 |
| 18 | CH$_3$ | H | C=CH—NH | $C_{36}H_{48}N_6O_4$-629 |
| 19 | CH$_3$ | H | N—CNHAc=N | $C_{37}H_{50}N_8O_5$-687 |
| 20 | CH$_3$ | 5-CH$_3$ | N—CO—NH | $C_{36}H_{49}N_7O_5$-660 |

TABLE 1-continued

[Structure with R^{1a}, R^2, G-Y-X, NH2, O-t-Bu groups]

| example | R^{1a} | R^2 | G—Y—X | MF ESI-MS (M + H) |
|---------|--------|-----|--------|-------------------|
| 21 | $CH_3$ | 6-$CH_3$ | N—CO—NH | $C_{36}H_{49}N_7O_5$-660 |
| 22 | $CH_3$ | H | C=N—O | $C_{35}H_{46}N_6O_5$-630 |

Examples 23–28 and the compounds shown in Table II, containing a variety of representative diamine units appended to the Trp, were prepared according to the above established procedures as exemplified in Example 1 & 2 in conjunction with Intermediates 8–14 and for preparing the various required intermediates.

EXAMPLE 23

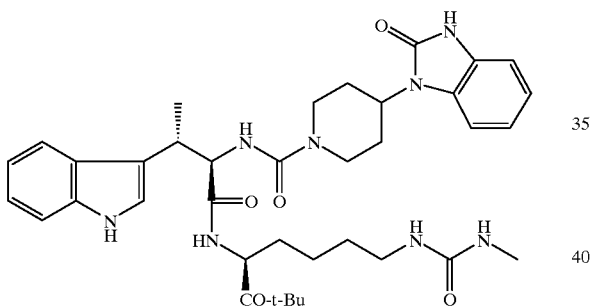

The free base product of Example 2 (100 mg, 0.155 mmol) was combined with methyl isocyanate (11 mL, 0.186 mmol) in DCM and stirred at rt overnight. The reaction mixture was concentrated to afford 90 mg of the desired product (MF/ESI-MS(M+H): $C_{37}H_{50}H_8O_6$/703).

EXAMPLE 24

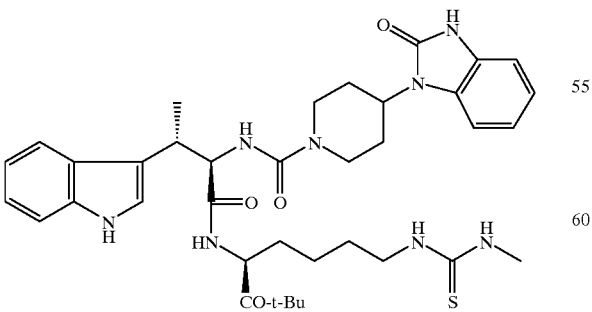

The free base product of Example 2 (100 mg, 0.155 mmol) was combined with methyl isothiocyanate (13 mL, 0.186 mmol) in DCM and stirred at rt overnight. The reaction mixture was concentrated and the crude product purified by MPLC (silica, 5% MeOH/ethyl acetate) to give 87 mg of the desired product (MF/ESI-MS(M+H): $C_{37}H_{50}N_8O_5S$/719).

EXAMPLE 25

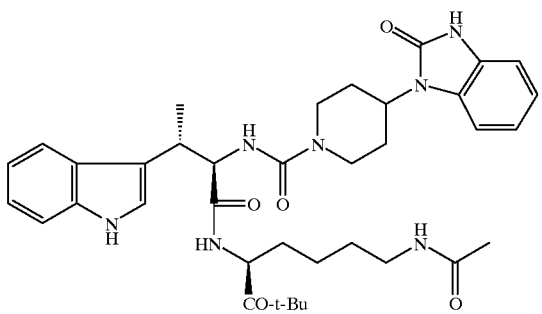

The free base product of Example 2 (100 mg, 0.155 mmol) was combined with acetic anhydride (19 mL) and NMM (34 mL, 0.37 mmol) in DCM and stirred at rt for 1 h. The reaction mixture was diluted with DCM and washed in succession with 1N HCl, saturated $NaHCO_3$ solution and brine, then the organic layer was dried over $MgSO_4$, filtered and concentrated to afford 85 mg of the desired product (MF/ESI-MS(M+H): $C_{37}H_{49}N_7O_6$/688).

EXAMPLE 26

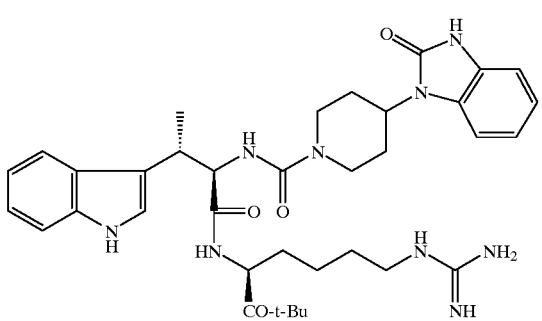

The free base product of Example 2 (100 mg, 0.155 mmol) was combined with 1H-pyrazole-1-carboxamidine hydrochloride (22.7 mg, 0.155 mmol) and DIEA (27.0 mL, 0.155 mmol) in DMF and stirred at rt overnight. Ether (~5 mL) was added to precipitate the product. The product was collected, washed with more ether and dried under vacuum to afford 123 mg of the desired product (MF/ESI-MS(M+H): $C_{36}H_{49}N_9O_5$/689).

EXAMPLE 27

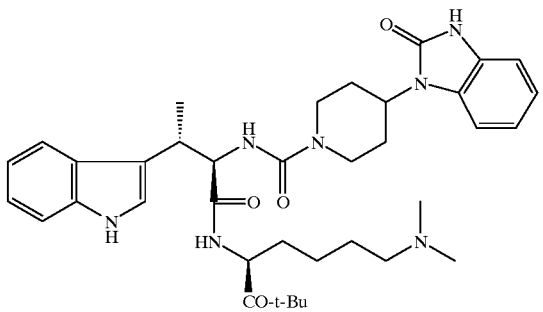

To a solution of the free base product of Example 2 (100 mg, 0.155 mmol) in ethanol (2 mL) was added formaldehyde (19 mL, 0.23 mmol) and TFA (2 mL). The mixture was stirred for 1 h at rt. Sodium cyanoborohydride (10 mg, 0.16 mmol) was added and stirring was continued at rt overnight. About 10 drops of 1 N HCl was added to quench the reaction and $N_2$ was bubbled throught the reaction mixture for ~15 sec to remove any HCN. The reaction mixture was diluted with ethyl acetate and washed with saturated $NaHCO_3$ and brine, then dried over $MgSO_4$, filtered and concentrated. Flash chromatography (silica, 2:18:80 $NH_3OH/MeOH/DCM$) afforded two fractions with the slower eluting fraction corresponding to product by ESI-MS (MF/ESI-MS(M+H): $C_{37}H_{51}N_7O_5/674$).

EXAMPLE 28

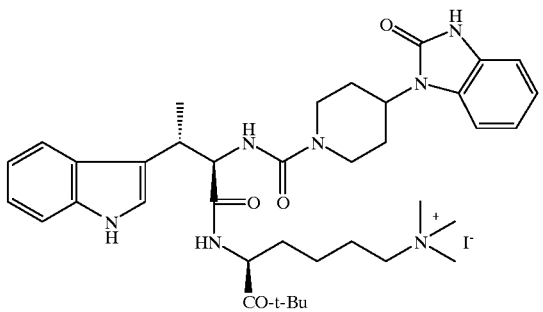

The product from Example 27 above (20 mg, 0.03 mmol) was dissolved in THF (1 mL) and treated with methyl iodide (9.2 mL, 0.15 mmol). After stirring the reaction mixture overnight, the reaction mixture was concentrated to afford 23 mg of the desired product (MF/ESI-MS(M+H): $C_{38}H_{54}N_7O_5I/688$ (M+)).

EXAMPLE 29

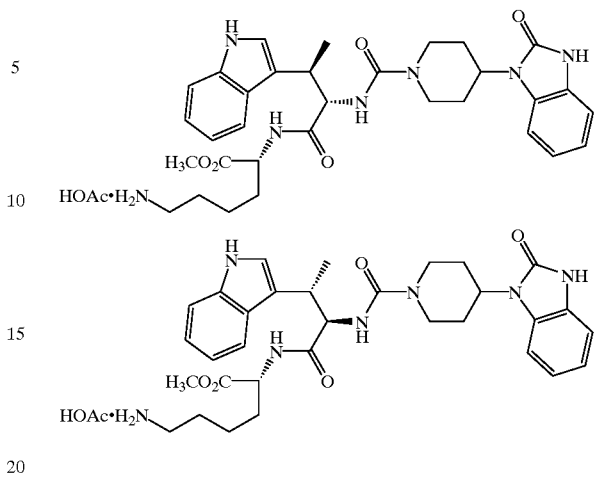

Added 500 mg of Rapp Tentagel HMPB resin (0.20 mmol/g) to a fitted tube. Washed the resin with 3×5 mL of $THF/CH_2Cl_2$. Added 2.5 mL of a 0.75M solution of DIEA in $THF/CH_2Cl_2$. Added 2.5 mL of a 0.75M solution of p-nitrophenylchloroformate in $THF/CH_2Cl_2$. Agitated the reaction for 8.5 hours. Drained the tube and washed the resin with 2×5 mL of $THF/CH_2Cl_2$. Added 5.0 mL of a 0.25M solution of 1:3 L-lysine methyl ester/DIEA and agitated for 15.5 hours. Drained the tube and washed with 3×5 mL of DMF. Added 2.5 mL of a 0.5M solution of 1:1.5 Fmoc-(RS, SR)-b-methyltryptophan/HOBt in DMF. Added 2.5 mL of a 0.5M solution of DIC/3% DMAP in DMF and agitated for 3 hours. Drained the tube, washed with 2×5 mL of DMF and repeated the acylation. Drained the tube and washed with 3×5 mL of DMF. Added 5 mL of 20% piperidine in DMF and agitated for 30 minutes. Drained the tube and washed with 3×5 mL each of DMF and $THF/CH_2Cl_2$. Added 2.5 mL of a 0.5M solution of DIEA. Added 2.5 mL of a 0.5M solution of p-nitrophenylchloroformate in $THF/CH_2Cl_2$ and agitated for 45 minutes. Drained the tube and washed with 2×5 mL of $THF/CH_2Cl_2$. Added 5.0 mL of a 0.25M solution of 1:1 4-(2-keto-1-benzimidiazolinyl)piperidine/DIEA in DMF. Agitated for 30 minutes. Drained the tube and washed with 5×5 mL each of DMF, $THF/CH_2Cl_2$, THF, $CH_2Cl_2$, isopropanol, $CH_2Cl_2$ and glacial acetic acid. Added 5 mL of glacial acetic acid under nitrogen, and heated to 40° C. for 22 hours to release the compound from the resin. Drained the tube, collecting the solution. Lyophilized this solution to afford a crude mixture of the two diastereomers. Separated the compounds by reverse-phase MPLC to afford pure products. Both compounds were pure by HPLC and gave the expected parent ion (M+1: 604) by ESI-MS.

TABLE II

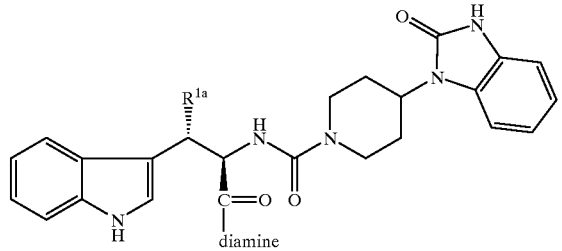

| example | $R^{1a}$ | diamine | MF ESI-MS (M + H) |
|---|---|---|---|
| 30 | H | HN~~~~~NH$_2$ | $C_{28}H_{35}N_7O_3$ 518 |
| 31 | CH$_3$ | HN~~~~~NH$_2$ | $C_{29}H_{37}N_7O_3$ 532 |
| 32 | CH$_3$ | HN~~~~~~NH$_2$ | $C_{30}H_{39}N_7O_3$ 546 |
| 33 | CH$_3$ | HN~~~~~~~NH$_2$ | $C_{31}H_{41}N_7O_3$ 560 |
| 34 | CH$_3$ | CH$_3$N~~~~NH$_2$ | $C_{30}H_{39}N_7O_3$ 546 |
| 35 | CH$_3$ | HN~(CO$_2$Me)~~~~NH$_2$ | $C_{32}H_{41}N_7O_5$ 604 |
| 36 | H | HN~(CON(CH$_3$)$_2$)~~~~NH$_2$ | $C_{32}H_{42}N_8O_4$ 603 |
| 37 | H | HN~(CONH-$i$-Pr)~~~~NH$_2$ | $C_{33}H_{44}N_8O_4$ 617 |
| 38 | H | HN~(CO$_2$$t$-Bu)~~~~NH$_2$ | $C_{34}H_{45}N_7O_5$ 631 |
| 39 | CH$_3$ | HN~(CO$_2$$t$-Bu)~~~~NH$_2$ | $C_{35}H_{47}N_7O_5$ 646 |
| 40 | CH$_3$ | HN~(CH$_2$OMe)~~~~NH$_2$ | $C_{32}H_{43}N_7O_4$ 590 |
| 41 | H | HN~(CO$_2$-$i$-pr)~~~~NH$_2$ | $C_{33}H_{43}N_7O_5$ 618 |
| 42 | CH$_3$ | CH$_3$N~(CO$_2$Me)~~~~NH$_2$ | $C_{33}H_{43}N_7O_5$ 618 |

TABLE II-continued
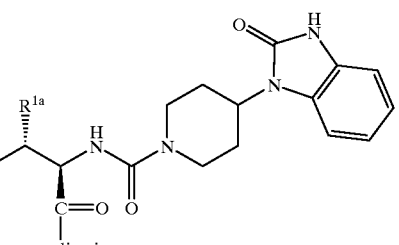
| example | R¹ᵃ | diamine | MF ESI-MS (M + H) |
|---|---|---|---|
| 43 | CH₃ | 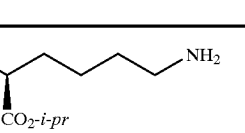 | $C_{35}H_{47}N_7O_5$ 646 |
| 44 | CH₃ | 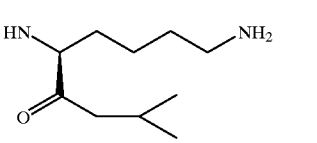 | $C_{35}H_{47}N_7O_4$ 630 |
| 45 | CH₃ | 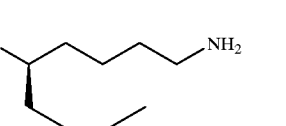 | $C_{35}H_{49}N_7O_3$ 616 |
| 46 | H | 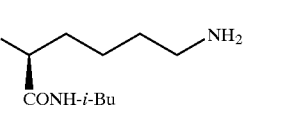 | $C_{34}H_{46}N_8O_4$ 631 |
| 47 | CH₃ | 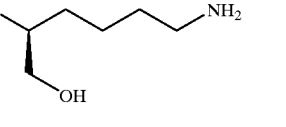 | $C_{31}H_{41}N_7O_4$ 576 |
| 48 | CH₃ | 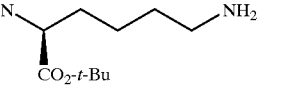 | $C_{36}H_{49}N_7O_5$ 661 |
| 49 | CH₃ | 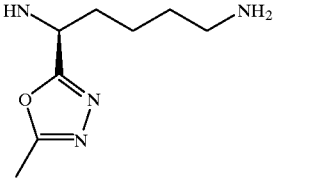 | $C_{33}H_{41}N_9O_4$ 628 |
| 50 | CH₃ | 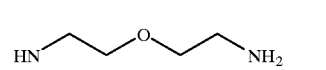 | $C_{29}H_{37}N_7O_4$ 548 |
| 51 | CH₃ | 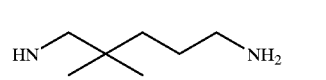 | $C_{32}H_{43}N_7O_3$ 604 |
| 52 | CH₃ | 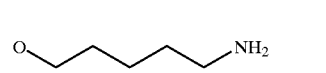 | $C_{30}H_{38}N_6O_4$ 547 |

TABLE II-continued

[Structure: tryptophan-based core with R¹ᵃ substituent, linked via urea to a piperidine bearing a 2-oxo-benzimidazole; carbonyl labeled "diamine"]

| example | R¹ᵃ | diamine | MF<br>ESI-MS (M + H) |
|---|---|---|---|
| 53 | CH₃ | [HN-CH(CH₃)-C(O)-NH-CH₂CH₂-NH₂] | |
| 54 | CH₃ | [HN-CH(iPr)-C(O)-NH-CH₂CH₂-NH₂] | C₃₂H₄₂N₈O₄<br>603 |
| 55 | CH₃ | [HN-CH(iBu)-C(O)-NH-CH₂CH₂-NH₂] | C₃₃H₄₄N₈O₄<br>617 |
| 56 | CH₃ | [HN-CH(CH₂-O-t-Bu)-C(O)-NH-CH₂CH₂-NH₂] | C₃₄H₄₆N₈O₅<br>647 |
| 57 | CH₃ | [HN-CH(CH₃)-(CH₂)₃-CH₂-NH₂] | |
| 58 | CH₃ | [HN-CH(CH₂-S-t-Bu)-C(O)-NH-CH₂CH₂-NH₂] | C₃₄H₄₆N₆O₄S<br>663 |

Additional compounds which can be made by similar methods discussed herein and known in the art are:

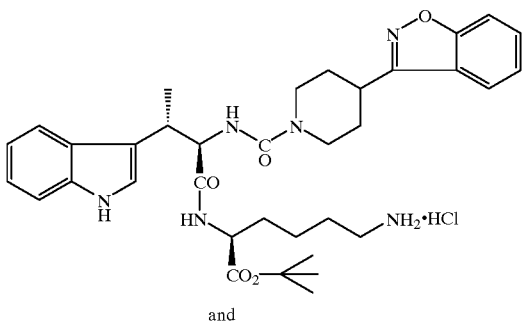

and

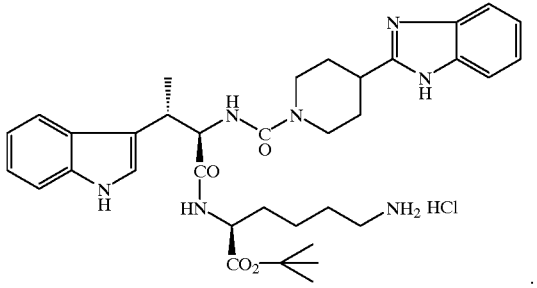

Biological Assays

The ability of compounds of the present invention to act as somatostatin agonist can be determined by the following in vitro assays, which is disclosed in Rens-Domiano, et al., Pharmacological Properties of Two Cloned Somatostatin Receptors, Mol. Pharm., 42:28–34 (1992) and incorporated herein.

Receptor Expression Constructs

Mammalian expression vectors containing full length coding sequences for hSSTR1–5 were constructed as follows: Fragments of genomic DNA carrying the various human somatostatin receptors were inserted into the multiple cloning site of pcDNA3 (Invitrogen). The fragments used were a 1.5-kb PstI-XmnI fragment for hSSTR1, 1.7-kb BamHI-HindIII fragment for hSSTR2, 2.0-kb NcoI-HindIII fragment for hSSTR3, a 1.4-kb NheI-NdeI fragment for hSSTR4, and a 3.2-kb XhoI-EcoRI fragment for hSSTR5.

Transfection

CHO-K1 cells were obtained from American Type Culture Collection (ATCC) and grown in alpha-MEM containing 10% fetal calf serum. Cells were stably transfected with DNA for all 5 hSSTRs using lipofectamine. Neomycin resistant clones were selected and maintained in medium containing G418 (400 μg ml).

Receptor binding assay

Cells were harvested 72 hr after transfection to 50 mM Tris-HCl, pH 7.8, containing 1 mM EGTA, 5 mM $MgCl_2$, 10 μg/ml leupeptin, 10 μg/ml pepstatin, 200 μg/ml bacitracin, and 0.5 μg/ml aprotinin (buffer 1) and were centrifuged at 24,000×g for 7 min at 40. The pellet was homogenized in buffer 1 using a Brinkman Polytron (setting 2.5, 30 sec). The homogenate was then centrifuged at 48,000 μg for 20 min at 4° C. The pellet was homogenized in buffer 1 and the membranes were used in the radioligand binding assay. Cell membranes (approximately 10 μg of protein) were incubated with $^{125}I$-$Tyr^{11}$-somatostatin (0.2 nM; specific activity, 2000 Ci/mmol; NEN) in the presence or absence of competing peptides, in a final volume of 200 μl, for 30 min at 25°.

Nonspecific binding was defined as the radioactivity remaining bound in the presence of 100 nM somatastatin. The binding reaction was terminated by the addition of ice-cold 50 nM Tris-HCl buffer, pH 7.8, and rapid filtration with 12 ml of ice-cold Tris HCl buffer, and the bound radioactivity was counted in a gamma scintillation spectrophotometer (80% efficiency). Data from radioligand binding studies were used to generate inhibition curves. $IC_{50}$ values were obtained from curve-fitting performed with the mathematical modeling program FITCOMP, available through the National Institutes of Health-sponsored PROPHET System.

Inhibition of forskolin-stimulated cAMP accumulation

Cells used for cAMP accumulation studies were subcultured in 12-well culture plates. COS-7 cells were transfected 72 hr before the experiments. Culture medium was removed from the wells and replaced with 500 μl of fresh medium containing 0.5 mM isobutylmethylxanthine. Cells were incubated for 20 min at 37°. Medium was then removed and replaced with fresh medium containing 0.5 mM isobutylmethylxanthine, with or without 10 μM forskolin and various concentrations of test compound. Cells were incubated for 30 min at 37°. Medium was then removed, and cells were sonicated in the wells in 500 μL of 1 N HCl and frozen for subsequent determination of cAMP content by radioimmunassay. Samples were thawed and diluted in cAMP radioimmunassay buffer before analysis of cAMP content using the commercially available assay kit from NEW/DuPont (Wilmington, Del.).

Inhibition of growth hormone release

Functional activity of the various compounds was evaluated by quantitating release of growth hormone secretion from primary cultures of rat anterior pituitary cells. Cells were isolated from rat pituitaries by enzymatic digestion with 0.2% collagenase and 0.2% hyaluronidase in Hank's balanced salt solution. The cells were suspended in culture medium and adjusted to a concentration of $1.5 \times 10^5$ cells per milliliter, and 1.0 ml of this suspension was placed in each well of a 24-well tray. Cells were maintained in a humidified 5% $CO_2$-95% air atmosphere at 37° C. for 3 to 4 days. The culture medium consisted of Dulbecco's modified Eagle's medium containing 0.37% $NaHCO_3$, 10% horse serum, 2.5% fetal bovine serum, 1% nonessential amino acids, 1% glutamine, 1% nystatin, and 0.1% gentamycin. Before testing compounds for their capacity to inhibit GH release, cells were washed twice 1.5 hours before and once more immediately before the start of the experiment with the above culture medium containing 25 mM Hepes (pH 7.4). The compounds of the insant invention were tested in quadruplicate by adding them in 1 ml of fresh medium to each well and incubating them at 37° C. for 15 min. After incubation, the medium was removed and centrifuged at 2000 g for 15 min to remove any cellular material. The supernatant fluid was removed and assayed for GH by radioimmunoassay.

The compounds of this invention were found to inhibit the binding of somatostatin to its receptor at an $IC_{50}$ of about 30 pM to about 3 μM.

What is claimed is:

1. A compound represented by formula I:

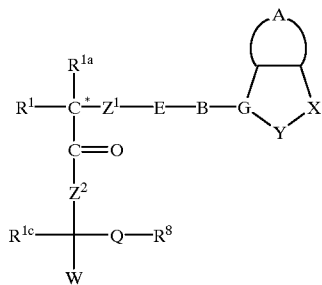

as well as pharmaceutically acceptable salts and hydrates thereof, wherein:

$R^1$ is selected from the group consisting of: -$C_{1-10}$alkyl, -aryl, aryl($C_{1-6}$alkyl)—, ($C_{3-7}$cycloalkyl)($C_{1-6}$alkyl)—, ($C_{1-5}$alkyl)-K-($C_{1-5}$alkyl)—, aryl($C_0$–$C_5$alkyl)-K-($C_1$–$C_5$alkyl)—, and ($C_{3-7}$cycloalkyl)($C_{0-5}$alkyl)-K-($C_{1-5}$alkyl)—, the alkyl portions of which being optionally substituted with by 1 to 5 halogen groups, $S(O)_m R^{2a}$, 1 to 3 of $OR^{2a}$ groups or $C(O)OR^{2a}$, aryl is selected from the group consisting of: phenyl, naphthyl, biphenyl, quinolinyl, isoquinolinyl, indolyl, azaindole, pyridyl, benzothienyl, benzofuranyl, thiazolyl and benzimidazolyl, unsubstituted or substituted with: 1 to 3 $C_{1-6}$alkyl groups, 1 to 3 halo groups, 1 to 2 —$OR^2$ groups, methylenedioxy, —$S(O)_m R^2$, 1 to 2—$CF_3$, —$OCF_3$ or $NO_2$ groups, —$N(R^2)C(O)(R^2)$, —$C(O)OR^2$, —$C(O)N(R^2)_2$, 1H-tetrazol-5-yl, —$SO_2N(R^2)_2$, —$N(R^2)SO_2$ phenyl, or —$N(R^2)SO_2R^2$;

K is selected from the group consisting of: —O—, —$S(O)_m$—, —$N(R^2)C(O)$—, —$C(O)N(R^2)$—, —$CR^2$=$CR^2$— and —C≡C—;

$R^{1a}$ is selected from the group consisting of: H and $C_{1-3}$ alkyl;

$R^{1c}$ is selected from the group consisting of: H, —$(CH_2)_q SR^2$, —$(CH_2)_q OR^2$ and $C_{1-8}$alkyl;

$R^2$ is selected from the group consisting of: H, $C_{1-8}$alkyl, $(CH_2)_t$-aryl, and $C_{3-7}$cycloalkyl, and when two $R^2$ groups are present they may be taken together with the atom to which they are attached and with any intervening atoms to represent a $C_{3-8}$ ring, said ring optionally including O, S or $NR^{3a}$, where $R^{3a}$ is hydrogen, or $C_{1-6}$alkyl, said $C_{1-6}$ alkyl being optionally substituted by OH;

and when $R^2$ represents $C_{1-8}$alkyl, it may be substituted by 1 to 5 halo groups, $S(O)_m R^{2a}$, 1 to 3 $OR^{2a}$ groups or $C(O)OR^{2a}$;

$R^{2a}$ is selected from the group consisting of: H and $C_1$–$C_8$alkyl, optionally substituted with OH;

$Z^1$ is selected from the group consisting of: —O—, —$CH^2$— and —$NR^{2a}$;

$Z^2$ is selected from the group consisting of: —O—, —$CH_2$—, —$CHR^{2b}$— and —$NR^{2b}$;

$R^{2b}$ is selected from the group consisting of: H, $C_{1-8}$alkyl, —$(CH_2)_t$-aryl, —$(CH_2)_n CO_2R^2$, —$(CH_2)_n CON(R^2)_2$, —$(CH_2)_n OH$ and —$(CH_2)_n OR^2$;

W is selected from the group consisting of: H, $C_{1-8}$alkyl, —$(CH_2)_t$-aryl, wherein aryl is selected from phenyl, biphenyl and naphthyl, —$(CH_2)_t$-heteroaryl wherein heteroaryl is selected from tetrazolyl, oxadiazolyl, thiadiazolyl, triazolyl and pyrazinyl, —$(CH_2)_q C(O)OR^2$, —$(CH_2)_q OR^2$, —$(CH_2)_q OC(O)R^2$, —$(CH_2)_q C(O)R^2$, —$(CH_2)_q C(O)(CH_2)_t$aryl, —$(CH_2)_q N(R^2)C(O)R^2$, —$(CH_2)_q C(O)N(R^2)_2$, —$(CH_2)_q N(R^2)SO_2R^2$, —$(CH_2)_q N(R^2)C(O)N(R^2)_2$, —$(CH_2)_q OC(O)N(R^2)_2$, —$(CH_2)_q N(R^2)C(O)OR^2$, —$(CH_2)_q N(R^2)SO_2N(R^2)_2$, and —$(CH_2)_q S(O)_m R^2$, wherein the heteroaryl portions thereof are optionally substituted with halo, $R^2$, $N(R^2)_2$ or $OR^2$, and $R^2$, $(CH_2)_q$ and $(CH_2)_t$ are optionally substituted with 1 to 2 of $C_{1-4}$alkyl, OH, $OC_{1-8}$ alkyl, $O(CH_2)_t$-aryl, $OC_{3-7}$ cycloalkyl, $CO_2H$, $CO_2C_{1-8}$ alkyl, $CO_2(CH_2)_t$-aryl, $CO_2C_{3-7}$ cycloalkyl or 1–3 halo groups, and said aryl portion is further optionally substituted with 1 to 3 of halogen, —$OR^2$, —$CON(R^2)_2$, —$C(O)OR^2$, $C_{1-4}$alkyl, —$S(O)_m R^2$, —$N(R^2)_2$, —$CF_3$ or 1H-tetrazol-5-yl;

Q represents a member selected from the group consisting of:

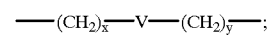

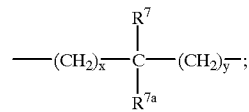

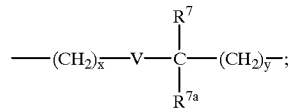

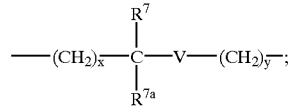

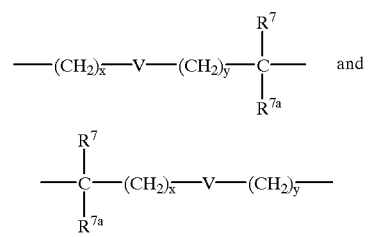

wherein x and y are independently 0, 1, 2, 3, 4, 5 or 6;

V is selected from the group consisting of —$N(R^{6a})$—, —$S(O)_m$—, —O—, —$CONR^2$— and —$NR^2CO$—;

$R^{6a}$ is selected from the group consisting of hydrogen, $C_{1-8}$alkyl, $R^2C(O)$— and $R^2SO_2$—;

$R^7$ and $R^{7a}$ are independently selected from the group consisting of hydrogen, $C_{1-6}$alkyl, $CF_3$ and aryl;

$R^8$ is selected from the group consisting of —$NR^4R^5$, —$N(=NR^9)NR^{10}$ and —$N^+(R^4)_3$;

wherein $R^4$ and $R^5$ are independently selected from the group consisting of: —$R^2$, —$C(=NR^2)N(R^2)_2$, —$C(=NCN)N(R^2)_2$, —$C(=NC(O)R^2)N(R^2)_2$, —$C(=NSO_2R^2)N(R^2)_2$, —$C(=NNO_2)NR^2$, heteroaryl, —$C(=O)N(R^2)_2$, —$C(=O)R^2$, 2,2,2-trifluoroethyl, 3,3,3-trifluoropropyl and $(CH_2)_t$-cyclopropyl, or $R^4$ and $R^5$ taken together represent —$(CH_2)_d$—$L_a$—$(CH_2)_e$— where $L_a$ is —$C(R^2)_2$—, —O—, —$S(O)_m$— or —N(R²)—, and d and e are independently 1 to 3, said heteroaryl and R² optionally substituted with 1–3 C₁₋₆alkyl groups, 1–7 halo groups, N(R²)₂, OR², N(R²)C(O)R², C(O)N(R²), OC(O)R², S(O)ₘR², CF₃, OCF₃, NO₂, N(R²)C(O)(R²), N(R²)C(O)N(R²)₂, C(O)OR², C(O)N(R²)₂, SO₂N(R²)₂, N(R²)SO₂R², or methylenedioxy;

E is selected from the group consisting of: —SO₂—, —CO(C(R²)₂)ₙ—, —C(=N—CN)—, —C(=N—NO₂)— and —C(=N—SO₂N(R²)₂—;

R⁹ and R¹⁰ are independently H or C₁₋₈alkyl, or are optionally taken together and represent a C₃₋₈ cyclic ring, which is optionally interrupted by O, S(O)ₘ or NR²ᵃ;

B is

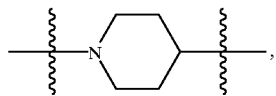

where attachment points are indicated by lines (§) external to the rings which are optionally substituted by C₁₋₆alkyl and where R² and (CH₂)_q are described above;

represents an aromatic or non-aromatic 5–6 membered ring structure wherein:

G is N;

Y is —C(O)—, —C(OR¹¹)=, —C(SR¹¹)=, —C(NR¹¹)=, —C(R¹¹)₁₋₂=, or —C(R¹¹)₂—; and

X is —N(R¹¹)— or =N—;

R¹¹ is H, C₁–C₈ alkyl, —(CH₂)_pOR², —(CH₂)_pN(R²)₂, (CH2)_pN(R²)C(O)N(R²)₂, —(CH₂)_pN(R²)C(O)R², (CH₂)₂ heteroaryl, (CH₂)_pN(R²)SO₂C₁–C₄ alkyl, —(CH₂)_pC(O)N(R²)₂, or —(CH₂)_pC(O)OR² where heteroaryl is tetrazole, oxadiazole, imidazole or triazole which is optionally substituted with R², OR² or N(R²)₂ and where p is 0–3;

A is a fused aromatic ring, having 6 atoms, and containing 0 heteroatoms, optionaly substituted with 1–3 groups selected from: C₁₋₆ alkyl, halo, —OR², N(R²)₂, methylenedioxy, —S(O)ₘR², —CF₃, —OCF₃, —NO₂, —N(R²)C(O)(R²), —C(O)OR², —C(O)N(R²)₂, -1H-tetrazol-5-yl, —SO₂N(R²)₂, —N(R²)SO₂ phenyl, N(R²)C(O)N(R²) and —N(R²)SO₂R²;

m is an integer from 0 to 2;

n is an integer from 0 to 3;

q is an integer from 0 to 3; and t is an integer from 0 to 3.

2. A compound of structural formula I':

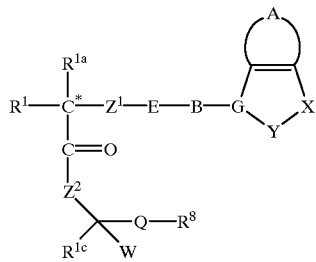

Formula I' or a pharmaceutically acceptable salt or hydrate thereof, wherein

R¹ is selected from the group consisting of: C₁–C₁₀ alkyl, aryl, aryl (C₁–C₆ alkyl), (C₃–C₇ cycloalkyl)(C₁–C₆ alkyl)—, (C₁–C₅ alkyl)-K-(C₁–C₅ alkyl)—, aryl (C₀–C₅ alkyl)-K-(C₁–C₅ alkyl)—, and (C₃–C₇ cycloalkyl)(C₀–C₅ alkyl)-K-(C₁–C₅ alkyl)—, where K is —O—, —S(O)ₘ—, —N(R²)C(O)—, —C(O)N(R²)—, —CR²=CR²—, or —C≡C—, where R² and alkyl may be further substituted by 1 to 5 halogen, S(O)ₘR²ᵃ, 1 to 3 of OR²ᵃ or C(O)OR²ᵃ, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of C₁–C₆ alkyl, 1 to 3 of halogen, 1 to 2 of —OR², methylenedioxy, —S(O)ₘR², 1 to 2 of —CF₃, —OCF₃, nitro, —N(R²)C(O)(R²), —C(O)OR², —C(O)N(R²)(R²), -1H-tetrazol-5-yl, —SO₂N(R²)(R²), —N(R²)SO₂ phenyl, or —N(R²)SO₂R²;

R² is selected from: hydrogen, C₁–C₈ alkyl, (CH₂)_t aryl, and C₃–C₇ cycloalkyl, and where two C₁–C₆ alkyl groups are present on one atom, they optionally are joined to form a C₃–C₈ cyclic ring, optionally including oxygen, sulfur or NR³ᵃ, where R³ᵃ is hydrogen, or C₁–C₆ alkyl, optionally substituted by hydroxyl;

R¹ᵃ is selected from the group consisting of hydrogen, and C₁–C₈ alkyl;

R²ᵃ is selected from the group consisting of hydrogen and C₁–C₈ alkyl, said alkyl optionally substituted by hydroxyl;

R²ᵇ is selected from hydrogen, C₁–C₈ alkyl, (CH₂)_t aryl, —(CH₂)_nCO₂R², —(CH₂)_nCON(R²)₂, —(CH₂)_nOH or —(CH₂)_nOR²;

R¹ᶜ is selected from the group consisting of hydrogen, —(CH₂)_qSR², —(CH₂)_qOR² and C₁–C₈ alkyl;

Z¹ is selected from the group consisting of —O—, —CH²— and —NR²ᵃ;

Z² is selected from the group consisting of —O—, —CH₂—, —CHR²ᵇ— and —NR²ᵇ;

W is selected from the group consisting of: hydrogen, C₁–C₈ alkyl, (CH2)_t aryl, —(CH₂)_qC(O)OR², —(CH₂)_q OR², —(CH₂)_qOC(O)R², —(CH₂)_qC(O)R², —(CH₂)_q C(O)(CH₂)_qaryl, —(CH₂)_qC(O)N(R²)₂, —(CH₂)_qN(R²)C(O)R², —(CH₂)_qC(O)N(R²)₂, —(CH₂)_qN(R²)SO₂R², —(CH₂)_qN(R²)C(O)N(R²)₂, —(CH₂)_qOC(O)N(R²)₂, —(CH₂)_qN(R²)C(O)OR², —(CH₂)_qN(R²)SO₂N(R²)₂, —(CH₂)_qS(O)ₘR², and (CH₂)_t heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ is optionally substituted with 1 to 2 $C_1$–$C_4$ alkyl, $OR^2$, $C(O)OR^2$, 1–3 halo and said aryl is optionally substituted with 1 to 3 halogen, —$OR^2$, —$CON(R^2)_2$, —$C(O)OR^2$, $C_1$–$C_4$ alkyl, —$S(O)_mR^2$, $N(R^2)_2$, $CF_3$ or 1H-tetrazol-5-yl;

Q is selected from the group consisting of:

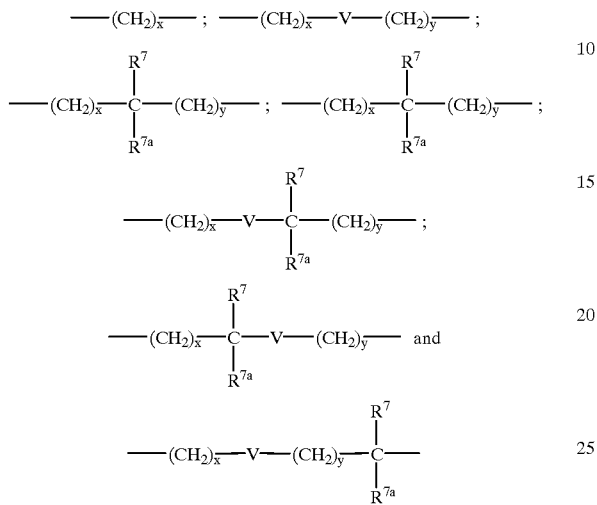

where x and y are independently 0, 1, 2, 3, 4, 5, 6;

V is selected from the group consisting of —$N(R^{6a})$—, —$S(O)_m$—, —O—, —$CONR^2$— and —$NR^2CO$—;

$R^{6a}$ is selected from the group consisting of hydrogen or $C_1$–$C_8$ alkyl, $R^2CO$— and $R^2SO_2$—;

$R^7$ and $R^{7a}$ are independently selected from the group consisting of hydrogen, $C_1$–$C_6$ alkyl, trifluoromethyl and aryl;

R8 is selected from the group consisting of

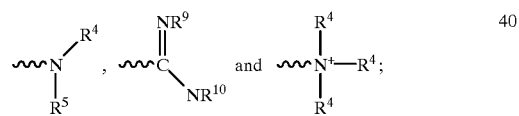

$R^4$ and $R^5$ are independently selected from the group consisting of $R^2$, —$C(=NR^2)N(R^2)_2$, —$C(=NCN)N(R^2)_2$, —$C(=NC(O)R^2)N(R^2)_2$, $C(=NSO_2R^2)N(R^2)_2$, —$C(=NNO_2)NR^2$, heteroaryl, —$C(=O)N(R^2)_2$, —$C(=O)R^2$, 2,2,2-trifluoroethyl, 3,3,3-trifluoropropyl, $(CH_2)_t$ cyclopropyl, or $R^4$ and $R^5$ may be taken together to form —$(CH_2)_d$—$L_a(CH_2)_e$— where $L_a$ is —$C(R^2)_2$—, —O—, —$S(O)_m$— or —$N(R^2)$—, d and e are independently 1 to 3, said heteroaryl and $R^2$ optionally substituted with 1–3 groups of $C_{1-6}$ alkyl, 1–7 halo, $N(R^2)_2$, $OR^2$, $N(R^2)C(O)R^2$, $C(O)N(R^2)$, $OC(O)R^2$, $S(O)_mR^2$, $CF_3$, $OCF_3$, $NO_2$, $N(R^2)C(O)(R^2)$, $N(R^2)C(O)N(R^2)_2$, $C(O)OR^2$, $C(O)N(R^2)_2$, $SO_2N(R^2)_2$, $N(R^2)SO_2R^2$, or methylenedioxy;

E is selected from the group consisting of —$SO_2$—, —$COC(R^2)N$—, —$C(=N$—$CN)$—, —$C(=N$—$NO_2)$— and —$C(=N$—$SO_2N(R^2)_2$—;

$R^9$ & $R^{10}$ are independently H, $C_{1-8}$ alkyl or optionally may be taken together to form a $C_{3-8}$ cyclic ring, which can optionally be interrupted by oxygen, $S(O)_m$ or $NR^{2a}$;

B is

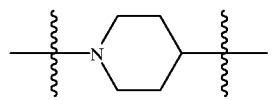

where attachment points are indicated by lines (§) external to the rings which are optionally substituted by $C_1$–$C_6$ alkyl and where $R^2$ and $(CH_2)_q$ are described above;

G is N;

Y is —$C(O)$—, —$C(OR^{11})=$, —$C(SR^{11})=$, —$C(NR^{11})=$, —$C(R^{11})_k=$, or —$C(R^{11})_2$—;

X is —$N(R^{11})$— or =N—;

$R^{11}$ is H, $C_1$–$C_8$ alkyl, —$(CH_2)_pOR^2$, —$(CH_2)_pN(R^2)_2$, $(CH2)_pN(R^2)C(O)N(R^2)_2$, —$(CH_2)_pN(R^2)C(O)R^2$, $(CH_2)_2$ heteroaryl, $(CH_2)_pN(R^2)SO_2C_1$–$C_4$ alkyl, —$(CH_2)_pC(O)N(R^2)_2$, or —$(CH_2)_pC(O)OR^2$ where heteroaryl is tetrazole, oxadiazole, imidazole or triazole which is optionally substituted with $R^2$, $OR^2$ or $N(R^2)_2$ and where p is 0–3;

A is a fused aryl group containing 6 atoms and being optionally substituted with 1–3 groups of $C_1$–$C_6$ alkyl, halogen, —$OR^2$, $N(R^2)_2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, -1H-tetrazol-5-yl, —$SO_2N(R^2)_2$, —$N(R^2)SO_2$ phenyl, $N(R^2)C(O)N(R^2)$ or —$N(R^2)SO_2R^2$, in the case where the ring is asymmetrical, all isomers are included;

m is an integer from 0 to 2;

n is an integer from 0 to 3;

q is an integer from 0 to 3; and t is an integer from 0 to 3.

3. A compound according to claim 1 having a structural formula Ib:

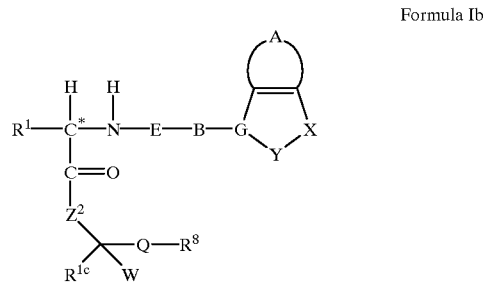

Formula Ib or a pharmaceutically acceptable salt or hydrate thereof, wherein:

$R^1$ is selected from the group consisting of: $C_1$–$C_{10}$ alkyl, aryl, aryl ($C_1$–$C_6$ alkyl), ($C_3$–$C_7$ cycloalkyl)($C_1$–$C_6$ alkyl)—, ($C_1$–$C_5$ alkyl)-K-($C_1$–$C_5$ alkyl)—, aryl ($C_0$–$C_5$ alkyl)-K-($C_1$–$C_5$ alkyl)—, and ($C_3$–$C_7$ cycloalkyl)($C_0$–$C_5$ alkyl)-K-($C_1$–$C_5$ alkyl)—, where K is —O—, —$S(O)_m$—, —$N(R^2)C(O)$—, —$C(O)N(R^2)$—, —$CR^2=CR^2$—, or —C≡C—, where $R^2$ and alkyl may be further substituted by 1 to 5 halogen, $S(O)_mR^{2a}$, 1 to 3 of $OR^{2a}$ or $C(O)OR^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_m R^2$, 1 to 2 of —$CF_3$, —$OCF_3$, nitro, —$N(R^2)C(O)(R^2)$, —$C(O)OR^2$, —$C(O)N(R^2)(R^2)$, -1H-tetrazol-5-yl, —$SO_2 N(R^2)(R^2)$, —$N(R^2)SO_2$ phenyl, or —$N(R^2)SO_2 R^2$;

$R^2$ is selected from: hydrogen, $C_1$–$C_8$ alkyl, $(CH_2)_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or $NR^{3a}$, where $R^{3a}$ is hydrogen, or $C_1$–$C_6$ alkyl, optionally substituted by hydroxyl;

$R^{2a}$ is selected from the group consisting of hydrogen and $C_1$–$C_8$ alkyl, said alkyl optionally substituted by hydroxyl;

$Z^2$ is selected from the group consisting of —O—, —CH2—, —$CHR^{2b}$— and —$NR^{2b}$;

$R^{2b}$ is selected from hydrogen, $C_1$–$C_8$ alkyl, $(CH_2)_t$ aryl, —$(CH_2)_n CO_2 R^2$, —$(CH_2)_n CON(R^2)_2$, —$(CH_2)_n OH$ or —$(CH_2)_n OR^2$;

$R^{1c}$ is selected from the group consisting of hydrogen, —$(CH_2)_q SR^2$, —$(CH_2)_q OR^2$ and $C_1$–$C_8$ alkyl;

W is selected from the group consisting of: hydrogen, $C_1$–$C_8$ alkyl, $(CH2)_t$ aryl, —$(CH_2)_q C(O)OR^2$, —$(CH_2)_q OR^2$, —$(CH_2)_q OC(O)R^2$, —$(CH_2)_q C(O)R^2$, —$(CH_2)_q C(O)(CH_2)_t aryl$, —$(CH_2)_q C(O)N(R^2)_2$, —$(CH_2)_q N(R^2)C(O)R^2$, —$(CH_2)_q C(O)N(R^2)_2$, —$(CH_2)_q N(R^2)SO_2 R^2$, —$(CH_2)_q N(R^2)C(O)N(R^2)_2$, —$(CH_2)_q OC(O)N(R^2)_2$, —$(CH_2)_q N(R^2)C(O)OR^2$, —$(CH_2)_q N(R^2)SO_2 N(R^2)_2$, —$(CH_2)_q S(O)_m R^2$, and $(CH_2)_t$ heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ is optionally substituted with 1 to 2 $C_1$–$C_4$ alkyl, $OR^2$, $C(O)OR^2$, 1–3 halo and said aryl is optionally substituted with 1 to 3 halogen, —$OR^2$, —$CON(R^2)_2$, —$C(O)OR^2$, $C_1$–$C_4$ alkyl, —$S(O)_m R^2$, $N(R^2)_2$, $CF_3$ or 1H-tetrazol-5-yl;

Q is selected from the group consisting of:

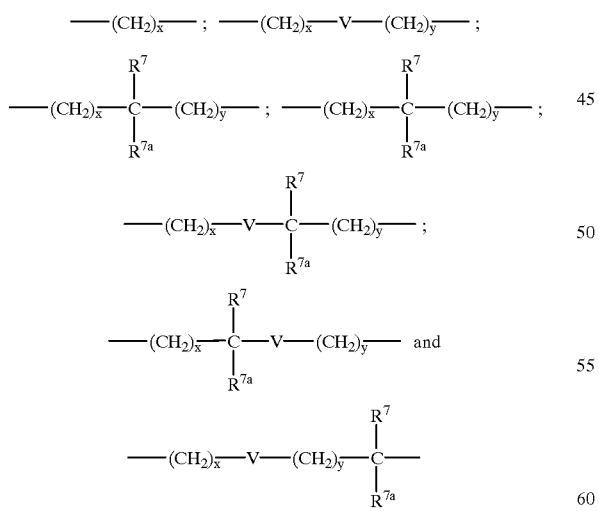

where x and y are independently 0, 1, 2, 3, 4, 5, 6;

V is selected from the group consisting of —$N(R^{6a})$—, —$S(O)_m$—, —O—, —$CONR^2$— and —$NR^2 CO$—;

$R^{6a}$ is selected from the group consisting of hydrogen or $C_1$–$C_8$ alkyl, $R^2 CO$— and $R^2 SO_2$—;

$R^7$ and $R^{7a}$ are independently selected from the group consisting of hydrogen, $C_1$–$C_6$ alkyl, trifluoromethyl and aryl;

R8 is selected from the group consisting of

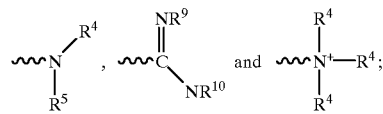

$R^4$ and $R^5$ are independently selected from the group consisting of $R^2$, —$C(=NR^2)N(R^2)_2$, —$C(=NCN)N(R^2)_2$, —$C(=NC(O)R^2)N(R^2)_2$, $C(=NSO_2 R^2)N(R^2)_2$, —$C(=NNO_2)NR^2$, heteroaryl, —$C(=O)N(R^2)_2$, —$C(=O)R^2$, 2,2,2-trifluoroethyl, 3,3,3-trifluoropropyl, $(CH_2)_t$ cyclopropyl, or $R^4$ and $R^5$ may be taken together to form —$(CH_2)_d$—$L_a (CH_2)_e$— where $L_a$ is —$C(R^2)_2$—, —O—, —$S(O)_m$— or —$N(R^2)$—, d and e are independently 1 to 3, said heteroaryl and $R^2$ optionally substituted with 1–3 groups of $C_{1-6}$ alkyl, 1–7 halo, $N(R^2)_2$, $OR^2$, $N(R^2)C(O)R^2$, $C(O)N(R^2)$, $OC(O)R^2$, $S(O)_m R^2$, $CF_3$, $OCF_3$, $NO_2$, $N(R^2)C(O)(R^2)$, $N(R^2)C(O)N(R^2)_2$, $C(O)OR^2$, $C(O)N(R^2)_2$, $SO_2 N(R^2)_2$, $N(R^2)SO_2 R^2$, or methylenedioxy;

E is selected from the group consisting of —$SO_2$—, —$COC(R^2)N$—, —$C(=N—CN)$—, —$C(=N—NO_2)$— and —$C(=N—SO_2 N(R^2)_2$—;

$R^9$ & $R^{10}$ are independently H, $C_{1-8}$ alkyl or optionally may be taken together to form a $C_{3-8}$ cyclic ring, which can optionally be interrupted by oxygen, $S(O)_m$ or $NR^{2a}$;

B is

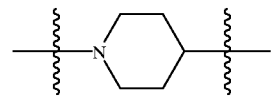

where attachment points are indicated by lines (§) external to the rings which are optionally substituted by $C_1$–$C_6$ alkyl and where $R^2$ and $(CH_2)_q$ are described above;

G is N;

Y is —$C(O)$—, —$C(OR^{11})$=, —$C(SR^{11})$=, —$C(NR^{11})$=, —$C(R^{11})_k$=, or —$C(R^{11})_2$—;

X is —$N(R^{11})$— or =N—;

$R^{11}$ is H, $C_1$–$C_8$ alkyl, —$(CH_2)_p OR^2$, —$(CH_2)_p N(R^2)_2$, $(CH2)_p N(R^2)C(O)N(R^2)_2$, —$(CH_2)_p N(R^2)C(O)R^2$, $(CH_2)_2$ heteroaryl, $(CH_2)_p N(R^2)SO_2 C_1$–$C_4$ alkyl, —$(CH_2)_p C(O)N(R^2)_2$, or —$(CH_2)_p C(O)OR^2$ where heteroaryl is tetrazole, oxadiazole, imidazole or triazole which is optionally substituted with $R^2$, $OR^2$ or $N(R^2)_2$ and where p is 0–3;

A is a fused aryl group containing 6 atoms and being optionally substituted with 1–3 groups of $C_1$–$C_6$ alkyl, halogen, —$OR^2$, $N(R^2)_2$, methylenedioxy, —$S(O)_m R^2$, —$CF_3$, —$OCF_3$, nitro, —$N(R^2)C(O)(R^2)$, —$C(O)OR^2$, —$C(O)N(R^2)_2$, -1H-tetrazol-5-yl, —$SO_2 N(R^2)_2$, —$N(R^2)SO_2$ phenyl, $N(R^2)C(O)N(R^2)$ or —$N(R^2)SO_2 R^2$, in the case where the ring is asymmetrical, all isomers are included;

m is an integer from 0 to 2;

n is an integer from 0 to 3;
q is an integer from 0 to 3; and
t is an integer from 0 to 3.

4. A compound according to claim 1 having structural Formula Ic:

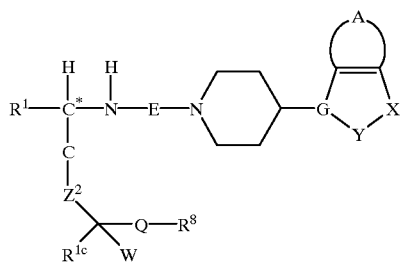

Formula Ic or a pharmaceutically acceptable salt or hydrate thereof, wherein:

$R^1$ is selected from the group consisting of: $C_1$–$C_{10}$ alkyl, aryl, aryl ($C_1$–$C_6$ alkyl), ($C_3$–$C_7$ cycloalkyl)($C_1$–$C_6$ alkyl)—, ($C_1$–$C_5$ alkyl)-K-($C_1$–$C_5$ alkyl)—, aryl ($C_0$–$C_5$ alkyl)-K-($C_1$–$C_5$ alkyl)—, and ($C_3$–$C_7$ cycloalkyl)($C_0$–$C_5$ alkyl)-K-($C_1$–$C_5$ alkyl)—, where K is —O—, —S(O)$_m$—, —N($R^2$)C(O)—, —C(O)N ($R^2$)—, —CR$^2$=CR$^2$—, or —C≡C—, where $R^2$ and alkyl may be further substituted by 1 to 5 halogen, S(O)$_m$R$^{2a}$, 1 to 3 of OR$^{2a}$ or C(O)OR$^{2a}$, and aryl is selected from: phenyl, naphthyl, biphenyl, quinolinyl, isoquinolinyl, indolyl, azaindole, pyridyl, benzothienyl, benzofuranyl, thiazolyl, and benzimidazolyl, and where the aryl is unsubstituted or substituted with a substitutent selected from: 1 to 3 of $C_1$–$C_6$ alkyl, 1 to 3 of halogen, 1 to 2 of —OR$^2$, methylenedioxy, —S(O)$_m$R$^2$, 1 to 2 of —CF$_3$, —OCF$_3$, nitro, —N(R$^2$)C(O)(R$^2$), —C(O)OR$^2$, —C(O)N(R$^2$) (R$^2$), -1H-tetrazol-5-yl, —SO$_2$N(R$^2$)(R$^2$), —N(R$^2$)SO$_2$ phenyl, or —N(R$^2$)SO$_2$R$^2$;

$R^2$ is selected from: hydrogen, $C_1$–$C_8$ alkyl, (CH$_2$)$_t$ aryl, and $C_3$–$C_7$ cycloalkyl, and where two $C_1$–$C_6$ alkyl groups are present on one atom, they optionally are joined to form a $C_3$–$C_8$ cyclic ring, optionally including oxygen, sulfur or NR$^{3a}$, where R$^{3a}$ is hydrogen, or $C_1$–$C_6$ alkyl, optionally substituted by hydroxyl;

$R^{2a}$ is selected from the group consisting of hydrogen and $C_1$–$C_8$ alkyl, said alkyl optionally substituted by hydroxyl;

$Z^2$ is selected from the group consisting of —O—, —CH$_2$—, —CHR$^{2b}$— and —NR$^{2b}$;

$R^{2b}$ is selected from hydrogen, $C_1$–$C_8$ alkyl, (CH$_2$)$_t$ aryl, —(CH$_2$)$_n$CO$_2$R$^2$, —(CH$_2$)$_n$CON(R$^2$)$_2$, —(CH$_2$)$_n$OH or —(CH$_2$)$_n$OR$^2$;

$R^{1c}$ is selected from the group consisting of hydrogen, —(CH$_2$)$_q$SR$^2$, —(CH$_2$)$_q$OR$^2$ and $C_1$–$C_8$ alkyl;

W is selected from the group consisting of: hydrogen, $C_1$–$C_8$ alkyl, (CH2)$_t$ aryl, —(CH$_2$)$_q$C(O)OR$^2$, —(CH$_2$)$_q$ OR$^2$, —(CH$_2$)$_q$OC(O)R$^2$, —(CH$_2$)$_q$C(O)R$^2$, —(CH$_2$)$_q$ C(O)(CH$_2$)$_t$aryl, —(CH$_2$)$_q$C(O)N(R$^2$)$_2$, —(CH$_2$)$_q$N(R$^2$)C(O)R$^2$, —(CH$_2$)$_q$C(O)N(R$^2$)$_2$, —(CH$_2$)$_q$N(R$^2$)SO$_2$R$^2$, —(CH$_2$)$_q$N(R$^2$)C(O)N(R$^2$)$_2$, —(CH$_2$)$_q$OC(O)N(R$^2$)$_2$, —(CH$_2$)$_q$N(R$^2$)C(O)OR$^2$, —(CH$_2$)$_q$N(R$^2$)SO$_2$N(R$^2$)$_2$, —(CH$_2$)$_q$S(O)$_m$R$^2$, and (CH$_2$)$_t$ heteroaryl where the heteroaryl is preferably tetrazole, oxadiazole, thiadiazole, triazole or pyrazine, which is optionally substituted with R$^2$, N(R$^2$)$_2$ and OR$^2$, where R$^2$, (CH$_2$)$_q$ and (CH$_2$)$_t$ are optionally substituted with 1 to 2 $C_1$–$C_4$ alkyl, OR$^2$, C(O)OR$^2$, 1–3 halo and said aryl is optionally substituted with 1 to 3 halogen, —OR$^2$, —CON (R$^2$)$_2$, —C(O)OR$^2$, $C_1$–$C_4$ alkyl, —S(O)$_m$R$^2$, N(R$^2$)$_2$, CF$_3$ or 1H-tetrazol-5-yl;

Q is selected from the group consisting of: —(CH$_2$)$_3$—, —(CH$_2$)$_4$—, —(CH$_2$)$_5$—, —CH$_2$—S—(CH$_2$)$_2$—,— CH$_2$—O—(CH$_2$)$_2$—,

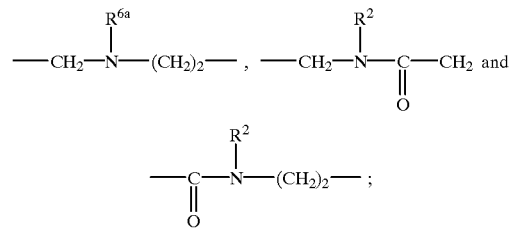

$R^{6a}$ is selected from the group consisting of hydrogen or $C_1$–$C_8$ alkyl, R$^2$CO— and R$^2$SO$_2$—;

R8 is selected from the group consisting of

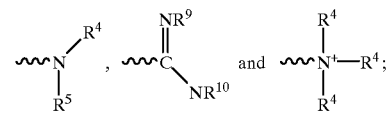

$R^4$ and $R^5$ are independently selected from the group consisting of R$^2$, —C(=NR$^2$)N(R$^2$)$_2$, —C(=NCN)N (R$^2$)$_2$, —C(=NC(O)R$^2$)N(R$^2$)$_2$, C(=NSO$_2$R$^2$)N(R$^2$)$_2$, —C(=NNO$_2$)NR$^2$, heteroaryl, —C(=O)N(R$^2$)$_2$, —C(=O)R$^2$, 2,2,2-trifluoroethyl, 3,3,3-trifluoropropyl, (CH$_2$)$_t$ cyclopropyl, or R$^4$ and R$^5$ may be taken together to form —(CH$_2$)$_d$—L$_a$(CH$_2$)$_e$— where L$_a$ is —C(R$^2$)$_2$—, —O—, —S(O)$_m$— or —N(R$^2$)—, d and e are independently 1 to 3, said heteroaryl and R$^2$ optionally substituted with 1–3 groups of $C_{1-6}$ alkyl, 1–7 halo, N(R$^2$)$_2$, OR$^2$, N(R$^2$)C (O)R$^2$, C(O)N(R$^2$), OC(O)R$^2$, S(O)$_m$R$^2$, CF$_3$, OCF$_3$, NO$_2$, N(R$^2$)C(O)(R$^2$), N(R$^2$)C(O)N(R$^2$)$_2$, C(O)OR$^2$, C(O)N(R$^2$)$_2$, SO$_2$N(R$^2$)$_2$, N(R$^2$)SO$_2$R$^2$, or methylenedioxy;

$R^9$ & $R^{10}$ are independently H, $C_{1-8}$ alkyl or optionally may be taken together to form a $C_{3-8}$ cyclic ring, which can optionally be interrupted by oxygen, S(O)$_m$ or NR$^{2a}$;

G is N;

Y is —C(O)—, —C(OR$^{11}$)=, —C(SR$^{11}$)=, —C(NR$^{11}$)=, —C(R$^{11}$)$_k$=, or —C(R$^{11}$)$_2$—;

X is —N(R$^{11}$)— or =N—;

$R^{11}$ is H, $C_1$–$C_8$ alkyl, —(CH$_2$)$_p$OR$^2$, —(CH$_2$)$_p$N(R$^2$)$_2$, (CH2)$_p$N(R$^2$)C(O)N(R$^2$)$_2$, —(CH$_2$)$_p$N(R$^2$)C(O)R$^2$, (CH$_2$)$_2$ heteroaryl, (CH$_2$)$_p$N(R$^2$)SO$_2$C$_1$–C$_4$ alkyl, —(CH$_2$)$_p$C(O)N(R$^2$)$_2$, or —(CH$_2$)$_p$C(O)OR$^2$ where heteroaryl is tetrazole, oxadiazole, imidazole or triazole which is optionally substituted with R$^2$, OR$^2$ or N(R$^2$)$_2$ and where p is 0–3;

A is: a fused benzene, optionally substituted with: 1 to 3 of $C_1$–$C_{15}$ alkyl, halogen, —OR$^2$, N(R$^2$)$_2$, methylenedioxy, —S(O)$_m$R$^2$, —CF$_3$, —OCF$_3$, nitro, —N(R$^2$)C(O)(R$^2$), —C(O)OR$^2$, —C(O)N(R$^2$)$_2$, -1H-tetrazol-5-yl, —SO$_2$N(R$^2$)$_2$, —N(R$^2$)SO$_2$ phenyl, or —N(R²)SO₂R², in the case where the ring is asymmetrical all isomers are included;
m is an integer from 0 to 2;
n is an integer from 0 to 3;
q is an integer from 0 to 3, and
t is an integer from 0 to 3.
5. A compound according to claim 1 having the Formula Id:
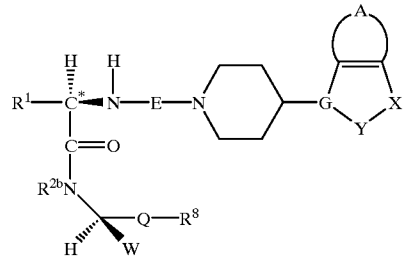
Formula Id
or a pharmaceutically acceptable salt or hydrate thereof, wherein:
R¹ is selected from the group consisting of:
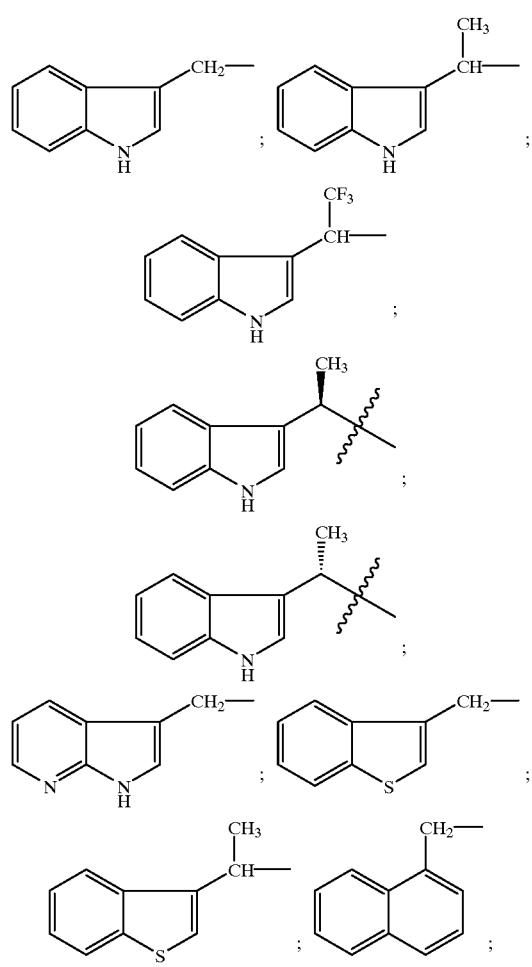
-continued
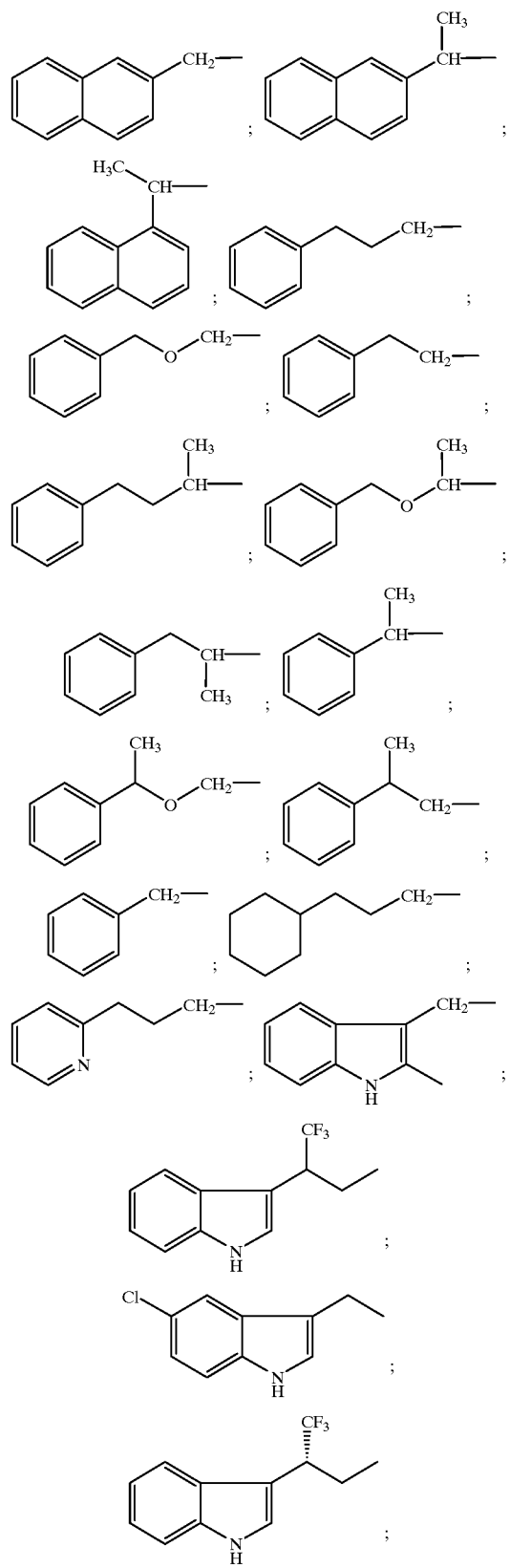

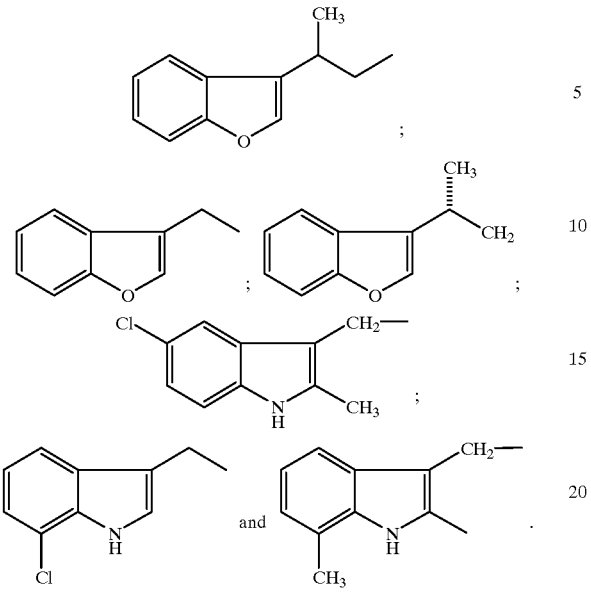

where the aryl is unsubstituted or substituted with a substitutent selected from: 1 to 3 of $C_1$–$C_6$ alkyl, 1 to 3 of halogen, 1 to 2 of —$OR^2$, methylenedioxy, —$S(O)_m$ $R^2$, 1 to 2 of —$CF_3$, —$OCF_3$, nitro, —$N(R^2)$ $C(O)(R^2)$, —$C(O)OR^2$, —$C(O)N(R^2)(R^2)$, -1H-tetrazol-5-yl, —$SO_2N(R^2)(R^2)$, —$N(R^2)SO_2$ phenyl, or —$N(R^2)SO_2R^2$;

$R^2$ is selected from: hydrogen, methyl, ethyl, propyl, isopropyl, butyl, isobutyl, t-butyl;

$R^{2b}$ is selected from hydrogen $C_1$–$C_4$ alkyl, $(CH_2)_n$ aryl, —$(CH_2)_nCO_2R^2$, —$(CH_2)_nCON(R^2)_2$, —$(CH_2)_nOH$ or —$(CH_2)_nOR^2$;

W is selected from the group consisting of: hydrogen, $C_1$–$C_8$ alkyl, $(CH2)_t$ aryl, —$(CH_2)_qC(O)OR^2$, —$(CH_2)_q$ $OR^2$, —$(CH_2)_qOC(O)R^2$, —$(CH_2)_qC(O)R^2$, —$(CH_2)_q$ $C(O)(CH_2)_t$aryl, —$(CH_2)_qC(O)N(R^2)_2$, —$(CH_2)_qN(R^2)C(O)R^2$, —$(CH_2)_qN(R^2)SO_2R^2$, —$(CH_2)_qN(R^2)C(O)N(R^2)_2$, —$(CH_2)_qOC(O)N(R^2)_2$, —$(CH_2)_qN(R^2)C(O)OR^2$, —$(CH_2)_qN(R^2)SO_2N(R^2)_2$, —$(CH_2)_qS(O)_mR^2$, and $(CH_2)_t$ heteroaryl where the heteroaryl is preferably tetrazole, oxadiazole, thiadiazole, triazole or pyrazine, which is optionally substituted with $R^2$, $N(R^2)_2$ and $OR^2$, where $R^2$, $(CH_2)_q$ and $(CH_2)_t$ is optionally substituted with 1 to 2 $C_1$–$C_4$ alkyl, $OR^2$, $C(O)OR^2$, 1–3 halo and said aryl is optionally substituted with 1 to 3 halogen, —$OR^2$, —$CON$ $(R^2)_2$, —$C(O)OR^2$, $C_1$–$C_4$ alkyl, —$S(O)_mR^2$, $N(R^2)_2$, $CF_3$ or 1H-tetrazol-5-yl;

Q is selected from the group consisting of: —$(CH_2)_3$—, —$(CH_2)_4$—, —$(CH_2)5$—, —$CH_2$—S—$(CH_2)_2$—,—$CH_2$—O—$(CH_2)_2$—,

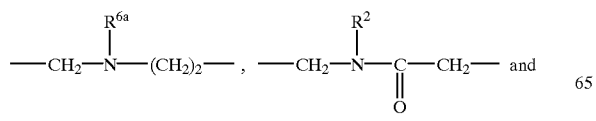

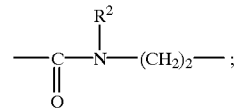

$R^{6a}$ is selected from the group consisting of hydrogen or $C_1$–$C_8$ alkyl, $R^2CO$— and $R^2SO_2$—;

R8 is

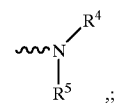

$R^4$ and $R^5$ are independently selected from the group consisting of $R^2$, —$C(=NR^2)N(R^2)_2$, heteroaryl,—$C(=S)N(R^2)_2$, —$C(=O)N(R^2)_2$, —$C(=O)R^2$, 2,2,2-trifluoroethyl, 3,3,3-trifluoropropyl, $(CH_2)_t$ cyclopropyl, and the heteroaryl is pyridyl or imidazolyl;

E is selected from the group consisting of—CO—, —C(=N—CN)—, and —$SO_2$—;

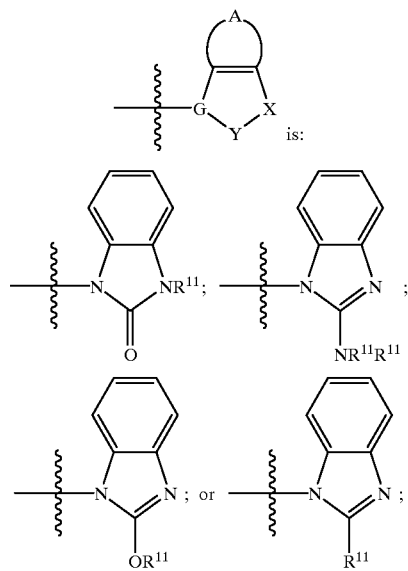

where the aromatic can be optionally substituted with 1–3 groups of $C_1$–$C_6$ alkyl, halogen, —$OR^2$, $N(R^2)_2$, methylenedioxy, —$S(O)_mR^2$, —$CF_3$, —$OCF_3$, nitro, —$N(R^2)C(O)(R^2)$, —$C(O)OR^2$, —$C(O)N(R^2)_2$, -1H-tetrazol-5-yl, —$SO_2N(R^2)_2$, —$N(R^2)SO_2$ phenyl, $N(R^2)C(O)N(R^2)$ or —$N(R^2)SO_2R^2$;

$R^{11}$ is H, $C_1$–$C_8$ alkyl, $CF_3$, $CH_2CF_3$, —$(CH_2)_pOR^2$, —$(CH_2)_pN(R^2)_2$, $(CH2)_pN(R^2)C(O)N(R^2)_2$, —$(CH_2)_p$ $N(R^2)C(O)R^2$, $(CH_2)_p$ heteroaryl, $(CH_2)_pN(R^2)$ $SO_2C_1$–$C_4$ alkyl, —$(CH_2)_pC(O)N(R^2)_2$, or —$(CH_2)_pC(O)OR^2$ where heteroaryl is tetrazole, oxadiazole, imidazole or triazole which is optionally substituted with $R^2$, $OR^2$ or $N(R^2)_2$ and where p is 0–3;

m is an integer from 0 to 2;
n is an integer from 0 to 3;
q is an integer from 0 to 3, and
t is an integer from 0 to 3.

6. A compound according to claim 1 having the structural Formula Ie:

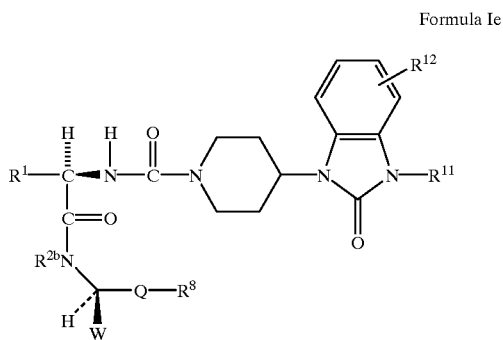

Formula Ie or a pharmaceutically acceptable salt or hydrate thereof; wherein:

$R^1$ is selected from the group consisting of:

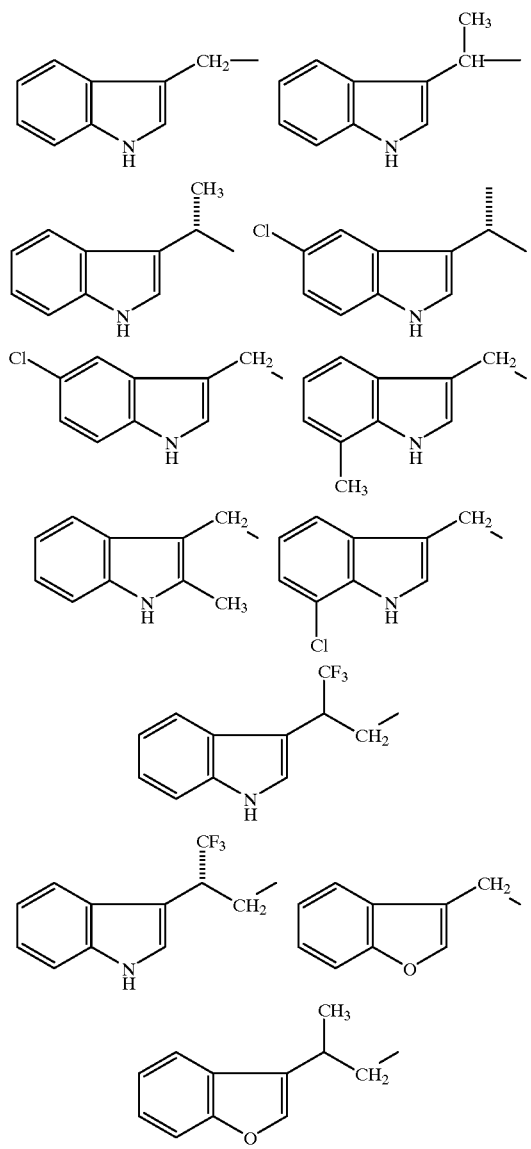

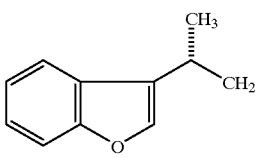

wherein the aryl groups shown above may be further substituted by 1 to 3 of $C_1$–$C_6$ alkyl, 1 to 3 of halogen, 1 to 2 of $OR^2$, $S(O)_m R^2$, or 1 to 2 of $CF_3$;

$R^2$ is selected from hydrogen or $C_1$–$C_6$ alkyl;

$R^{2b}$ is selected from hydrogen, $C_1$–$C_4$ alkyl, $(CH_2)_n$ phenyl or $(CH_2)_n$—$OR^2$;

W is selected from the group consisting of hydrogen, $C_1$–$C_4$ alkyl, $(CH_2)_2 OR^2$, $(CH_2)_q C(O)N(R^2)_2$, $(CH_2)_q C(O)OR_2$ or oxadiazole optionally substituted by $R^2$, $N(R^2)_2$ or $OR^2$;

Q is selected from the group consisting of —$(CH_2)_3$—, —$(CH_2)_4$—, —$(CH_2)_5$—, —$CH_2S$—$(CH_2)_2$— or —$CH_2O$—$(CH_2)_2$—

$R^8$ is

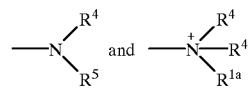

wherein $R^4$ and $R^5$ are independently selected from the group consisting of $R^2$, —$C(=NR^2)N(R^2)_2$, 2,2,2-trifluoroethyl or —$CH_2CH_2$—$OR^2$; and $R^{1a}$ is H or $C_{1-3}$alkyl;

$R^{11}$ is hydrogen, $R^2$, $CF_3$, $CH_2CF_3$ or $CH_2CH_2OR_2$;

$R^{12}$ is hydrogen, 1–2 $R^2$, 1–2 halogen, 1–2 $OR^2$ or 1–2 $CF_3$;

q is 0 or 1, and n is 0, 1 or 2.

7. A compound according to claim 1 which is selected from:

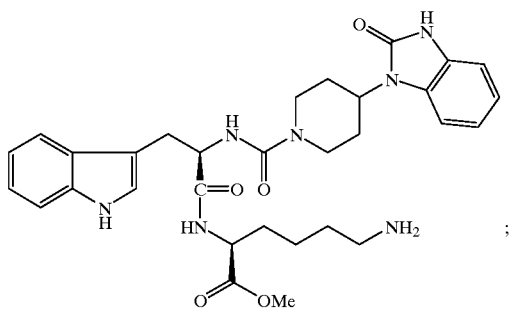

-continued

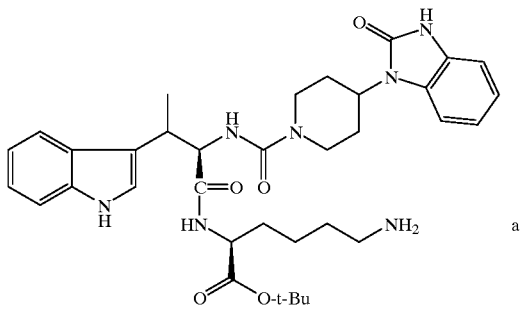

and

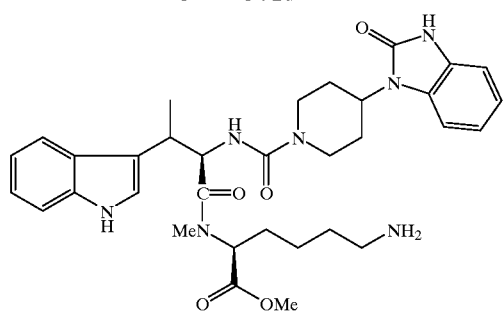

or a pharmaceutically acceptable salt or hydrate thereof.

8. A compound according to claim 1, depicted in Table I below:

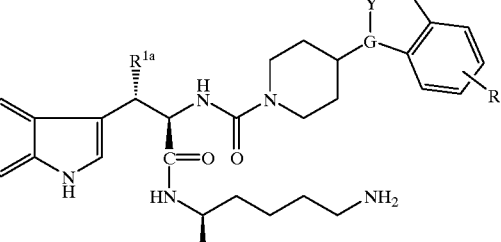

| $R^{1a}$ | $R^2$ | G—Y—X |
|---|---|---|
| H | H | N—CO—NH |
| CH$_3$ | H | N—CO—NH |
| CH$_3$ | 5-F | N—CO—NH |
| CH$_3$ | 5-F | N—CO—NCH$_2$CF$_3$ |
| CH$_3$ | H | N—CO—NCH$_3$ |
| CH$_3$ | H | N—CO—NCH$_2$CH$_3$ |
| CH$_3$ | H | N—CO—NCH$_2$CO$_2$H |
| CH$_3$ | H | N—C=N |
| CH$_3$ | 5-CH$_3$ | N—CO—NH and |
| CH$_3$ | 6-CH$_3$ | N—CO—NH | or a pharmaceutically acceptable salt or hydrate thereof.

9. A compound according to claim 1 which is selected from:

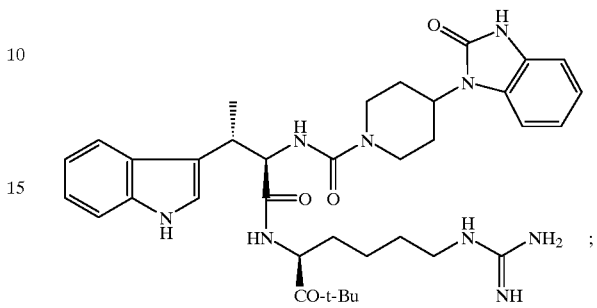

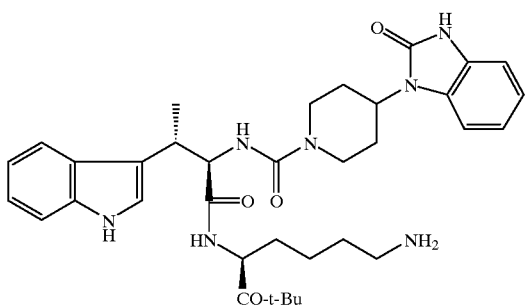

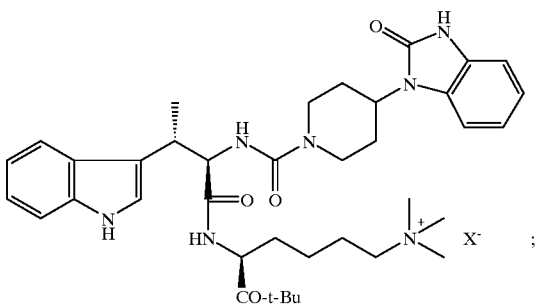

wherein X$^-$ is a negatively charged counterion

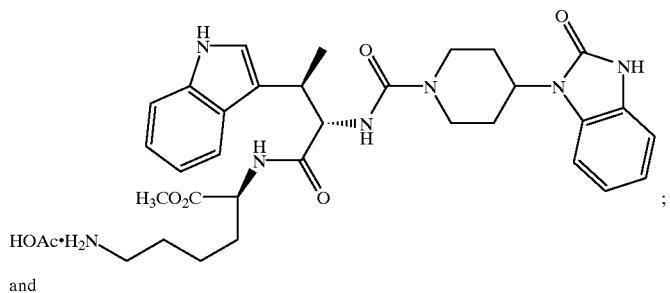
and
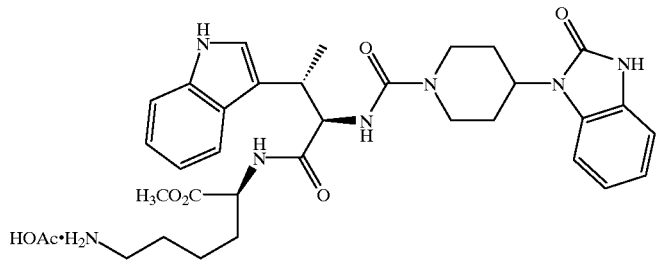
or a pharmaceutically acceptable salt or hydrate thereof.
10. A compound according to claim 1, depicted in Table II below:
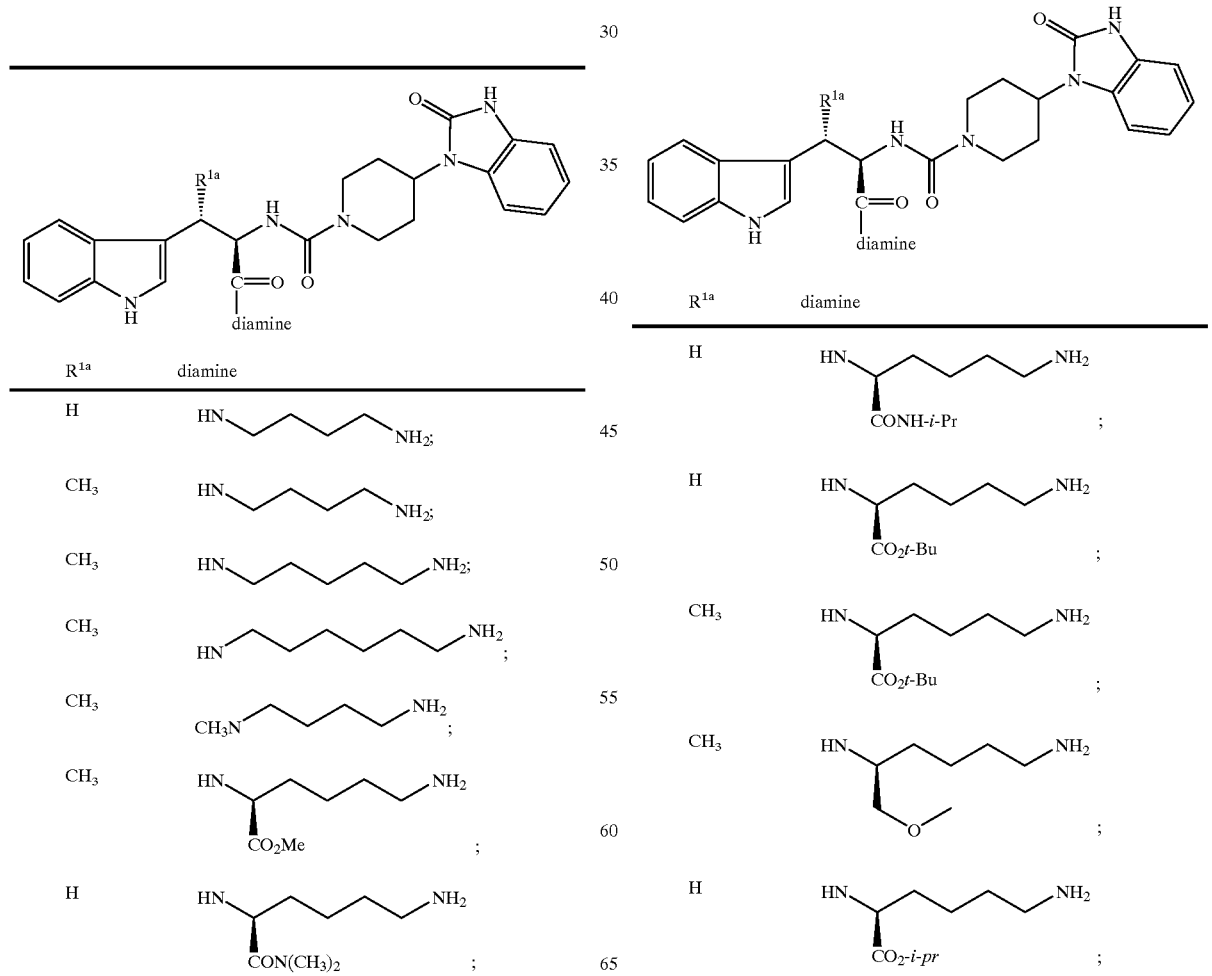

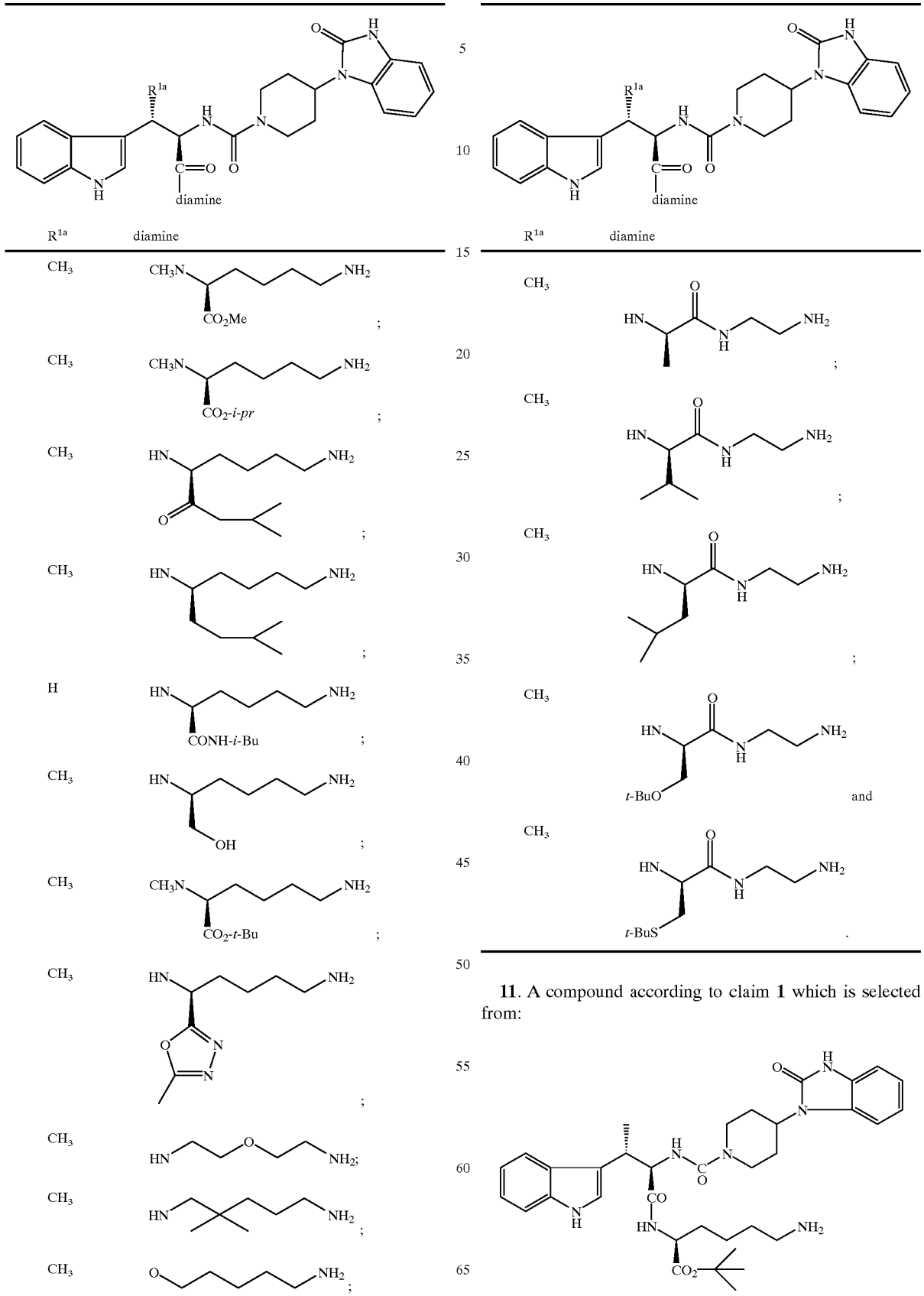
11. A compound according to claim 1 which is selected from:
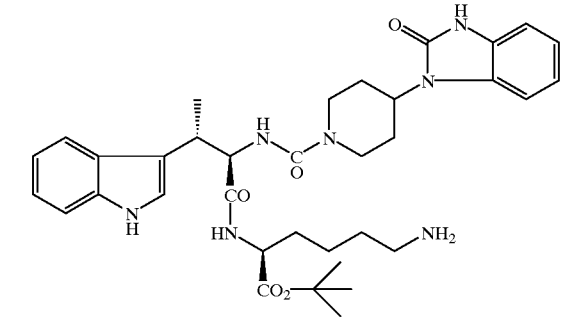

-continued
or
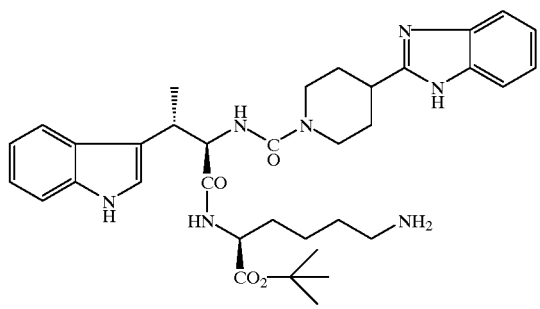
or a pharmaceutically acceptable salt thereof.
12. A pharmaceutical composition comprising a compound according to claim 1 and a pharmaceutically acceptable carrier.
13. A method of treating diabetes disease in a mammal in need of such treatment, which comprises administering to said mammal an effective amount of a somatostatin agonist of claim 1.
* * * * *